US011963955B2

United States Patent
Olaleye

(10) Patent No.: US 11,963,955 B2
(45) Date of Patent: Apr. 23, 2024

(54) COMPOSITIONS FOR AND METHODS OF INHIBITING SARS-CoV2 INFECTION

(71) Applicant: Texas Southern University, Houston, TX (US)

(72) Inventor: Omonike A. Olaleye, Houston, TX (US)

(73) Assignee: Texas Southern University, Houston, TX (US)

( * ) Notice: Subject to any disclaimer, the term of this patent is extended or adjusted under 35 U.S.C. 154(b) by 159 days.

(21) Appl. No.: 17/402,419

(22) Filed: Aug. 13, 2021

(65) Prior Publication Data

US 2022/0047571 A1    Feb. 17, 2022

Related U.S. Application Data

(60) Provisional application No. 63/076,936, filed on Sep. 11, 2020, provisional application No. 63/065,401, filed on Aug. 13, 2020.

(51) Int. Cl.
| | | |
|---|---|---|
| *A61K 31/47* | (2006.01) | |
| *A61K 31/137* | (2006.01) | |
| *A61K 33/30* | (2006.01) | |
| *A61K 45/06* | (2006.01) | |
| *A61P 31/14* | (2006.01) | |

(52) U.S. Cl.
CPC ............ *A61K 31/47* (2013.01); *A61K 31/137* (2013.01); *A61K 33/30* (2013.01); *A61K 45/06* (2013.01); *A61P 31/14* (2018.01)

(58) Field of Classification Search
None
See application file for complete search history.

(56) References Cited

U.S. PATENT DOCUMENTS

| | | | | |
|---|---|---|---|---|
| 3,857,877 A | * | 12/1974 | Somasekhara | ....... C07D 417/12 546/177 |
| 2006/0229356 A1 | | 10/2006 | Santoro | |
| 2008/0319087 A1 | | 12/2008 | Esperester et al. | |
| 2013/0231302 A1 | | 9/2013 | Raad et al. | |
| 2017/0304288 A1 | * | 10/2017 | Olaleye | .............. A61K 31/5365 |

FOREIGN PATENT DOCUMENTS

| | | | | |
|---|---|---|---|---|
| CN | 112315963 A | | 2/2021 | |
| WO | WO-2004073030 A2 | * | 8/2004 | .............. C07F 5/069 |
| WO | 2007/044695 A2 | | 4/2007 | |
| WO | 2009/140215 A2 | | 11/2009 | |
| WO | 2020/241759 A1 | | 12/2020 | |

OTHER PUBLICATIONS

International Search Report dated Nov. 26, 2021 in connection with PCT Application No. PCT/US2021/046024.
Written Opinion of the International Searching Authority dated Nov. 26, 2021 in connection with PCT Application No. PCT/US2021/046024.
Chen et al., "Structure Analysis of the Receptor Binding of 2019-nCoV," Biochemical and Biophysical Research Communications, Apr. 23, 2020, vol. 525, Issue 1, pp. 135-140.
Liu et al., "Hydroxychloroquine, a Less Toxic Derivative of Chloroquine, is Effective in Inhibiting SARS-CoV-2 Infection in Vitro," Cell Discovery, Mar. 18, 2020, vol. 6, No. 16, pp. 1-4.

* cited by examiner

*Primary Examiner* — Bong-Sook Baek
(74) *Attorney, Agent, or Firm* — Akerman LLP

(57) ABSTRACT

Severe Acute Respiratory Syndrome Coronavirus 2 (SARS-CoV-2), the etiological agent for coronavirus disease 2019 (COVID-19), has emerged as an ongoing global pandemic. Presently, there are no clinically approved vaccines nor drugs for COVID-19. Hence, there is an urgent need to accelerate the development of effective antivirals. One or more members of the 8-Hydroxyquinoline and Benzylamine structural classes inhibited SARS-CoV-2 infection induced cytopathic effect in vitro, inhibited the exopeptidase activity of angiotensin converting enzyme 2 (ACE2), and disrupted the binding between ACE2 and the Spike protein of SARS-CoV-2. This abstract is intended as a scanning tool for purposes of searching in the particular art and is not intended to be limiting of the present invention.

7 Claims, 18 Drawing Sheets

Table 1. Chemical Structure and Activity of Ambroxol Hydrochloride (AMB) and Bromhexine Hydrochloride (BHH) against SARS-CoV-2 induced Cytopathic Effect (CPE) in Vero E6 Cells.

| Inhibitor ID | Screen ID | Chemical Structure | | IC$_{50}$ (µM) | Maximum Inhibition at 30µM (%) |
|---|---|---|---|---|---|
| BHH | MDXC19T009 | (structure) | HCl | 21.72 | 91.08 |
| AMB | MDXC19T010 | (structure) | HCl | >30 | 14.25 |

FIG. 6

Table 2. Chemical Structure and Activity of Reference Inhibitors against SARS-CoV-2 induced Cytopathic Effect (CPE) in Vero E6 Cells.

| Inhibitor ID | Screen ID | Chemical Structure | $IC_{50}$ (µM) | Maximum Inhibition (%) | Concentration at Maximum % Inhibition (µM) |
|---|---|---|---|---|---|
| Calpain Inhibitor IV | AB01968858 | 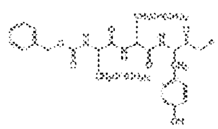 | 0.29 | 104.66 | 0.90 |
| Chloroquine | AB00053436 | 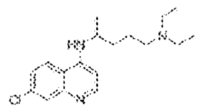 | 3.56 | 151.80 | 30.00 |
| Remdesivir | AB01952209 | 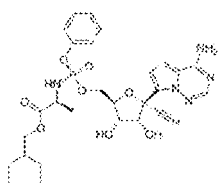 | 8.54 | 105.89 | 30.00 |
| Hydroxychloroquine | AB00053257 | 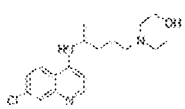 | 5.16 | 101.26 | 15.00 |
| E64d (Aloxistatin) | AB01955411 | 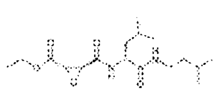 | 21.76 | 57.09 | 30.00 |

FIG. 7

Table 3. Cytotoxicity of Ambroxol Hydrochloride (AMB) and Bromhexine Hydrochloride (BHH) in Vero E6 Cells, in Comparison to Reference Inhibitors of SARS-CoV-2.

| Inhibitor ID | Cytotoxicity $CC_{50}$ (µM) | Minimum Viability (%) | Concentration at Minimum % Viability (µM) | Maximum Viability (%) | Concentration at Maximum % Viability (µM) |
|---|---|---|---|---|---|
| BHH | >30.00 | 103.27 | 30.00 | 133.17 | 0.12 |
| AMB | >30.00 | 113.35 | 30.00 | 124.37 | 1.88 |
| CalpainInhibitorIV | >7.17 | 97.74 | 7.17 | 113.22 | 0.45 |
| Chloroquine | >30.00 | 93.52 | 30.00 | 111.43 | 0.08 |
| Remdesivir | >30.00 | 101.07 | 0.120 | 109.76 | 15.00 |
| Hydroxychloroquine | >30.00 | 96.10 | 0.470 | 105.31 | 0.12 |
| E64d (Aloxistatin) | >30.00 | 97.45 | 30.000 | 104.15 | 0.47 |

FIG. 8

Table 4. Activity of Bromhexine Hydrochloride (BHH) and Ambroxol Hydrochloride (AMB) against rhACE2 and SARS-CoV-2 Spike (RBD) Glycoprotein Interaction.

| | Estimated Relative $IC_{50}$ (µM) for Spike (RBD)-rhACE2 Protein Interaction Assay | |
|---|---|---|
| Inhibitor ID | $IC_{50\_1}$ (µM) | $IC_{50\_2}$ (µM) |
| BHH | 1.19 | 42.90 |
| AMB | 0.82 | 231.60 |

FIG 9

COMPOSITIONS FOR AND METHODS OF INHIBITING SARS-CoV2 INFECTION

I. CROSS-REFERENCE TO RELATED APPLICATIONS

This patent application claims priority under 35 U.S.C. § 119(e) to U.S. Provisional Patent Application No. 63/065,401, filed Aug. 13, 2020, and U.S. Provisional Patent Application No. 63/076,936, filed Sep. 11, 2020, each of which is hereby incorporated herein by reference in its entirety.

II. STATEMENT REGARDING FEDERALLY SPONSORED RESEARCH

This invention was made with government support under 5G12MD007605-26 awarded by the National Institute on Minority Health and Health Disparities and the National Institutes of Health. The government has certain rights in the invention. In particular, this work was supported in part by Indirect Cost to Texas Southern University from research infrastructure support from grant number 5G12MD007605-26 from the National Institute on Minority Health and Health Disparities and the National Institutes of Health.

III. BACKGROUND

Severe Acute Respiratory Syndrome Coronavirus 2 (SARS-CoV-2), a novel RNA betacoronavirus, is the causative agent for coronavirus disease 2019 (COVID-19), which has emerged as an ongoing global pandemic.[104] Worldwide, SARS-CoV-2 has spread rampantly to more than 188 countries/regions and has resulted in over 200 million confirmed cases, including over 4.35 million deaths. In the United States, there have been more As of August 2021, there has been more than 37 million cases and 635,000 deaths, in the United States alone. About 80% of people infected with SARS-CoV-2 experience mild symptoms or are asymptomatic.[103] A majority of symptomatic patients with moderate to severe symptoms have shown a broad range of clinical manifestation and/or significant complications, including severe pneumonia, multi-organ failure, acute cardiac injury, neurological damage, septic shock, acute respiratory distress syndrome (ARDS).[38,55,61,116] Case tracking has revealed that individuals with pre-existing medical conditions have increased risk of COVID-19 related morbidity and mortality.[30]

Although there are several studies are investigating the potential utility of repurposing clinically approved drugs as treatment options for COVID-19,[36,79,83,88,95] the U.S. Food and Drug Administration (FDA) has approved only Remdesivir, an inhibitor of RNA dependent RNA Polymerase, and has granted emergency use authorization (EUA) for the rheumatoid arthritis drug baricitinib (Olumiant) for the treatment of hospitalized patients with severe cases of COVID-19.[19]

Despite advances in the understanding of the pathology of coronaviruses including SARS-CoV-2, there is still a need for compositions and methods that efficiently treat or prevent the development, progression, and reoccurrence of coronavirus infections including SARS-CoV-2 infections.

IV. BRIEF DESCRIPTION OF THE FIGURES

FIG. 6 shows the chemical structure and activity of Ambroxol Hydrochloride (AMB) and Bromhexine Hydrochloride (BHH) against SARS-CoV-2 induced Cytopathic Effect (CPR) and Vero E6 Cells.

FIG. 7 shows chemical structure and activity of reference inhibitors against SARS-CoV-2 induced Cytopathic Effect (CPE) in vero E6 cells.

FIG. 8 shows cytotoxicity of Ambroxol Hydrochloride (AMB) and Bromhexine Hydrochloride (BHH) in vero E6 cells, in comparison to reference inhibitors of SARS-CoV-2.

FIG. 9 shows activity of Ambroxol Hydrochloride (AMB) and Bromhexine Hydrochloride (BHH) against rhACE2 and SARS-CoV-2 spike (RBD) glycoprotein interaction.

V. BRIEF SUMMARY

Figure 1A:
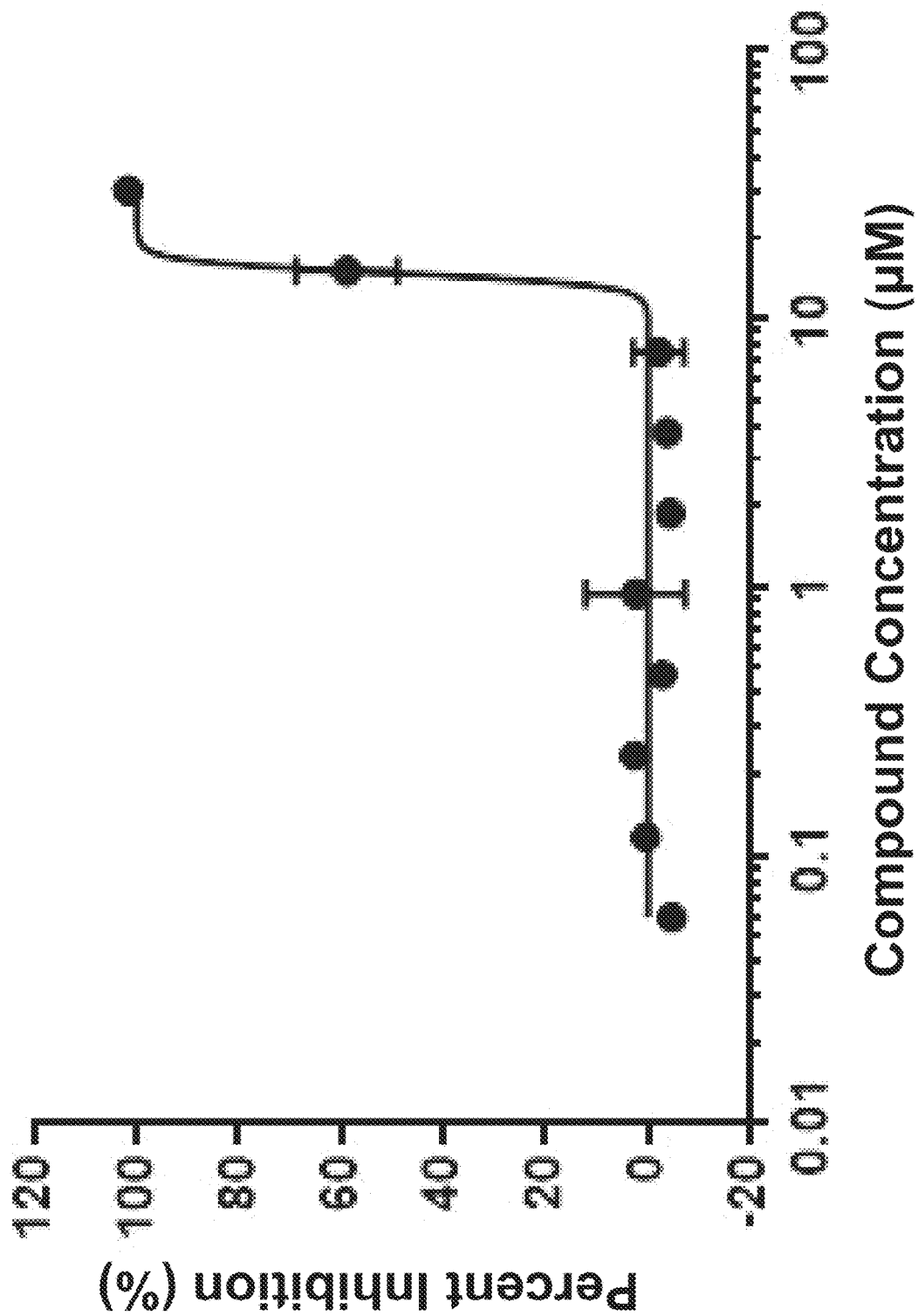
FIG. 1A-1C shows the efficacy of clioquinol (CLQ) and analogues against SARS-CoV-2 induced cytopathic effect (CPE) in Vero E6 cells: (A) CLBQ14, (B). CLCQ, and (C) CLQ.
Figure 1B:
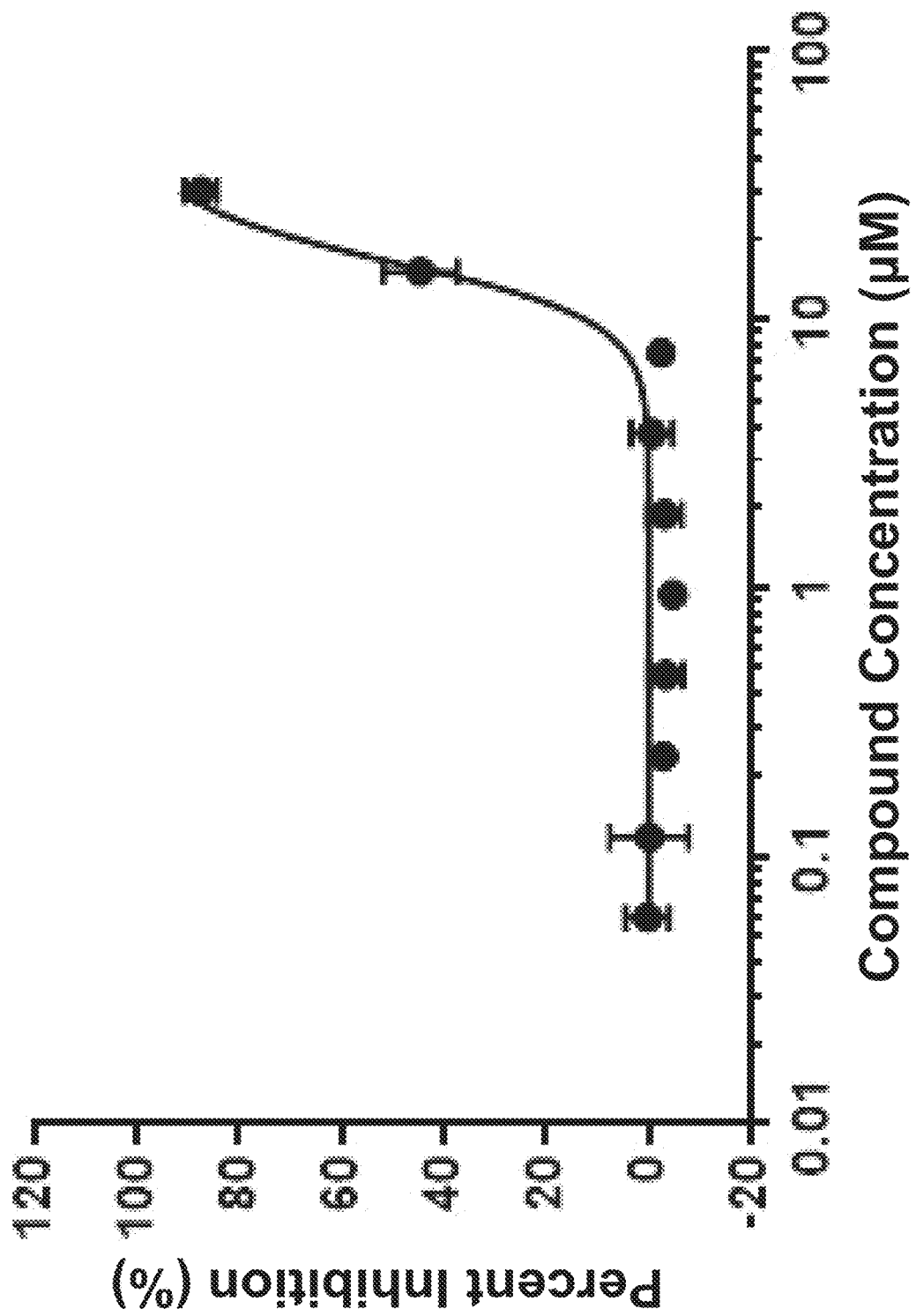
Figure 1C:
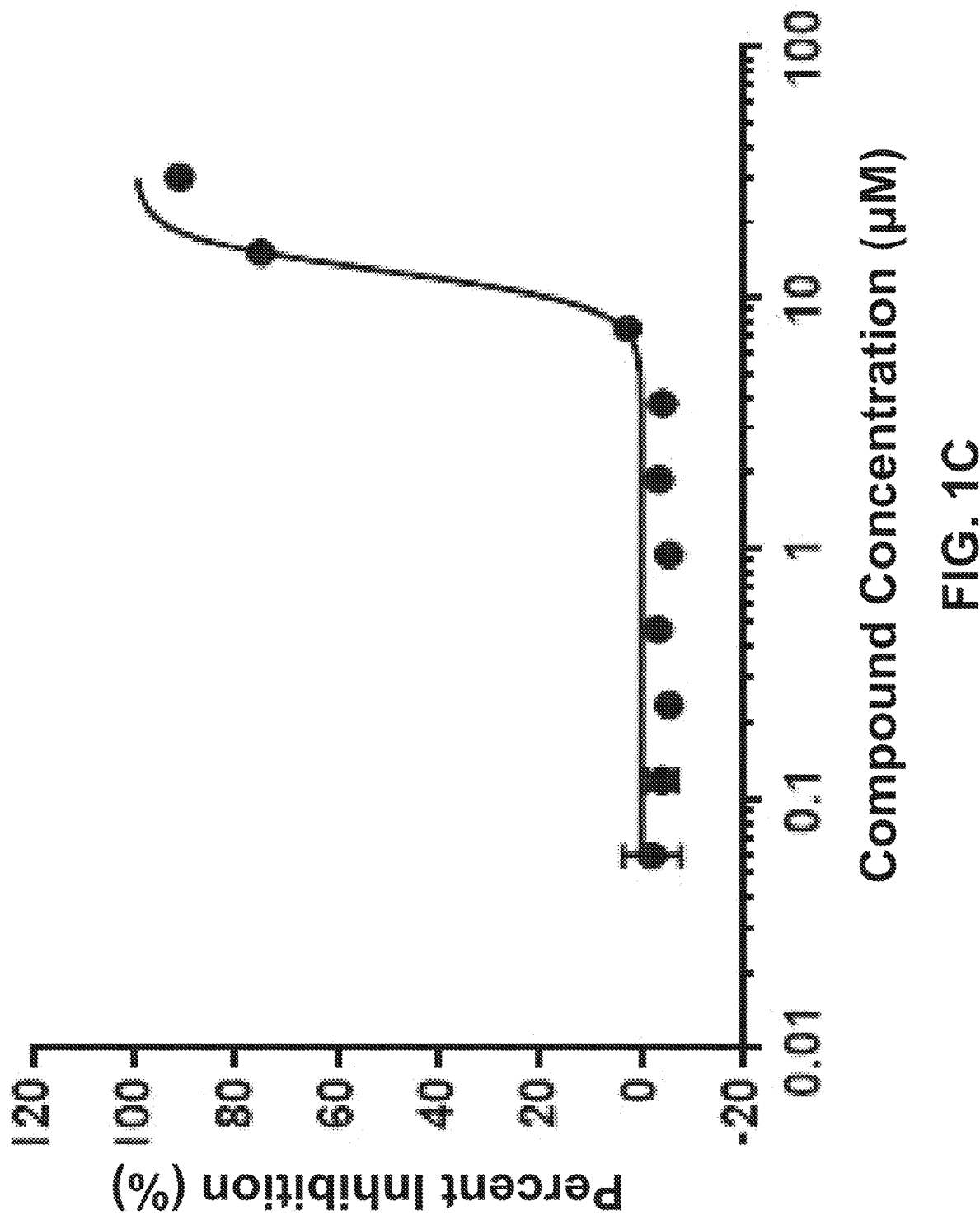
Figure 2A:
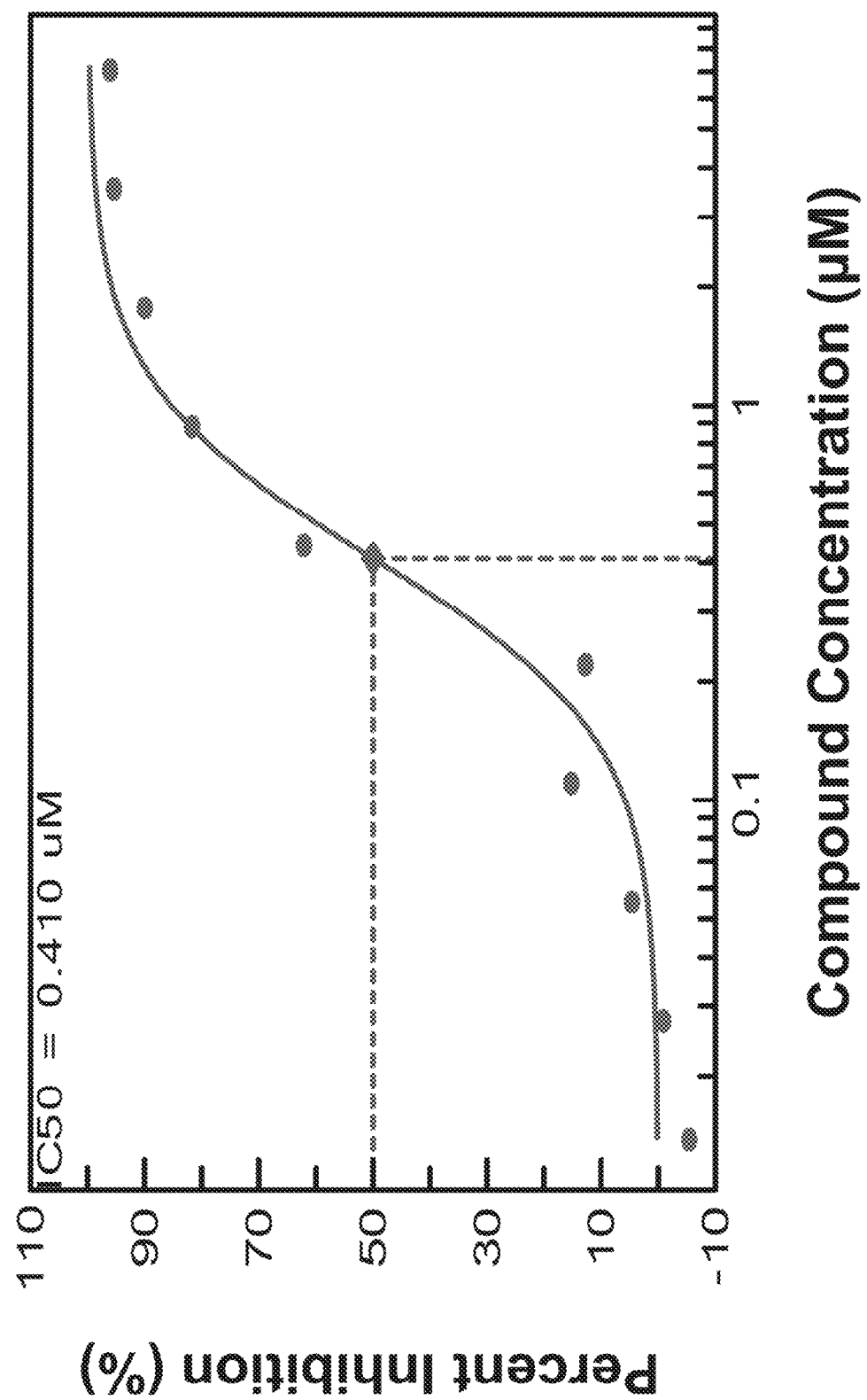
FIG. 2A-2E shows the efficacy of reference inhibitors against SARS-CoV-2 induced cytopathic effect (CPE) in Vero E6 cells: (A) Calpain Inhibitor IV, (B) Chloroquine, (C) Remdesivir, (D) Hydroxychloroquine, and (E) E64d (Aloxistatin).
Figure 2B:
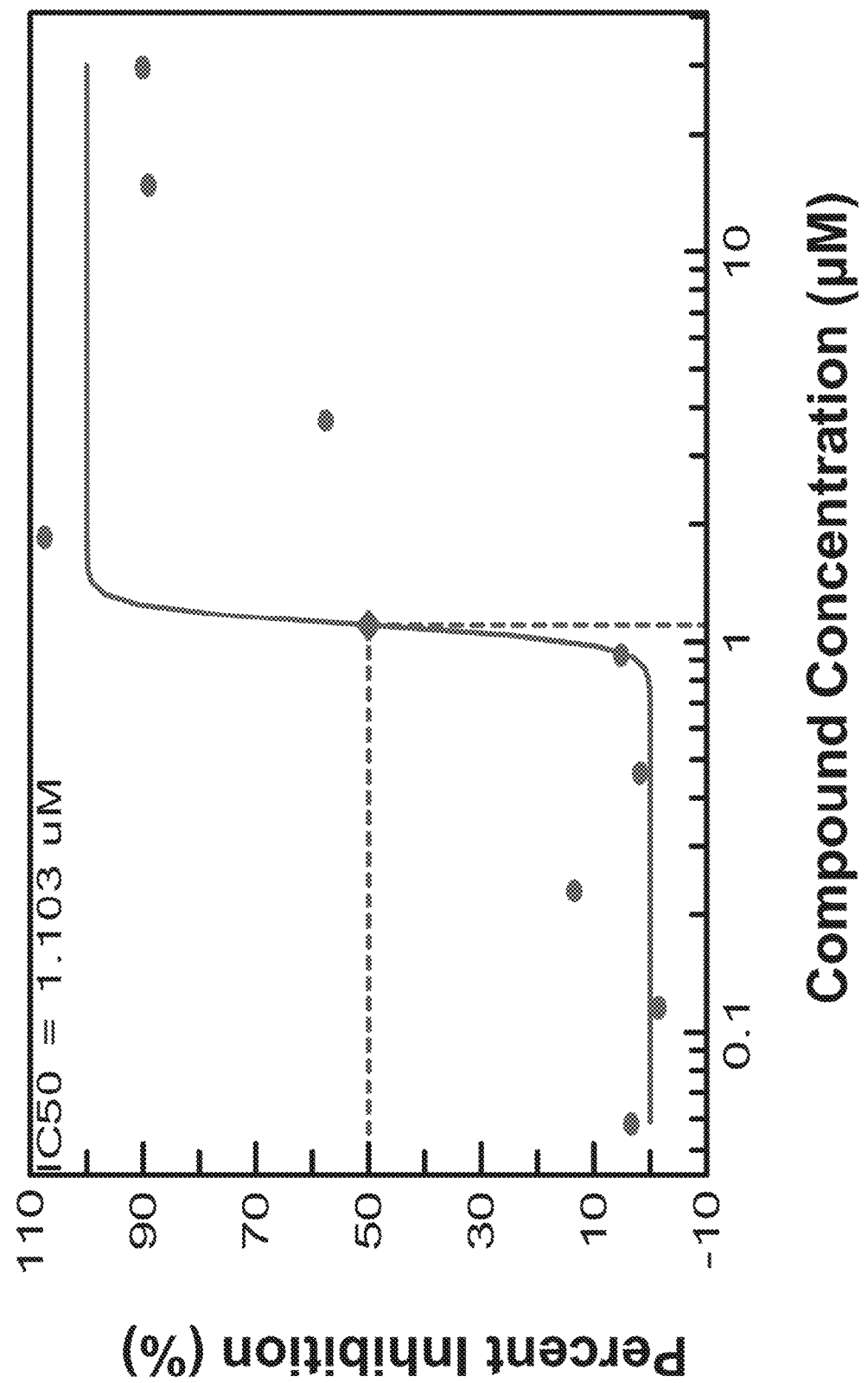
Figure 2C:
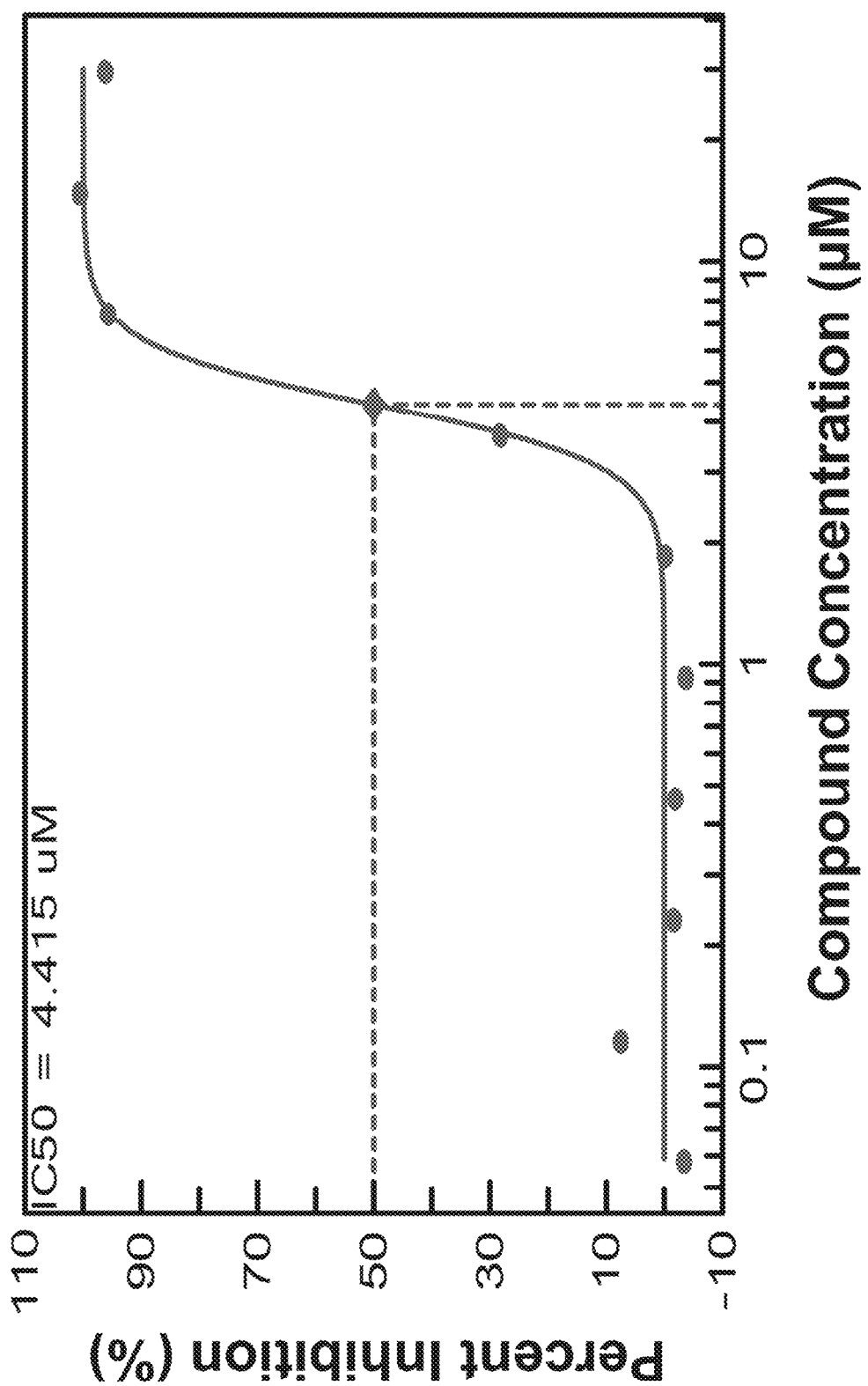
Figure 2D:
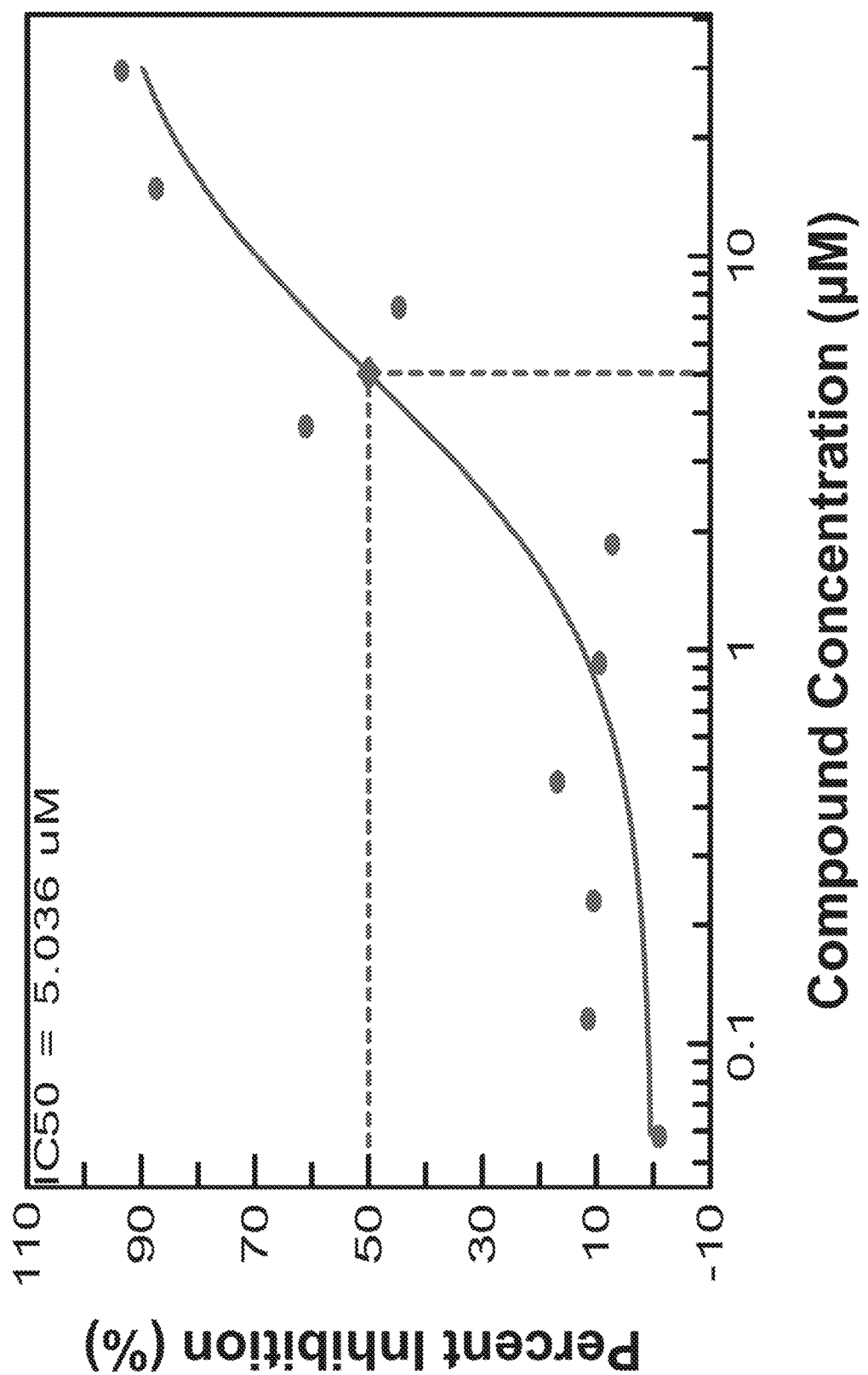
Figure 2E:
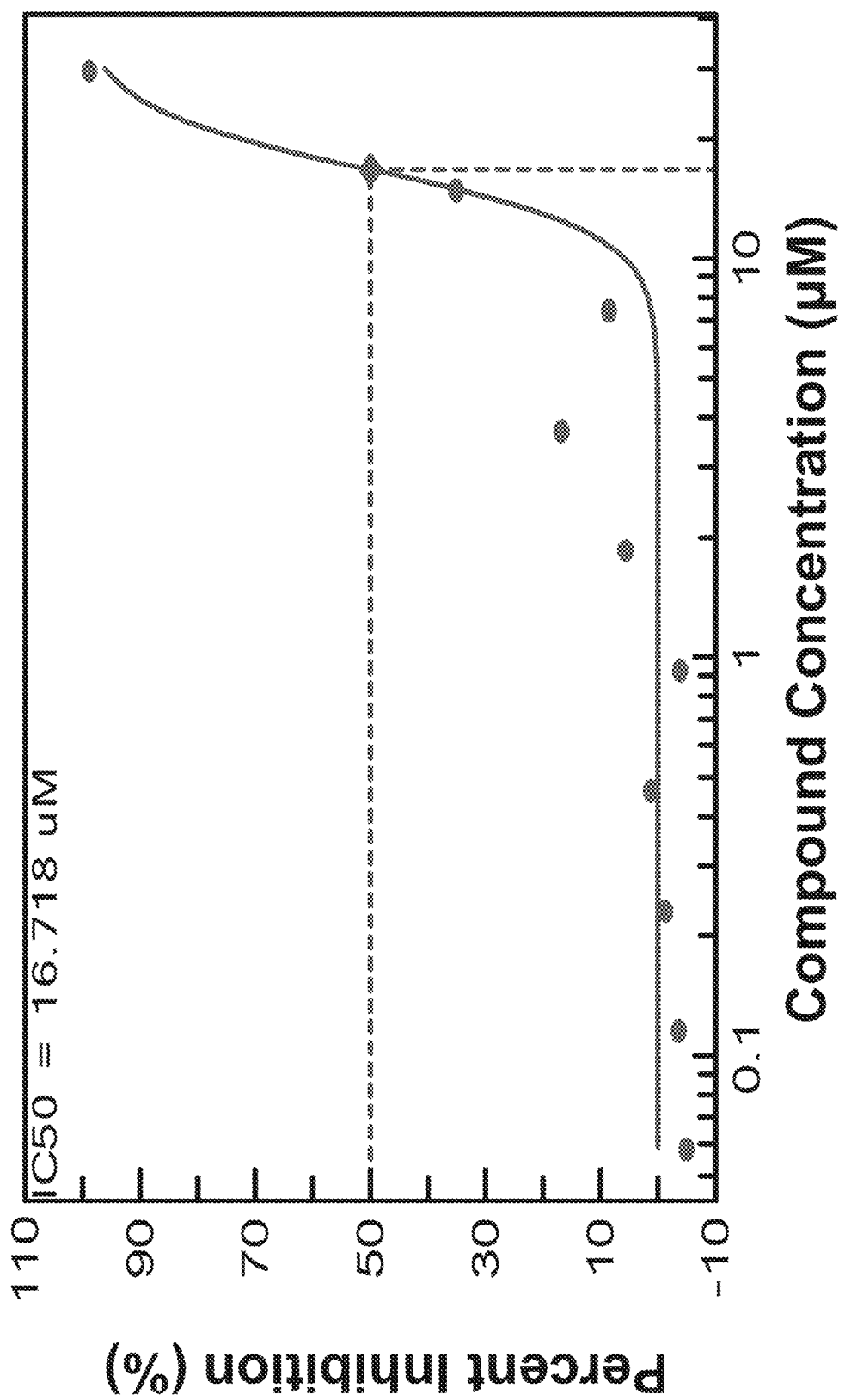
Figure 3:
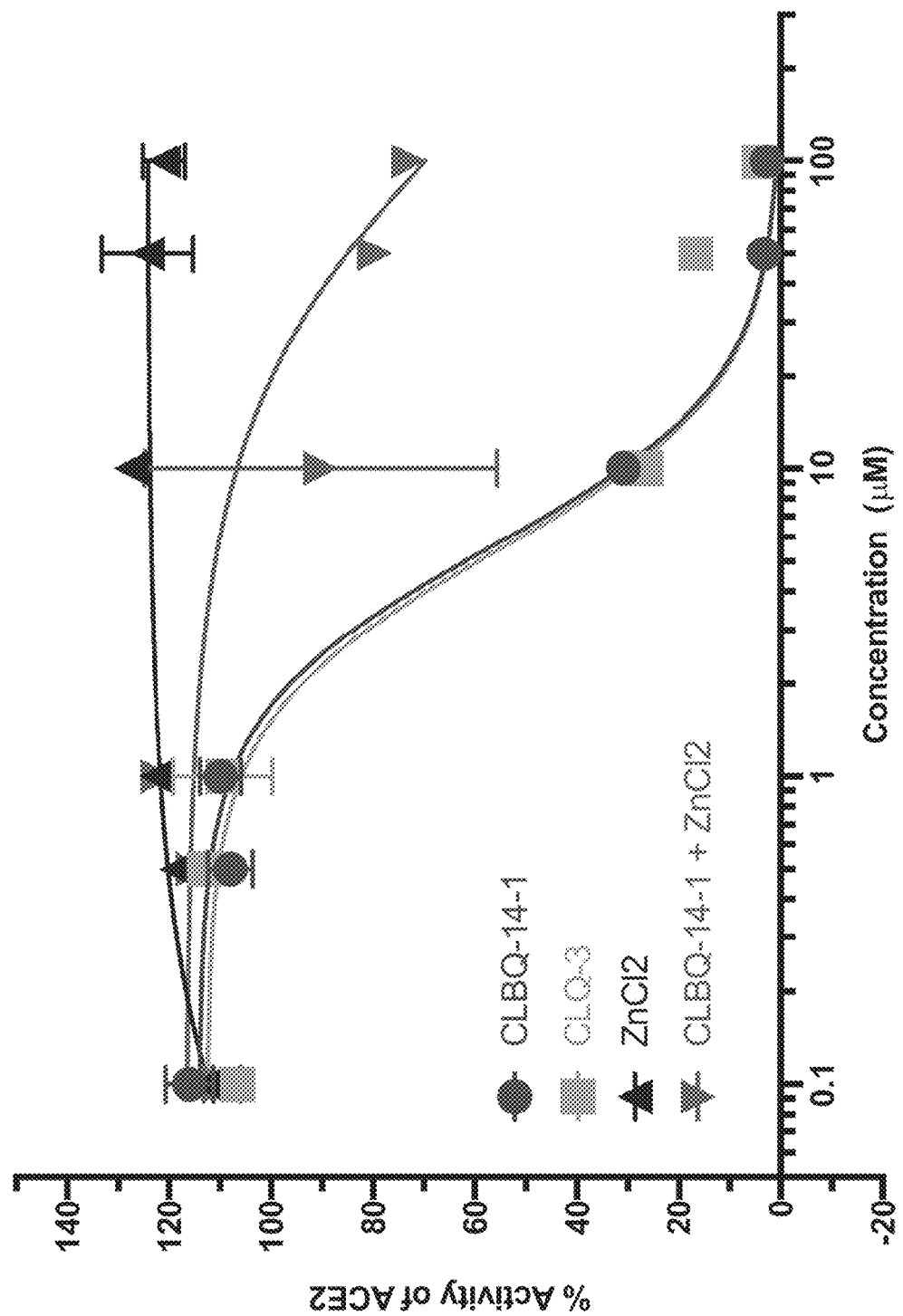
FIG. 3 shows the effect of clioquinol (CLQ) and analogues against ACE2 exopeptidase activity: (A) CLBQ14 (circles—red), (B) CLQ (squares—green), and (C) $ZnCl_2$ (triangle—blue), and (D) CLBQ14 and $ZnCl_2$ (inverted triangles—magenta).

Disclosed herein is a method comprising administering a composition comprising an effective amount of one or more compounds belonging to the 8-hydroxyquinoline structural class; and inhibiting or ameliorating a SARS-CoV-2 infection.

Disclosed herein is a method comprising administering a composition comprising an effective amount of CLQ, CLBQ14, or CLCQ, or analogs or derivatives thereof, or a combination thereof, and inhibiting or ameliorating a SARS-CoV-2 infection.

Disclosed herein is a method comprising administering a composition comprising an effective amount of one or more compounds belonging to the 8-hydroxyquinoline structural class; administering one or more clinically approved active agents; and inhibiting or ameliorating a SARS-CoV-2 infection.

Disclosed herein is a method comprising administering a composition comprising an effective amount of CLQ, CLBQ14, or CLCQ, or analogs or derivatives thereof, or a combination thereof; administering one or more clinically approved active agents; and inhibiting or ameliorating a SARS-CoV-2 infection.

Disclosed herein is a method comprising inhibiting or ameliorating a SARS-CoV-2 infection by administering a composition comprising one or more compounds belonging to the 8-hydroxyquinoline structural class.

Disclosed herein is a method comprising inhibiting or ameliorating a SARS-CoV-2 infection by administering a composition comprising an effective amount of CLQ, CLBQ14, or CLCQ, or analogs or derivatives thereof, or a combination thereof.

Disclosed herein is a method of inhibiting or ameliorating a SARS-CoV-2 infection comprising administering a composition comprising an effective amount of CLQ, CLBQ14, or CLCQ, or analogs or derivatives thereof, or a combination thereof, thereby inhibiting or ameliorating a SARS-CoV-2 infection.

Disclosed herein is a method of inhibiting or ameliorating a SARS-CoV-2 infection comprising administering a composition comprising an effective amount of one or more compounds belonging to the 8-hydroxyquinoline structural class, thereby inhibiting or ameliorating a SARS-CoV-2 infection.

Disclosed herein is a method of inhibiting or ameliorating a SARS-CoV-2 infection comprising administering a composition comprising an effective amount of CLQ, CLBQ14, or CLCQ, or analogs or derivatives thereof, or a combination thereof, and inhibiting or ameliorating a SARS-CoV-2 infection.

Disclosed herein is a method of inhibiting or ameliorating a SARS-CoV-2 infection comprising administering a composition comprising an effective amount of one or more compounds belonging to the 8-hydroxyquinoline structural class; and inhibiting or ameliorating a SARS-CoV-2 infection.

Disclosed herein is a method of inhibiting or ameliorating a SARS-CoV-2 infection comprising prophylactically administering a composition comprising an effective amount of CLQ, CLBQ14, or CLCQ, or analogs or derivatives thereof, or a combination thereof, and inhibiting or ameliorating a SARS-CoV-2 infection.

Disclosed herein is a method comprising administering a composition comprising an effective amount of CLQ, CLBQ14, or CLCQ, or analogs or derivatives thereof, or a combination thereof, and inhibiting or ameliorating one or more SARS-CoV-2 infection induced cytopathic effects.

Disclosed herein is a method comprising inhibiting or ameliorating one or more SARS-CoV-2 infection induced cytopathic effects by administering a composition comprising an effective amount of CLQ, CLBQ14, or CLCQ, or analogs or derivatives thereof, or a combination thereof.

Disclosed herein is a method of inhibiting or ameliorating one or more SARS-CoV-2 infection induced cytopathic effects comprising administering a composition comprising an effective amount of CLQ, CLBQ14, or CLCQ, or analogs or derivatives thereof, or a combination thereof.

Disclosed herein is a method of inhibiting or ameliorating one or more SARS-CoV-2 infection induced cytopathic effects in a subject comprising administering to a subject a composition comprising an effective amount of CLQ, CLBQ14, or CLCQ, or analogs or derivatives thereof, or a combination thereof, and inhibiting or ameliorating one or more SARS-CoV-2 infection induced cytopathic effects in the subject.

Disclosed herein is a method of inhibiting or ameliorating one or more SARS-CoV-2 infection induced cytopathic effects in a subject comprising inhibiting or ameliorating one or more SARS-CoV-2 infection induced cytopathic effects in the subject by administering to a subject a composition comprising an effective amount of CLQ, CLBQ14, or CLCQ, or analogs or derivatives thereof, or a combination thereof.

Disclosed herein is a method comprising inhibiting or reducing the exopeptidase activity of angiotensin converting enzyme 2 (ACE2) by administering a composition comprising an effective amount of CLQ, CLBQ14, or CLCQ, or analogs or derivatives thereof, or a combination thereof.

Disclosed herein is a method comprising inhibiting or reducing the exopeptidase activity of angiotensin converting enzyme 2 (ACE2) by administering a composition comprising an effective amount of CLQ, CLBQ14, or CLCQ, or analogs or derivatives thereof, or a combination thereof, and by administering a composition comprising an effective amount of zinc chloride.

Disclosed herein is a method of inhibiting or reducing exopeptidase activity of an enzyme comprising administering a composition comprising an effective amount of CLQ, CLBQ14, or CLCQ, or analogs or derivatives thereof, or a combination thereof, and inhibiting or reducing the exopeptidase activity of angiotensin converting enzyme 2 (ACE2).

Disclosed herein is a method of inhibiting or reducing exopeptidase activity of an enzyme comprising administering a composition comprising an effective amount of CLQ, CLBQ14, or CLCQ, or analogs or derivatives thereof, or a combination thereof, administering a composition comprising an effective amount of zinc chloride; and inhibiting or reducing the exopeptidase activity of angiotensin converting enzyme 2 (ACE2).

Disclosed herein is a method of inhibiting or reducing exopeptidase activity of an enzyme comprising inhibiting or reducing the exopeptidase activity of angiotensin converting enzyme 2 (ACE2) by administering a composition comprising an effective amount of CLQ, CLBQ14, or CLCQ, or analogs or derivatives thereof, or a combination thereof.

Disclosed herein is method of inhibiting or reducing exopeptidase activity of an enzyme comprising inhibiting or reducing the exopeptidase activity of angiotensin converting enzyme 2 (ACE2) by administering a composition comprising an effective amount of CLQ, CLBQ14, or CLCQ, or analogs or derivatives thereof, or a combination thereof and by administering a composition comprising an effective amount of zinc chloride.

Disclosed herein is a method comprising administering a composition comprising an effective amount of CLQ, CLBQ14, or CLCQ, or analogs or derivatives thereof, or a combination thereof, and inhibiting or disrupting the physical interaction of angiotensin converting enzyme 2 (ACE2) with the Spike (S) glycoprotein of SARS-CoV-2.

Disclosed herein is a method comprising inhibiting or disrupting the physical interaction of angiotensin converting enzyme 2 (ACE2) with the Spike (S) glycoprotein of SARS-CoV-2 by administering a composition comprising an effective amount of CLQ, CLBQ14, or CLCQ, or analogs or derivatives thereof, or a combination thereof.

Disclosed herein is a method of inhibiting or disrupting the physical interaction of angiotensin converting enzyme 2 (ACE2) with the Spike (S) glycoprotein of SARS-CoV-2 comprising administering a composition comprising an effective amount of CLQ, CLBQ14, or CLCQ, or analogs or derivatives thereof, or a combination thereof, thereby inhibiting or disrupting the physical interaction of angiotensin converting enzyme 2 (ACE2) with the Spike (S) glycoprotein of SARS-CoV-2.

Disclosed herein is a method of inhibiting or reducing viral infectivity in a subject comprising administering to a subject a composition comprising an effective amount of CLQ, CLBQ14, or CLCQ, or analogs or derivatives thereof, or a combination thereof, and inhibiting or disrupting the physical interaction of angiotensin converting enzyme 2 (ACE2) with the Spike (S) glycoprotein of SARS-CoV-2, thereby inhibiting or reducing viral infectivity.

Disclosed herein is a method of inhibiting or reducing viral infectivity in a subject comprising inhibiting or disrupting the physical interaction of angiotensin converting enzyme 2 (ACE2) with the Spike (S) glycoprotein of SARS-CoV-2 by administering to a subject a composition comprising an effective amount of CLQ, CLBQ14, or CLCQ, or analogs or derivatives thereof, or a combination thereof, thereby inhibiting or reducing viral infectivity.

Disclosed herein is a method of inhibiting or ameliorating a SARS-CoV-2 infection in a subject comprising administering to a subject a composition comprising an effective amount of CLQ, CLBQ14, or CLCQ, or analogs or derivatives thereof, or a combination thereof, and inhibiting or disrupting the physical interaction of angiotensin converting enzyme 2 (ACE2) with the Spike (S) glycoprotein of SARS-CoV-2, thereby inhibiting or ameliorating a SARS-CoV-2 infection.

Disclosed herein is a method of inhibiting or ameliorating a SARS-CoV-2 infection in a subject comprising inhibiting or disrupting the physical interaction of angiotensin converting enzyme 2 (ACE2) with the Spike (S) glycoprotein of SARS-CoV-2 by administering to a subject a composition comprising an effective amount of CLQ, CLBQ14, or CLCQ, or analogs or derivatives thereof, or a combination thereof, thereby inhibiting or ameliorating a SARS-CoV-2 infection.

Disclosed herein is a method of inhibiting or reducing viral entry into cells of a subject comprising administering to a subject a composition comprising an effective amount of CLQ, CLBQ14, or CLCQ, or analogs or derivatives thereof, or a combination thereof, and inhibiting or disrupting the physical interaction of angiotensin converting enzyme 2 (ACE2) with the Spike (S) glycoprotein of SARS-CoV-2, thereby inhibiting or reducing viral entry into cells of the subject.

Disclosed herein is a method of inhibiting or reducing viral entry into cells of a subject comprising inhibiting or disrupting the physical interaction of angiotensin converting enzyme 2 (ACE2) with the Spike (S) glycoprotein of SARS-CoV-2 by administering to a subject a composition comprising an effective amount of CLQ, CLBQ14, or CLCQ, or analogs or derivatives thereof, or a combination thereof, thereby inhibiting or reducing viral entry into cells of the subject.

Disclosed herein is composition comprising a composition comprising an effective amount of one or more compounds belonging to the 8-hydroxyquinoline structural class; and a pharmaceutically acceptable diluent, carrier, excipient, or stabilizer, wherein the composition inhibits or ameliorates a SARS-CoV-2 infection.

Disclosed herein is a composition comprising an effective amount of CLQ, CLBQ14, or CLCQ, or analogs or derivatives thereof, or a combination thereof, and a pharmaceutically acceptable diluent, carrier, excipient, or stabilizer, wherein the composition inhibits or ameliorates a SARS-CoV-2 infection.

Disclosed herein is composition comprising a composition comprising an effective amount of one or more compounds belonging to the 8-hydroxyquinoline structural class; an effective amount of one or more clinically approved active agents; and a pharmaceutically acceptable diluent, carrier, excipient, or stabilizer, wherein the composition inhibits or ameliorates a SARS-CoV-2 infection.

Disclosed herein is a composition comprising an effective amount of CLQ, CLBQ14, or CLCQ, or analogs or derivatives thereof, or a combination thereof; an effective amount of one or more clinically approved active agents; and a pharmaceutically acceptable diluent, carrier, excipient, or stabilizer, wherein the composition inhibits or ameliorates a SARS-CoV-2 infection. Disclosed herein is a composition comprising an effective amount of CLQ, CLBQ14, or CLCQ, or analogs or derivatives thereof, or a combination thereof, and a pharmaceutically acceptable diluent, carrier, excipient, or stabilizer, wherein the composition inhibits or ameliorates one or more SARS-CoV-2 infection induced cytopathic effects.

Disclosed herein is a composition comprising an effective amount of CLQ, CLBQ14, or CLCQ, or analogs or derivatives thereof, or a combination thereof; an effective amount of one or more anti-viral agents; and a pharmaceutically acceptable diluent, carrier, excipient, or stabilizer, wherein the composition inhibits or ameliorates one or more SARS-CoV-2 infection induced cytopathic effects.

Disclosed herein is a composition for inhibiting or ameliorating cytopathic effects in a subject comprising an effective amount of CLQ, CLBQ14, or CLCQ, or analogs or derivatives thereof, or a combination thereof, and a pharmaceutically acceptable diluent, carrier, excipient, or stabilizer, wherein the composition inhibits or ameliorates one or more cytopathic effects in a subject in need thereof.

Disclosed herein is a composition for inhibiting or ameliorating cytopathic effects in a subject comprising an effective amount of CLQ, CLBQ14, or CLCQ, or analogs or derivatives thereof, or a combination thereof; an effective amount of one or more anti-viral agents; and a pharmaceutically acceptable diluent, carrier, excipient, or stabilizer, wherein the composition inhibits or ameliorates one or more cytopathic effects in a subject in need thereof.

Disclosed herein is a composition for inhibiting or ameliorating one or more SARS-CoV-2 infection induced cytopathic effects in a subject comprising an effective amount of CLQ, CLBQ14, or CLCQ, or analogs or derivatives thereof, or a combination thereof, and a pharmaceutically acceptable diluent, carrier, excipient, or stabilizer, wherein the composition inhibits or ameliorates one or more cytopathic effects in a subject diagnosed with or suspected of having a SARS-CoV-2 infection.

Disclosed herein is a composition for inhibiting or ameliorating one or more SARS-CoV-2 infection induced cytopathic effects in a subject comprising an effective amount of CLQ, CLBQ14, or CLCQ, or analogs or derivatives thereof, or a combination thereof; an effective amount of one or more anti-viral agents; and a pharmaceutically acceptable diluent, carrier, excipient, or stabilizer; wherein the composition inhibits or ameliorates one or more cytopathic effects in a subject diagnosed with or suspected of having a SARS-CoV-2 infection.

Disclosed herein is a composition for inhibiting or reducing exopeptidase activity of an enzyme comprising an effective amount of CLQ, CLBQ14, or CLCQ, or analogs or derivatives thereof, or a combination thereof, and a pharmaceutically acceptable diluent, carrier, excipient, or stabilizer, wherein the composition inhibits or reduces the exopeptidase activity of angiotensin converting enzyme 2 (ACE2).

Disclosed herein is a composition for inhibiting or reducing exopeptidase activity of an enzyme comprising an effective amount of CLQ, CLBQ14, or CLCQ, or analogs or derivatives thereof, or a combination thereof; and an effective amount of zinc chloride; wherein the composition inhibits or reduces the exopeptidase activity of angiotensin converting enzyme 2 (ACE2).

Disclosed herein is a composition for inhibiting or reducing exopeptidase activity of an enzyme comprising an effective amount of CLQ, CLBQ14, or CLCQ, or analogs or derivatives thereof, or a combination thereof, wherein the composition inhibits or disrupts the physical interaction of angiotensin converting enzyme 2 (ACE2) with the Spike (S)

glycoprotein of SARS-CoV-2, thereby inhibiting or reducing the exopeptidase activity of angiotensin converting enzyme 2 (ACE2).

Disclosed herein is a composition for inhibiting or reducing exopeptidase activity of an enzyme comprising an effective amount of CLQ, CLBQ14, or CLCQ, or analogs or derivatives thereof, or a combination thereof, and an effective amount of zinc chloride, wherein the composition inhibits or disrupts the physical interaction of angiotensin converting enzyme 2 (ACE2) with the Spike (S) glycoprotein of SARS-CoV-2, thereby inhibiting or reducing the exopeptidase activity of angiotensin converting enzyme 2 (ACE2).

Disclosed herein is a composition comprising an effective amount of CLQ, CLBQ14, or CLCQ, or analogs or derivatives thereof, or a combination thereof, wherein the composition inhibits or disrupts the physical interaction of angiotensin converting enzyme 2 (ACE2) with the Spike (S) glycoprotein of SARS-CoV-2.

Disclosed herein is a composition for inhibiting or disrupting the physical interaction of angiotensin converting enzyme 2 (ACE2) with the Spike (S) glycoprotein of SARS-CoV-2 comprising an effective amount of CLQ, CLBQ14, or CLCQ, or analogs or derivatives thereof, or a combination thereof.

Disclosed herein is a composition for inhibiting or reducing viral infectivity in a subject comprising an effective amount of CLQ, CLBQ14, or CLCQ, or analogs or derivatives thereof, or a combination thereof, wherein the composition inhibits or disrupts the physical interaction of angiotensin converting enzyme 2 (ACE2) with the Spike (S) glycoprotein of SARS-CoV-2, thereby inhibiting or reducing viral infectivity.

Disclosed herein is a composition for inhibiting or ameliorating a SARS-CoV-2 infection in a subject comprising an effective amount of CLQ, CLBQ14, or CLCQ, or analogs or derivatives thereof, or a combination thereof, wherein the composition inhibits or disrupts the physical interaction of angiotensin converting enzyme 2 (ACE2) with the Spike (S) glycoprotein of SARS-CoV-2, thereby inhibiting or ameliorating a SARS-CoV-2 infection.

Disclosed herein is a composition for inhibiting or reducing viral entry into cells of a subject comprising an effective amount of CLQ, CLBQ14, or CLCQ, or analogs or derivatives thereof, or a combination thereof, and wherein the composition inhibits or disrupts they physical interactions of angiotensin converting enzyme 2 (ACE2) and the Spike (S) glycoprotein of SARS-CoV-2, thereby inhibiting or reducing viral entry into cells of the subject.

Disclosed herein is a method comprising administering a composition comprising an effective amount of one or more compounds belonging to the benzylamine structural class; and inhibiting or ameliorating a SARS-CoV-2 infection.

Disclosed herein is a method comprising administering a composition comprising an effective amount of AMB or BHH, or analogs or derivatives thereof, or a combination thereof, and inhibiting or ameliorating a SARS-CoV-2 infection.

Disclosed herein is a method comprising administering a composition comprising an effective amount of one or more compounds belonging to the benzylamine structural class; administering one or more clinically approved active agents; and inhibiting or ameliorating a SARS-CoV-2 infection.

Disclosed herein is a method comprising administering a composition comprising an effective amount of AMB or BHH, or analogs or derivatives thereof, or a combination thereof; administering one or more clinically approved active agents; and inhibiting or ameliorating a SARS-CoV-2 infection.

Disclosed herein is a method comprising inhibiting or ameliorating a SARS-CoV-2 infection by administering a composition comprising one or more compounds belonging to the benzylamine structural class.

Disclosed herein is a method comprising inhibiting or ameliorating a SARS-CoV-2 infection by administering a composition comprising an effective amount of AMB or BHH, or analogs or derivatives thereof, or a combination thereof.

Disclosed herein is a method of inhibiting or ameliorating a SARS-CoV-2 infection comprising administering a composition comprising an effective amount of AMB or BHH, or analogs or derivatives thereof, or a combination thereof, thereby inhibiting or ameliorating a SARS-CoV-2 infection.

Disclosed herein is a method of inhibiting or ameliorating a SARS-CoV-2 infection comprising administering a composition comprising an effective amount of one or more compounds belonging to the benzylamine structural class, thereby inhibiting or ameliorating a SARS-CoV-2 infection.

Disclosed herein is a method of inhibiting or ameliorating a SARS-CoV-2 infection comprising administering a composition comprising an effective amount of AMB or BHH, or analogs or derivatives thereof, or a combination thereof, and inhibiting or ameliorating a SARS-CoV-2 infection.

A method of inhibiting or ameliorating a SARS-CoV-2 infection comprising administering a composition comprising an effective amount of one or more compounds belonging to the benzylamine structural class; and inhibiting or ameliorating a SARS-CoV-2 infection.

Disclosed herein is a method of inhibiting or ameliorating a SARS-CoV-2 infection comprising prophylactically administering a composition comprising an effective amount of AMB or BHH, or analogs or derivatives thereof, or a combination thereof, and inhibiting or ameliorating a SARS-CoV-2 infection.

Disclosed herein is a method comprising administering a composition comprising an effective amount of AMB or BHH, or analogs or derivatives thereof, or a combination thereof, and inhibiting or ameliorating one or more SARS-CoV-2 infection induced cytopathic effects.

Disclosed herein is a method comprising inhibiting or ameliorating one or more SARS-CoV-2 infection induced cytopathic effects by administering a composition comprising an effective amount of AMB or BHH, or analogs or derivatives thereof, or a combination thereof.

Disclosed herein is a method of inhibiting or ameliorating one or more SARS-CoV-2 infection induced cytopathic effects comprising administering a composition comprising an effective amount of AMB or BHH, or analogs or derivatives thereof, or a combination thereof.

Disclosed herein is a method of inhibiting or ameliorating one or more SARS-CoV-2 infection induced cytopathic effects in a subject comprising administering to a subject a composition comprising an effective amount of AMB or BHH, or analogs or derivatives thereof, or a combination thereof, and inhibiting or ameliorating one or more SARS-CoV-2 infection induced cytopathic effects in the subject.

Disclosed herein is a method of inhibiting or ameliorating one or more SARS-CoV-2 infection induced cytopathic effects in a subject comprising inhibiting or ameliorating one or more SARS-CoV-2 infection induced cytopathic effects in the subject by administering to a subject a composition comprising an effective amount of AMB or BHH, or analogs or derivatives thereof, or a combination thereof.

Disclosed herein is a method comprising inhibiting or reducing the exopeptidase activity of angiotensin converting enzyme 2 (ACE2) by administering a composition comprising an effective amount of AMB or BHH, or analogs or derivatives thereof, or a combination thereof.

Disclosed herein is a method of inhibiting or reducing exopeptidase activity of an enzyme comprising administering a composition comprising an effective amount of AMB or BHH, or analogs or derivatives thereof, or a combination thereof, and inhibiting or reducing the exopeptidase activity of angiotensin converting enzyme 2 (ACE2).

Disclosed herein is a method of inhibiting or reducing exopeptidase activity of an enzyme comprising inhibiting or reducing the exopeptidase activity of angiotensin converting enzyme 2 (ACE2) by administering a composition comprising an effective amount of AMB or BHH, or analogs or derivatives thereof, or a combination thereof.

Disclosed herein is a method comprising administering a composition comprising an effective amount of AMB or BHH, or analogs or derivatives thereof, or a combination thereof, and inhibiting or disrupting the physical interaction of angiotensin converting enzyme 2 (ACE2) with the Spike (S) glycoprotein of SARS-CoV-2.

Disclosed herein is a method comprising inhibiting or disrupting the physical interaction of angiotensin converting enzyme 2 (ACE2) with the Spike (S) glycoprotein of SARS-CoV-2 by administering a composition comprising an effective amount of AMB or BHH, or analogs or derivatives thereof, or a combination thereof.

Disclosed herein is a method of inhibiting or disrupting the physical interaction of angiotensin converting enzyme 2 (ACE2) with the Spike (S) glycoprotein of SARS-CoV-2 comprising administering a composition comprising an effective amount of AMB or BHH, or analogs or derivatives thereof, or a combination thereof, thereby inhibiting or disrupting the physical interaction of angiotensin converting enzyme 2 (ACE2) with the Spike (S) glycoprotein of SARS-CoV-2.

Disclosed herein is a method of inhibiting or reducing viral infectivity in a subject comprising administering to a subject a composition comprising an effective amount of AMB or BHH, or analogs or derivatives thereof, or a combination thereof, and inhibiting or disrupting the physical interaction of angiotensin converting enzyme 2 (ACE2) with the Spike (S) glycoprotein of SARS-CoV-2, thereby inhibiting or reducing viral infectivity.

Disclosed herein is a method of inhibiting or reducing viral infectivity in a subject comprising inhibiting or disrupting the physical interaction of angiotensin converting enzyme 2 (ACE2) with the Spike (S) glycoprotein of SARS-CoV-2 by administering to a subject a composition comprising an effective amount of AMB or BHH, or analogs or derivatives thereof, or a combination thereof, thereby inhibiting or reducing viral infectivity.

Disclosed herein is a method of inhibiting or ameliorating a SARS-CoV-2 infection in a subject comprising administering to a subject a composition comprising an effective amount of AMB or BHH, or analogs or derivatives thereof, or a combination thereof, and inhibiting or disrupting the physical interaction of angiotensin converting enzyme 2 (ACE2) with the Spike (S) glycoprotein of SARS-CoV-2, thereby inhibiting or ameliorating a SARS-CoV-2 infection.

Disclosed herein is a method of inhibiting or ameliorating a SARS-CoV-2 infection in a subject comprising inhibiting or disrupting the physical interaction of angiotensin converting enzyme 2 (ACE2) with the Spike (S) glycoprotein of SARS-CoV-2 by administering to a subject a composition comprising an effective amount of AMB or BHH, or analogs or derivatives thereof, or a combination thereof, thereby inhibiting or ameliorating a SARS-CoV-2 infection.

Disclosed herein is a method of inhibiting or reducing viral entry into cells of a subject comprising administering to a subject a composition comprising an effective amount of AMB or BHH, or analogs or derivatives thereof, or a combination thereof, and inhibiting or disrupting the physical interaction of angiotensin converting enzyme 2 (ACE2) with the Spike (S) glycoprotein of SARS-CoV-2, thereby inhibiting or reducing viral entry into cells of the subject.

Disclosed herein is a method of inhibiting or reducing viral entry into cells of a subject comprising inhibiting or disrupting the physical interaction of angiotensin converting enzyme 2 (ACE2) with the Spike (S) glycoprotein of SARS-CoV-2 by administering to a subject a composition comprising an effective amount of AMB or BHH, or analogs or derivatives thereof, or a combination thereof, thereby inhibiting or reducing viral entry into cells of the subject.

Disclosed herein is a method comprising administering a composition comprising an effective amount AMB or BHH, or analogs or derivatives thereof, or a combination thereof; inhibiting or reducing the activity of a type II transmembrane serine protease; and inhibiting or disrupting the physical interaction of angiotensin converting enzyme 2 (ACE2) with the Spike (S) glycoprotein of SARS-CoV-2.

Disclosed herein is a method comprising inhibiting or reducing the activity of a type II transmembrane serine protease and inhibiting or disrupting the physical interaction of angiotensin converting enzyme 2 (ACE2) with the Spike (S) glycoprotein of SARS-CoV-2 by administering a composition comprising an effective amount of AMB or BHH, or analogs or derivatives thereof, or a combination thereof.

Disclosed herein is a method of inhibiting or disrupting the physical interaction of angiotensin converting enzyme 2 (ACE2) with the Spike (S) glycoprotein of SARS-CoV-2 comprising administering a composition comprising an effective amount of AMB or BHH, or analogs or derivatives thereof, or a combination thereof; and inhibiting or reducing the activity of a type II transmembrane serine protease, thereby inhibiting or disrupting the physical interaction of angiotensin converting enzyme 2 (ACE2).

Disclosed herein is a method of inhibiting or reducing viral infectivity in a subject comprising administering to a subject a composition comprising an effective amount of AMB or BHH, or analogs or derivatives thereof, or a combination thereof, or a combination thereof; inhibiting or reducing the activity of a type II transmembrane serine protease; and inhibiting or disrupting the physical interaction of angiotensin converting enzyme 2 (ACE2) with the Spike (S) glycoprotein of SARS-CoV-2, thereby inhibiting or reducing viral infectivity.

Disclosed herein is a method of inhibiting or reducing viral infectivity in a subject comprising inhibiting or reducing the activity of a type II transmembrane serine protease by administering to a subject a composition comprising an effective amount of AMB or BHH, or analogs or derivatives thereof, or a combination thereof, and inhibiting or disrupting the physical interaction of angiotensin converting enzyme 2 (ACE2) with the Spike (S) glycoprotein of SARS-CoV-2, thereby inhibiting or reducing viral infectivity.

Disclosed herein is a method of inhibiting or reducing a SARS-CoV-2 infection in a subject comprising administering to a subject a composition comprising an effective amount of AMB or BHH, or analogs or derivatives thereof, or a combination thereof, inhibiting or reducing the activity of a type II transmembrane serine protease; and inhibiting or disrupting the physical interaction of angiotensin converting enzyme 2 (ACE2) with the Spike (S) glycoprotein of SARS-CoV-2, thereby inhibiting or reducing a SARS-CoV-2 infection.

Disclosed herein is a method of inhibiting or reducing a SARS-CoV-2 infection in a subject comprising inhibiting or reducing the activity of a type II transmembrane serine protease and inhibiting or disrupting the physical interaction of angiotensin converting enzyme 2 (ACE2) with the Spike (S) glycoprotein of SARS-CoV-2 by administering to a subject a composition comprising an effective amount of AMB or BHH, or analogs or derivatives thereof, or a combination thereof, thereby inhibiting or reducing a SARS-CoV-2 infection.

Disclosed herein is a method of inhibiting or reducing viral entry into cells of a subject comprising administering to a subject a composition comprising an effective amount of AMB or BHH, or analogs or derivatives thereof, or a combination thereof; inhibiting or reducing the activity of a type II transmembrane serine protease; and inhibiting or disrupting the physical interaction of angiotensin converting enzyme 2 (ACE2) with the Spike (S) glycoprotein of SARS-CoV-2, thereby inhibiting or reducing viral entry into cells of the subject.

Disclosed herein is a method of inhibiting or reducing viral entry into cells of a subject comprising disrupting the physical interaction of angiotensin converting enzyme 2 (ACE2) with the Spike (S) glycoprotein of SARS-CoV-2 by administering to a subject a composition comprising an effective amount of AMB or BHH, or analogs or derivatives thereof, or a combination thereof, and inhibiting or reducing the activity of a type II transmembrane serine protease, thereby inhibiting or reducing viral entry into cells of the subject.

Disclosed herein is a composition comprising an effective amount of AMB or BHH, or analogs or derivatives thereof, or a combination thereof; and a pharmaceutically acceptable diluent, carrier, excipient, or stabilizer, wherein the composition inhibits or ameliorates a SARS-CoV-2 infection.

Disclosed herein is a composition comprising administering a composition comprising an effective amount of one or more compounds belonging to the benzylamine structural class; and a pharmaceutically acceptable diluent, carrier, excipient, or stabilizer, wherein the composition inhibits or ameliorates a SARS-CoV-2 infection.

Disclosed herein is a composition comprising an effective amount of AMB or BHH, or analogs or derivatives thereof, or a combination thereof; an effective amount of one or more clinically approved active agents; and a pharmaceutically acceptable diluent, carrier, excipient, or stabilizer, wherein the composition inhibits or ameliorates a SARS-CoV-2 infection.

Disclosed herein is a composition comprising administering a composition comprising an effective amount of one or more compounds belonging to the benzylamine structural class; an effective amount of one or more clinically approved active agents; and a pharmaceutically acceptable diluent, carrier, excipient, or stabilizer, wherein the composition inhibits or ameliorates a SARS-CoV-2 infection.

Disclosed herein is a composition comprising an effective amount of AMB or BHH, or analogs or derivatives thereof, or a combination thereof; and a pharmaceutically acceptable diluent, carrier, excipient, or stabilizer, wherein the composition inhibits or ameliorates one or more SARS-CoV-2 infection induced cytopathic effects.

Disclosed herein is a composition comprising an effective amount of AMB or BHH, or analogs or derivatives thereof, or a combination thereof; an effective amount of one or more anti-viral agents; and a pharmaceutically acceptable diluent, carrier, excipient, or stabilizer, wherein the composition inhibits or ameliorates one or more SARS-CoV-2 infection induced cytopathic effects.

Disclosed herein is a composition for inhibiting or ameliorating cytopathic effects in a subject comprising an effective amount of AMB, BHH, analogs or derivatives thereof, or a combination thereof; and a pharmaceutically acceptable diluent, carrier, excipient, or stabilizer, wherein the composition inhibits or ameliorates one or more cytopathic effects in a subject in need thereof.

Disclosed herein is a composition for inhibiting or ameliorating cytopathic effects in a subject comprising an effective amount of AMB or BHH, or analogs or derivatives thereof, or a combination thereof, an effective amount of one or more anti-viral agents; and a pharmaceutically acceptable diluent, carrier, excipient, or stabilizer, wherein the composition inhibits or ameliorates one or more cytopathic effects in a subject in need thereof.

Disclosed herein is a composition for inhibiting or ameliorating one or more SARS-CoV-2 infection induced cytopathic effects in a subject comprising an effective amount of AMB or BHH, or analogs or derivatives thereof, or a combination thereof; and a pharmaceutically acceptable diluent, carrier, excipient, or stabilizer, wherein the composition inhibits or ameliorates one or more cytopathic effects in a subject diagnosed with or suspected of having a SARS-CoV-2 infection.

Disclosed herein is a composition for inhibiting or ameliorating one or more SARS-CoV-2 infection induced cytopathic effects in a subject comprising an effective amount of AMB or BHH, or analogs or derivatives thereof, or a combination thereof, an effective amount of one or more anti-viral agents; and a pharmaceutically acceptable diluent, carrier, excipient, or stabilizer; wherein the composition inhibits or ameliorates one or more cytopathic effects in a subject diagnosed with or suspected of having a SARS-CoV-2 infection.

Disclosed herein is a composition for inhibiting or reducing exopeptidase activity of an enzyme comprising an effective amount of AMB or BHH, or analogs or derivatives thereof, or a combination thereof; and a pharmaceutically acceptable diluent, carrier, excipient, or stabilizer, wherein the composition inhibits or reduces the exopeptidase activity of angiotensin converting enzyme 2 (ACE2).

Disclosed herein is a composition for inhibiting or reducing exopeptidase activity of an enzyme comprising an effective amount of AMB or BHH, or analogs or derivatives thereof, or a combination thereof; and wherein the composition disrupts the physical interaction of angiotensin converting enzyme 2 (ACE2) with the Spike (S) glycoprotein of SARS-CoV-2, thereby inhibiting the exopeptidase activity of angiotensin converting enzyme 2 (ACE2).

Disclosed herein is a composition comprising an effective amount of AMB or BHH, or analogs or derivatives thereof, or a combination thereof, wherein the composition inhibits or disrupts the physical interaction of angiotensin converting enzyme 2 (ACE2) with the Spike (S) glycoprotein of SARS-CoV-2.

Disclosed herein is a composition for inhibiting or disrupting the physical interaction of angiotensin converting enzyme 2 (ACE2) with the Spike (S) glycoprotein of SARS-CoV-2 comprising an effective amount of AMB or BHH, or analogs or derivatives thereof, or a combination thereof.

Disclosed herein is a composition for inhibiting or reducing viral infectivity in a subject comprising an effective amount of AMB or BHH, or analogs or derivatives thereof, or a combination thereof, wherein the composition inhibits or disrupts the physical interaction of angiotensin converting enzyme 2 (ACE2) with the Spike (S) glycoprotein of SARS-CoV-2, thereby inhibiting or reducing viral infectivity.

Disclosed herein is a composition for inhibiting or ameliorating a SARS-CoV-2 infection in a subject comprising an effective amount of AMB or BHH, or analogs or derivatives thereof, or a combination thereof, wherein the composition inhibits or disrupts the physical interaction of angiotensin converting enzyme 2 (ACE2) with the Spike (S) glycoprotein of SARS-CoV-2, thereby inhibiting or ameliorating a SARS-CoV-2 infection.

Disclosed herein is a composition for inhibiting or reducing viral entry into cells of a subject comprising an effective amount of AMB or BHH, or analogs or derivatives thereof, or a combination thereof, and wherein the composition inhibits or disrupts they physical interactions of angiotensin converting enzyme 2 (ACE2) and the Spike (S) glycoprotein of SARS-CoV-2, thereby inhibiting or reducing viral entry into cells of the subject.

Disclosed herein is a composition comprising an effective amount of AMB or BHH, or analogs or derivatives thereof, or a combination thereof, wherein the composition inhibits or reduces the activity of a type II transmembrane serine protease, and wherein the composition inhibits or disrupts the physical interaction of angiotensin converting enzyme 2 (ACE2) with the Spike (S) glycoprotein of SARS-CoV-2.

Disclosed herein is a composition for inhibiting or disrupting the physical interaction of angiotensin converting enzyme 2 (ACE2) with the Spike (S) glycoprotein of SARS-CoV-2 comprising an effective amount of AMB or BHH, or analogs or derivatives thereof, or a combination thereof, whereby the composition inhibits or reduces the activity of a type II transmembrane serine protease.

Disclosed herein is a composition for inhibiting or reducing viral infectivity in a subject comprising an effective amount of AMB or BHH, or analogs or derivatives thereof, or a combination thereof, wherein the composition inhibits or reduces the activity of a type II transmembrane serine protease, and wherein the composition inhibits or disrupts the physical interaction of angiotensin converting enzyme 2 (ACE2) with the Spike (S) glycoprotein of SARS-CoV-2, thereby inhibiting or reducing viral infectivity.

Disclosed herein is a composition for inhibiting or ameliorating a SARS-CoV-2 infection in a subject comprising an effective amount of AMB or BHH, or analogs or derivatives thereof, or a combination thereof, wherein the composition inhibits or reduces the activity of a type II transmembrane serine protease, and wherein the composition inhibits or disrupts the physical interaction of angiotensin converting enzyme 2 (ACE2) with the Spike (S) glycoprotein of SARS-CoV-2, thereby inhibiting or ameliorating a SARS-CoV-2 infection.

Disclosed herein is a composition for inhibiting or reducing viral entry into cells of a subject comprising an effective amount of AMB or BHH, or analogs or derivatives thereof, or a combination thereof and wherein the composition inhibits or reduces the activity of a type II transmembrane serine protease, and wherein the composition inhibits or disrupts they physical interactions of angiotensin converting enzyme 2 (ACE2) and the Spike (S) glycoprotein of SARS-CoV-2, thereby inhibiting or reducing viral entry into cells of the subject.

VI. DETAILED DESCRIPTION

SARS-CoV-2 enters the host cells through two main pathways, both of which comprise key interactions between viral envelope-anchored Spike (S) glycoprotein of the novel coronavirus and the host angiotensin-converting enzyme 2 (ACE2) receptor, which is a membrane-bound metalloprotease.[98,100,105,107] ACE2 is a zinc metalloprotease and essential cellular receptor for SARS-CoV-2 entry into host cells. ACE2 is mainly expressed in alveolar epithelial cells of the lungs, heart, kidney, and gastrointestinal tract. ACE2 primarily functions as a carboxypeptidase that catalyzes the conversion of a single residue from angiotensin (Ang II), generating L-phenylalanine and Ang (1-7), a potent vasodilator, thus playing a role in controlling hypertension, renal disease, cardiac function, and lung injury. The crystalline structure of the ACE2 shows two domains: (i) a N-terminal zinc metallopeptidase domain (MPD) capable of binding the viral envelope-anchored Spike (S) glycoprotein of coronaviruses, and (ii) a C terminal "collectrin-like" domain.

The first pathway involves receptor mediated endocytosis. The second pathway involves cell fusion consisting of host receptor recognition and attachment of surface unit S1 to the peptidase domain of ACE2. The interaction of the MPD of ACE2 and S glycoprotein of SARS-CoV-2 is the initial and important step in viral infection by receptor recognition and fusion of host and viral cellular membranes.[98,100,105,108] In addition, viral entry requires priming of S protein by a host protease into S1 and S2 subunits, which are responsible for receptor attachment and membrane fusion, respectively,[35,41,89] A receptor-binding domain (RBD) of the S1 subunit specifically recognizes ACE2 on human cells.[98,100,105,108], Binding of the S1 subunit to ACE2 receptor triggers a conformational change in S glycoprotein from metastable pre-fusion state to stable post-fusion conformation, resulting in shedding of S1 and transition of the S2 subunit to expose a hydrophobic fusion peptide.[31,42,100], The initial priming at S1/S2 boundary by a plasma membrane-associated type II transmembrane serine protease (TMPRSS2) promotes subsequent cleavage at the S2 site by host proteases, which is important for membrane fusion and viral infectivity.[7,35,56,66,114] Therefore, targeting the interaction between human ACE2 receptor and the RBD in S protein of SARS-CoV-2 can be a promising approach for the development of effective entry inhibitors for potential prevention and/or treatment of COVID-19, thus providing possible countermeasures against viral entry, pathogenesis, and survival.

Clioquinol (5-chloro-7-iodo-8-quinolinol (CLQ)) and its derivatives belonging to the 8-hydroxyquinoline structural class have shown potent broad-spectrum activity against clinically relevant pathogens.[4,6,8,21,75,91,111], CLQ and its analogues have been extensively investigated as potential treatments for cancer and neurodegenerative diseases.[1,5,14,46,81,84,87,92] Additional studies have also shown the involvement of CLQ in the efflux mechanisms of ATP binding cassette (ABC) transporters[64,77] and the cellular autophagic pathway,[24,112] an important process in the host defense machinery against viral infections.[17] Furthermore, using a high-throughput screen (HTS) and chemical genomics approach, Olaleye et al. have identified and characterized CLQ and certain analogues as potent inhibitors of methionine aminopeptidase,[75] a universally conserved metalloprotease important for N-terminal methionine excision.[29,52] As an established metal chelator and zinc ionophore, CLQ modulates underlying molecular and physiologic machinery involved in metal homeostatis.[2,24,25,32,50,112] Altogether, these pharmacologic properties make CLQ an attractive drug for potential targeting of ACE2.

As described herein, the data evaluated the effect of CLQ and two of its analogues (7-bromo-5-chloro-8-hydroxyquinoline (CLBQ14) and 5,7-Dichloro-8-hydroxyquinoline (CLCQ)) on SARS-CoV-2 infection induced cytopathic effect (CPE) in vitro. The cytotoxicity of these compounds was also assessed. Furthermore, the impact of the three compounds on recombinant human ACE2 (rhACE2) interaction with the RBD on Spike protein of SARS-CoV-2 was examined. The effects of these three compounds on the exopeptidase activity of rhACE2 was also independently examined. These data show, for the first time, that CLQ, CLBQ14 and CLCQ effectively inhibits the novel SARS-CoV-2 infection induced CPE in vitro, inhibited rhACE2 and its interaction with Spike protein, and inhibited rhACE2 exopeptidase activity in the low micromolar range.

Belonging to the benzylamine structural class, Ambroxol hydrochloride ((AMB) 4-[(2-amino-3,5-dibromophenyl) methylamino]cyclohexan-1-ol; hydrochloride)[70] is a demethylated active metabolite of Bromhexine hydrochloride (BHH).[60] Both AMB and its progenitor BHH are used to treat respiratory tract infections and disorders[28,73,76,113], clinically indicated for their secretolytic activity for treatment of acute and chronic bronchopulmonary diseases associated with abnormal mucus secretion and impaired mucus transport[60,73,113] AMB and BHH have been available, affordable, and used as over the counter drugs with no significant adverse effects.[15,113] Furthermore, AMB and BHH have been investigated in translational studies because of their multiple activities including mucociliary clearance activity, mucokinetic properties, stimulation of surfactant production, anti-inflammatory and antioxidative actions, and the local anesthetic effect.[28,45,69,76,97], AMB and BHH have also been shown to induce cellular autophagic-lysosome pathway,[16,23,58] which are processes in the host defense machinery against viral infections.[17] AMB is reportedly involved in modulation of the homeostasis of ions such as hydrogen, calcium and sodium.[27] Due to its potential to act as a chaperone, pH-dependent, mixed-type inhibitor of glucocerebrosidase (GCase) and its involvement in mechanisms for mitochondria, lysosomal biogenesis, and secretory pathway,[27,57,58], AMB is being considered for the clinical development of therapeutics for neurodegenerative diseases.[57] Reports have also shown that AMB can inhibit viruses that cause influenza virus and rhinovirus infections.[106,109] In addition, AMB's progenitor BHH is a potent inhibitor of TMPRSS2[53], one of the proteases for viral fusion into host cells. BHH's activity against TMPRSS2 and lung protective properties makes it an attractive drug for the prevention and treatment of coronavirus infections.[59,86]

The effects of AMB and its progenitor BHH on the interaction between recombinant human ACE2 (ACE2) and the RBD on the S glycoprotein of SARS-CoV-2 are described herein. These data show the effect of both AMB and BHH on SARS-CoV-2 infection-induced cytopathic effect (CPE) in vitro. The cytotoxicity of AMB and BHH (as well as other clinically approved drugs) was also evaluated. AMB and BHH effectively modulated the ACE2's interaction with the Spike (RBD) protein in the micromolar range. At certain concentrations, both AMB and BHH inhibited SARS-CoV-2 infection-induced CPE. These data represent the first report that the AMB and the BHH pharmacophore have the capacity to target and modulate a protein-protein interaction involved in two known SARS-CoV-2 entry pathways. Altogether, the potent efficacy, stellar safety and pharmacologic profile of both drugs along with their affordability and availability, makes them promising candidates for drug repurposing as possible prophylactic and/or treatment options against SARS-CoV-2 infection.

The present disclosure describes dry formulations, compounded compositions, kits, capsules, containers, and/or methods thereof. It is to be understood that the inventive aspects of which are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention.

A. Definitions

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

This disclosure describes inventive concepts with reference to specific examples. However, the intent is to cover all modifications, equivalents, and alternatives of the inventive concepts that are consistent with this disclosure.

As used in the specification and the appended claims, the singular forms "a", "an", and "the" include plural referents unless the context clearly dictates otherwise.

The phrase "consisting essentially of" limits the scope of a claim to the recited components in a composition or the recited steps in a method as well as those that do not materially affect the basic and novel characteristic or characteristics of the claimed composition or claimed method. The phrase "consisting of" excludes any component, step, or element that is not recited in the claim. The phrase "comprising" is synonymous with "including", "containing", or "characterized by", and is inclusive or open-ended. "Comprising" does not exclude additional, unrecited components or steps.

As used herein, when referring to any numerical value, the term "about" means a value falling within a range that is +10% of the stated value.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight component X and 5 parts by weight component Y, X and Y are present at a weight ratio of 2:5, and are present in such ratio regardless of whether additional components are contained in the compound.

As used herein, the terms "optional" or "optionally" means that the subsequently described event or circumstance can or cannot occur, and that the description includes instances where said event or circumstance occurs and instances where it does not. In an aspect, a disclosed method can optionally comprise one or more additional steps, such as, for example, repeating an administering step or altering an administering step.

As used herein, the term "subject" refers to the target of administration, e.g., a human being. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig, or rodent. The term does not denote a particular age or sex, and thus, adult and child subjects, as well as fetuses, whether male or female, are intended to be covered. In an aspect, a subject can be a human patient. In an aspect, a subject can have a coronavirus infection, be suspected of having a coronavirus infection, or be at risk of developing a coronavirus infection. In an aspect, a coronavirus infection can comprise a SARS-CoV-2 infection. A subject can have a SARS-CoV-2 infection, be suspected of having a SARS-CoV-2 infection, or be at risk of developing a SARS-CoV-2 infection. For example, a subject at risk of developing a coronavirus infection can have, for example, risk factors for developing a coronavirus infection. Risk factors include, but are not limited to the following: cancer, chronic kidney disease, chronic obstructive pulmonary disease, an immunocompromised state (weakened immune system) from solid organ transplant, obesity (body mass index [BMI] of 30 or higher), serious heart conditions (e.g., heart failure, coronary artery disease, or cardiomyopathies), sickle cell disease, diabetes mellitus, asthma (moderate-to-severe), cerebrovascular disease (i.e., disease that affects blood vessels and blood supply to the brain), cystic fibrosis, hypertension or high blood pressure, immunocompromised state (weakened immune system) from blood or bone marrow transplant, immune deficiencies, HIV, use of corticosteroids, or use of other immune weakening medicines, neurologic conditions (e.g. dementia, Alzheimer's), liver disease, pregnancy, pulmonary fibrosis (having damaged or scarred lung tissues), tobacco use, smoking, thalassemia. A subject at risk for developing a coronavirus infection can be exposed to a coronavirus due to employment (e.g., a health care worker), attendance at a specific location (e.g., school), attendance at social events (e.g., sporting events, concerts, religious services, political rallies and events, social justice rallies, marches, and events, etc.), and/or by use of public transportation or public services. Exposure can happen in a subject's home as well.

As used herein, the term "diagnosed" means having been subjected to a physical examination by a person of skill, for example, a physician, and found to have a condition that can be diagnosed or treated by one or more of the disclosed compositions, a pharmaceutical preparation comprising one or more disclosed compositions to a subject, and/or disclosed methods. For example, "diagnosed with a coronavirus infection" means having been subjected to a physical examination by a person of skill, for example, a physician, and found to have a condition that can be treated by one or more of the disclosed compositions, a pharmaceutical preparation comprising one or more disclosed compositions to a subject, and/or disclosed methods. For example, "suspected of having a coronavirus infection" can mean having been subjected to a physical examination by a person of skill, for example, a physician, and found to have a condition that can likely be treated by one or more of the disclosed compositions, a pharmaceutical preparation comprising one or more disclosed compositions to a subject, and/or disclosed methods.

The words "treat" or "treating" or "treatment" refer to therapeutic or medical treatment wherein the object is to slow down (lessen), ameliorate, and/or diminish an undesired physiological change, disease, pathological condition, or disorder (for example, a SARS-CoV-2 infection or SARCoV-2 re-infection or a suspected SARS-CoV-2 infection or suspected SARS-CoV-2 re-infection) in a subject. As used herein, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Treatment may not necessarily result in the complete clearance of an infection but may reduce or minimize complications and side effects of infection and the progression of infection (such as, for example, a SARS-CoV-2 infection or re-infection). The success or otherwise of treatment may be monitored by physical examination of the subject as well as cytopathological, DNA, and/or mRNA detection techniques. The words "treat" or "treating" or "treatment" include palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the undesired physiological change, disease, pathological condition, or disorder from occurring in a subject that can be predisposed to the disease but has not yet been diagnosed as having it; (ii) inhibiting the physiological change, disease, pathological condition, or disorder, i.e., arresting its development; or (iii) relieving the physiological change, disease, pathological condition, or disorder, i.e., causing regression of the disease. For example, in an aspect, treating an infection can reduce the severity of an established infection in a subject by 1%-100% as compared to a control (such as, for example, a non-infected subject or a subject pre-SARS-CoV-2 infection). In an aspect, treating can refer to a 1%, 2%, 3%, 4%, 5%, 6%, 7%, 8%, 9%, 10%, 20%, 30%, 40%, 50%, 60%, 70%, 80%, 90%, or 100% reduction in the severity of an established coronavirus infection. For example, treating an infection can reduce one or more symptoms of an infection (including induced cytopathic effects) in a subject by 1%-100% as compared to a control (such as, for example, a non-infected subject or a subject pre-SARS-CoV-2 infection). In an aspect, treating can refer to 1%, 2%, 3%, 4%, 5%, 6%, 7%, 8%, 9%, 10%, 20%, 30%, 40%, 50%, 60%, 70%, 80%, 90%, 100% reduction of one or more symptoms (induced cytopathic effects) of an established coronavirus infection. It is understood that treatment does not necessarily refer to a cure or complete ablation or eradication of the coronavirus infection. However, in an aspect, treatment can refer to a cure or complete ablation or eradication of a coronavirus infection or re-infection.

A "patient" refers to a subject afflicted with a coronavirus. In an aspect, a patient can refer to a subject that has been diagnosed with or is suspected of having a coronavirus infection. In an aspect, a patient can refer to a subject that has been diagnosed with or is suspected of having a coronavirus infection and is seeking treatment or receiving treatment for the coronavirus infection. As used herein, the term "prevent" or "preventing" or "prevention" refers to precluding, averting, obviating, forestalling, stopping, or hindering something from happening, especially by advance action. It is understood that where reduce, inhibit, or prevent are used herein, unless specifically indicated otherwise, the use of the other two words is also expressly disclosed. In an aspect, preventing a coronavirus infection (e.g., a SARS-CoV-2 infection) is intended. The words "prevent" and "preventing" and "prevention" also refer to prophylactic or preventative measures for protecting or precluding a subject (e.g., an individual) not having a given infection related complication from progressing to that complication. Individuals in which prevention is required include those who have an infection.

As used herein, the terms "administering" and "administration" refer to any method of providing one or more of the disclosed compositions and/or a pharmaceutical preparation comprising one or more disclosed compositions to a subject to a subject. Such methods are well known to those skilled in the art and include, but are not limited to, the following: oral administration, transdermal administration, administration by inhalation, nasal administration, topical administration, intravaginal administration, ophthalmic administration, intraaural administration, otic administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent.

In various aspects, one or more of the disclosed compositions and/or a pharmaceutical preparation comprising one or more disclosed compositions can be administered therapeutically; that is, administered to treat an existing disease or condition. In further various aspects, one or more of the disclosed compositions and/or a pharmaceutical preparation comprising one or more disclosed compounds can be administered prophylactically; that is, administered for prevention of a disease or condition (e.g., a SARS-CoV-2 infection). In an aspect, the skilled person can determine an efficacious dose, an efficacious schedule, and an efficacious route of administration for one or more of the disclosed compounds and/or a pharmaceutical preparation comprising one or more disclosed compositions so as to treat or prevent an infection. In an aspect, the skilled person can also alter, change, or modify an aspect of an administering step to improve efficacy of one or more of the disclosed compositions and/or a pharmaceutical preparation comprising one or more disclosed compounds.

As used herein, "modifying the method" can comprise modifying or changing one or more features or aspects of one or more steps of a disclosed method. For example, in an aspect, a method can be altered by changing the amount of one or more of the disclosed compositions and/or a pharmaceutical preparation comprising one or more disclosed compositions administered to a subject, or by changing the frequency of administration of one or more of the disclosed compounds and/or a pharmaceutical preparation comprising one or more disclosed compositions to a subject, or by changing the duration of time one or more of the disclosed compounds and/or a pharmaceutical preparation comprising one or more disclosed compositions are administered to a subject.

As used herein, "concurrently" means (1) simultaneously in time, or (2) at different times during the course of a common treatment schedule.

The term "contacting" as used herein refers to bringing one or more of the disclosed compositions and/or a pharmaceutical preparation comprising one or more disclosed compositions together with a target area or intended target area in such a manner that the one or more of the disclosed compositions and/or a pharmaceutical preparation comprising one or more disclosed compositions can exert an effect on the intended target or targeted area either directly or indirectly. A target area or intended target area can be one or more of a subject's organs (e.g., lungs, heart, liver, kidney, etc.) In an aspect, a target area or intended target area can be any cell or any organ infected by SARS-CoV-2 or any cell or organ demonstrating one or more CPEs due to SARS-CoV-2.

As used herein, "determining" can refer to measuring or ascertaining the presence and severity of an infection, such as, for example, a coronavirus infection (e.g., a SARS-CoV-2). Methods and techniques used to determining the presence and/or severity of an infection are typically known to the medical arts. For example, the art is familiar with the ways to identify and/or diagnose the presence, severity, or both of a coronavirus infection such as SARS-CoV-2.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents, or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. In an aspect, a pharmaceutical carrier employed can be a solid, liquid, or gas. In an aspect, examples of solid carriers can include lactose, terra alba, sucrose, talc, gelatin, agar, pectin, acacia, magnesium stearate, and stearic acid. In an aspect, examples of liquid carriers can include sugar syrup, peanut oil, olive oil, and water. In an aspect, examples of gaseous carriers can include carbon dioxide and nitrogen. In preparing a disclosed composition for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions that are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "derivative" refers to a compound having a structure derived from the structure of a parent compound (e.g., a compound disclosed herein such as, for example, CLQ, CLBQ14, CLCQ, AMB, and BHH) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "analog" refers to a compound having a structure derived from the structure of a parent compound (e.g., a compound disclosed herein such as, for example, CLQ, CLBQ14, CLCQ, AMB, and BHH) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

As used herein, "effective amount" and "amount effective" can refer to an amount that is sufficient to achieve the desired result such as, for example, the treatment and/or prevention of a coronavirus infection (e.g., a SARS-CoV-2 infection) or a suspected coronavirus infection (e.g., a SARS-CoV-2 infection). As used herein, the terms "effective amount" and "amount effective" can refer to an amount that is sufficient to achieve the desired an effect on an undesired condition (e.g., a coronavirus infection). For example, a "therapeutically effective amount" refers to an amount that is sufficient to achieve the desired therapeutic result or to have an effect on undesired symptoms, but is generally insufficient to cause adverse side effects. In an aspect, "therapeutically effective amount" means an amount of a disclosed composition that (i) treats the particular disease, condition, or disorder (e.g., a coronavirus infection like SARS-CoV-2), (ii) attenuates, ameliorates, or eliminates one or more symptoms of the particular disease, condition, or disorder e.g., a coronavirus infection like SARS-CoV-2), or (iii) delays the onset of one or more symptoms of the particular disease, condition, or disorder described herein e.g., a coronavirus infection like SARS-CoV-2). The specific therapeutically effective dose level for any particular patient will depend upon a variety of factors including the disorder being treated and the severity of the disorder; the specific disclosed compositions and/or a pharmaceutical preparation comprising one or more disclosed compositions, or methods employed; the age, body weight, general health, sex and diet of the patient; the time of administration; the route of administration; the rate of excretion of the disclosed compositions and/or a pharmaceutical preparation comprising one or more disclosed compositions employed; the duration of the treatment; drugs used in combination or coincidental with a disclosed compositions and/or a pharmaceutical preparation comprising one or more disclosed compositions employed, and other like factors well known in the medical arts. For example, it is well within the skill of the art to start doses of a disclosed composition and/or a pharmaceutical preparation comprising one or more disclosed composition at levels lower than those required to achieve the desired therapeutic effect and to gradually increase the dosage until the desired effect is achieved. If desired, then the effective daily dose can be divided into multiple doses for purposes of administration. Consequently, a single dose of a disclosed compositions and/or a pharmaceutical preparation comprising one or more disclosed compositions, or methods can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition, such as, for example, a coronavirus infection (e.g., a SARS-CoV-2 infection).

Disclosed are the components to be used to prepare disclosed compositions and/or a pharmaceutical preparation comprising one or more disclosed compositions as well as the disclosed compositions and/or a pharmaceutical preparation comprising one or more disclosed compositions used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

B. Agents i. Biologically Active Agents

As used herein, the term "biologically active agent" or "biologic active agent" or "bioactive agent" means an agent that is capable of providing a local or systemic biological, physiological, or therapeutic effect in the biological system to which it is applied. For example, the bioactive agent can act to control infection or inflammation, enhance cell growth and tissue regeneration, control tumor growth, act as an analgesic, promote anti-cell attachment, and enhance bone growth, among other functions. Other suitable bioactive agents can include anti-viral agents, vaccines, hormones, antibodies (including active antibody fragments sFv, Fv, and Fab fragments), aptamers, peptide mimetics, functional nucleic acids, therapeutic proteins, peptides, or nucleic acids. Other bioactive agents include prodrugs, which are agents that are not biologically active when administered but, upon administration to a subject are converted to bioactive agents through metabolism or some other mechanism. Additionally, any of the compositions of the invention can contain combinations of two or more bioactive agents. It is understood that a biologically active agent can be used in connection with administration to various subjects, for example, to humans (i.e., medical administration) or to animals (i.e., veterinary administration). As used herein, the recitation of a biologically active agent inherently encompasses the pharmaceutically acceptable salts thereof.

ii. Pharmaceutically Active Agents

As used herein, the term "pharmaceutically active agent" includes a "drug" or a "vaccine" and means a molecule, group of molecules, complex or substance administered to an organism for diagnostic, therapeutic, preventative medical, or veterinary purposes. This term include externally and internally administered topical, localized and systemic human and animal pharmaceuticals, treatments, remedies, nutraceuticals, cosmeceuticals, biologicals, devices, diagnostics and contraceptives, including preparations useful in clinical and veterinary screening, prevention, prophylaxis, healing, wellness, detection, imaging, diagnosis, therapy, surgery, monitoring, cosmetics, prosthetics, forensics and the like. This term may also be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a bioactive effect, for example deoxyribonucleic acid (DNA) or ribonucleic acid (RNA). Pharmaceutically active agents include the herein disclosed categories and specific examples. It is not intended that the category be limited by the specific examples. Those of ordinary skill in the art will recognize also numerous other compounds that fall within the categories and that are useful according to the invention. Examples include a radiosensitizer, the combination of a radiosensitizer and a chemotherapeutic, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, carbonic anhydrase inhibitors, prostaglandin analogs, a combination of an alpha agonist and a beta blocker, a combination of a carbonic anhydrase inhibitor and a beta blocker, an anticholinergic/antispasmodic agent, a vasopressin analogue, an antiarrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifungal agent, or a vaccine. In a further aspect, the pharmaceutically active agent can be coumarin, albumin, bromolidine, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritis antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetominophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, timol hemihydrate, levobunolol hydrochloride, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists (i.e., alpha adrenergic receptor agonist) such as clonidine, brimonidine tartrate, and apraclonidine hydrochloride; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; prostaglandin analogs such as latanoprost, travoprost, and bimatoprost; cholinergics (i.e., acetylcholine receptor agonists) such as pilocarpine hydrochloride and carbachol; glutamate receptor agonists such as the N-methyl D-aspartate receptor agonist memantine; anti-Vascular endothelial growth factor (VEGF) aptamers such as pegaptanib; anti-VEGF antibodies (including but not limited to anti-VEGF-A antibodies) such as ranibizumab and bevacizumab; carbonic anhydrase inhibitors such as methazolamide, brinzolamide, dorzolamide hydrochloride, and acetazolamide; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and diisopyramide phosphate; antiparkinsonian agents, such as dopamine, L-Dopa/Carbidopa, selegiline, dihydroergocryptine, pergolide, lisuride, apomorphine, and bromocryptine; antiangina agents and antihypertensive agents such as isosorbide mononitrate, isosorbide dinitrate, propranolol, atenolol and verapamil; anticoagulant and antiplatelet agents such as coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHIRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hydrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides. It is understood that a pharmaceutically active agent can be used in connection with administration to various subjects, for example, to humans (i.e., medical administration) or to animals (i.e., veterinary administration). As used herein, the recitation of a pharmaceutically active agent inherently encompasses the pharmaceutically acceptable salts thereof.

iii. Anti-Bacterial Agents

As used herein, anti-bacterial agents are known to the art. For example, the art generally recognizes several categories of anti-bacterial agents including (1) penicillins, (2) cephalosporins, (3) quinolones, (4) aminoglycosides, (5) monobactams, (6) carbapenems, (7) macrolides, and (8) other agents. For example, as used herein, an anti-bacterial agent can comprise Afenide, Amikacin, Amoxicillin, Ampicillin, Arsphenamine, Augmentin, Azithromycin, Azlocillin, Aztreonam, Bacampicillin, Bacitracin, Balofloxacin, Besifloxacin, Capreomycin, Carbacephem (loracarbef), Carbenicillin, Cefacetrile (cephacetrile), Cefaclomezine, Cefaclor, Cefadroxil (cefadroxyl), Cefalexin (cephalexin), Cefaloglycin (cephaloglycin), Cefalonium (cephalonium), Cefaloram, Cefaloridine (cephaloradine), Cefalotin (cephalothin), Cefamandole, Cefaparole, Cefapirin (cephapirin), Cefatrizine, Cefazaflur, Cefazedone, Cefazolin (cephazolin), Cefcanel, Cefcapene, Cefclidine, Cefdaloxime, Cefdinir, Cefditoren, Cefedrolor, Cefempidone, Cefepime, Cefetamet, Cefetrizole, Cefivitril, Cefixime, Cefluprenam, Cefmatilen, Cefmenoxime, Cefmepidium, Cefmetazole, Cefodizime, Cefonicid, Cefoperazone, Cefoselis, Cefotaxime, Cefotetan, Cefovecin, Cefoxazole, Cefoxitin, Cefozopran, Cefpimizole, Cefpirome, Cefpodoxime, Cefprozil (cefproxil), Cefquinome, Cefradine (cephradine), Cefrotil, Cefroxadine, Cefsumide, Ceftaroline, Ceftazidime, Ceftazidime/Avibactam, Cefteram, Ceftezole, Ceftibuten, Ceftiofur, Ceftiolene, Ceftioxide, Ceftizoxime, Ceftobiprole, Ceftriaxone, Cefuracetime, Cefuroxime, Cefuzonam, Cephalexin, Chloramphenicol, Chlorhexidine, Ciprofloxacin, Clarithromycin, Clavulanic Acid, Clinafloxacin, Clindamycin, Cloxacillin, Colimycin, Colistimethate, Colistin, Crysticillin, Cycloserine 2, Demeclocycline, Dicloxacillin, Dirithromycin, Doripenem, Doxycycline, Efprozil, Enoxacin, Ertapenem, Erythromycin, Ethambutol, Flucloxacillin, Flumequine, Fosfomycin, Furazolidone, Gatifloxacin, Geldanamycin, Gemifloxacin, Gentamicin, Glycopeptides, Grepafloxacin, Herbimycin, Imipenem, Isoniazid, Kanamycin, Levofloxacin, Lincomycin, Linezolid, Lipoglycopeptides, Lomefloxacin, Meropenem, Meticillin, Metronidazole, Mezlocillin, Minocycline, Mitomycin, Moxifloxacin, Mupirocin, Nadifloxacin, Nafcillin, Nalidixic Acid, Neomycin, Netilmicin, Nitrofurantoin, Norfloxacin, Ofloxacin, Oxacillin, Oxazolidinones, Oxolinic Acid, Oxytetracycline, Oxytetracycline, Paromomycin, Pazufloxacin, Pefloxacin, Penicillin G, Penicillin V, Pipemidic Acid, Piperacillin, Piromidic Acid, Pivampicillin, Pivmecillinam, Platensimycin, Polymyxin B, Pristinamycin, Prontosil, Prulifloxacin, Pvampicillin, Pyrazinamide, Quinupristin/dalfopristin, Rifabutin, Rifalazil, Rifampin, Rifamycin, Rifapentine, Rosoxacin, Roxithromycin, Rufloxacin, Sitafloxacin, Sparfloxacin, Spectinomycin, Spiramycin, Streptomycin, Sulbactam, Sulfacetamide, Sulfamethizole, Sulfamethoxazole, Sulfanilimide, Sulfisoxazole, Sulphonamides, Sultamicillin, Teicoplanin, Telavancin, Telithromycin, Temafloxacin, Tetracycline, Thiamphenicol, Ticarcillin, Tigecycline, Tinidazole, Tobramycin, Tosufloxacin, Trimethoprim, Trimethoprim-Sulfamethoxazole, Troleandomycin, Trovafloxacin, Tuberactinomycin, Vancomycin, Viomycin, or pharmaceutically acceptable salts thereof (e.g., such as, for example, chloride, bromide, iodide, and periodate), or a combination thereof. As used herein, the recitation of an anti-bacterial agent inherently encompasses the pharmaceutically acceptable salts thereof.

iv. Anti-Fungal Agents

Anti-fungal agents are known to the art. The art generally recognizes several categories of anti-fungal agents including (1) azoles (imidazoles), (2) antimetabolites, (3) allylamines, (4) morpholine, (5) glucan synthesis inhibitors (echinocandins), (6) polyenes, (7) benoxaaborale; (8) other antifungal/onychomycosis agents, and (9) new classes of antifungal/onychomycosis agents. For example, as used herein, an anti-fungal agent can comprise Abafungin, Albaconazole, Amorolfin, Amphotericin B, Anidulafungin, Bifonazole, Butenafine, Butoconazole, Candicidin, Caspofungin, Ciclopirox, Clotrimazole, Econazole, Fenticonazole, Filipin, Fluconazole, Flucytosine, Griseofulvin, Haloprogin, Hamycin, Isavuconazole, Isoconazole, Itraconazole, Ketoconazole, Micafungin, Miconazole, Naftifine, Natamycin, Nystatin, Omoconazole, Oxiconazole, Polygodial, Posaconazole, Ravuconazole, Rimocidin, Sertaconazole, Sulconazole, Terbinafine, Terconazole, Tioconazole, Tolnaftate, Undecylenic Acid, Voriconazole, or pharmaceutically acceptable salts thereof, or a combination thereof. In an aspect, an anti-fungal agent can be an azole. Azoles include, but are not limited to, the following: clotrimazole, econazole, fluconazole, itraconazole, ketoconazole, miconazole, oxiconazole, sulconazole, and voriconazole. As used herein, the recitation of an anti-fungal agent inherently encompasses the pharmaceutically acceptable salts thereof.

v. Anti-Viral Agents

Anti-viral agents are known to the art. As used herein, for example, an anti-viral can comprise Abacavir, Acyclovir (Aciclovir), Adefovir, Amantadine, Ampligen, Amprenavir (Agenerase), Umifenovir (Arbidol), Atazanavir, Atripla, Baloxavir marboxil (Xofluza), Biktarvy, Boceprevir, Bulevirtide, Cidofovir, Cobicistat (Tybost), Combivir, Daclatasvir (Daklinza), Darunavir, Delavirdine, Descovy, Didanosine, Docosanol, Dolutegravir, Doravirine (Pifeltro), Edoxudine, Efavirenz, Elvitegravir, Emtricitabine, Enfuvirtide, Entecavir, Etravirine (Intelence), Famciclovir, Fomivirsen, Fosamprenavir, Foscarnet, Ganciclovir (Cytovene), Ibacitabine, Ibalizumab (Trogarzo), Idoxuridine, Imiquimod, Imunovir, Indinavir, Lamivudine, Letermovir (Prevymis), Lopinavir, Loviride, Maraviroc, Methisazone, Moroxydine, Nelfinavir, Nevirapine, Nexavir (formerly Kutapressin), Nitazoxanide, Norvir, Oseltamivir (Tamiflu), Penciclovir, Peramivir, Penciclovir, Peramivir (Rapivab), Pleconaril, Podophyllotoxin, Raltegravir, Remdesivir, Ribavirin, Rilpivirine (Edurant), Rilpivirine, Rimantadine, Ritonavir, Saquinavir, Simeprevir (Olysio), Sofosbuvir, Stavudine, Taribavirin (Viramidine), Telaprevir, Telbivudine (Tyzeka), Tenofovir alafenamide, Tenofovir disoproxil, Tenofovir, Tipranavir, Trifluridine, Trizivir, Tromantadine, Truvada, Umifenovirk, Valaciclovir, Valganciclovir (Valtrex), Vicriviroc, Vidarabine, Zalcitabine, Zanamivir (Relenza), Zidovudine, and combinations thereof. As used herein, the recitation of any anti-viral agent inherently encompasses the pharmaceutically acceptable salts thereof.

vi. Corticosteroids Corticosteroids are well-known in the art. Corticosteroids mimic the effects of hormones that the body produces naturally in your adrenal glands. Corticosteroids can suppress inflammation and can reduce the signs and symptoms of inflammatory conditions (e.g., arthritis and asthma). Corticosteroids can also suppress the immune system. Corticosteroids can act on a number of different cells (e.g., mast cells, neutrophils, macrophages and lymphocytes) and a number of different mediators (e.g., histamine, leukotriene, and cytokine subtypes).

Steroids include, but are not limited to, the following: triamcinolone and its derivatives (e.g., diacetate, hexacetonide, and acetonide), betamethasone and its derivatives (e.g., dipropionate, benzoate, sodium phosphate, acetate, and valerate), dexamethasone and its derivatives (e.g., dipropionate and valerate), flunisolide, prednisone and its derivatives (e.g., acetate), prednisolone and its derivatives (e.g., acetate, sodium phosphate, and tebutate), methylprednisolone and its derivatives (e.g., acetate and sodium succinate), fluocinolone and its derivatives (e.g., acetonide), diflorasone and its derivatives (e.g., diacetate), halcinonide, desoximetasone (desoxymethasone), diflucortolone and its derivatives (e.g., valerate), flucloronide (fluclorolone acetonide), fluocinonide, fluocortolone, fluprednidene and its derivatives (e.g., acetate), flurandrenolide (flurandrenolone), clobetasol and its derivatives (e.g., propionate), clobetasone and its derivatives (e.g., butyrate), alclometasone, flumethasone and its derivatives (e.g., pivalate), fluocortolone and its derivatives (e.g., hexanoate), amcinonide, beclometasone and its derivatives (e.g., dipropionate), fluticasone and its derivatives (e.g., propionate), difluprednate, prednicarbate, flurandrenolide, mometasone, and desonide. As used herein, the recitation of a corticosteroid inherently encompasses the pharmaceutically acceptable salts thereof.

vii. Analgesics

The compositions of the present disclosure can also be used in combination therapies with opioids and other analgesics, including narcotic analgesics, Mu receptor antagonists, Kappa receptor antagonists, non-narcotic (i.e., non-addictive) analgesics, monoamine uptake inhibitors, adenosine regulating agents, cannabinoid derivatives, Substance P antagonists, neurokinin-1 receptor antagonists and sodium channel blockers, among others. Preferred combination therapies comprise a composition useful in methods described herein with one or more compounds selected from aceclofenac, acemetacin, .alpha.-acetamidocaproic acid, acetaminophen, acetaminosalol, acetanilide, acetylsalicylic acid (aspirin), S-adenosylmethionine, alclofenac, alfentanil, allylprodine, alminoprofen, aloxiprin, alphaprodine, aluminum bis (acetylsalicylate), amfenac, aminochlorthenoxazin, 3-amino-4-hydroxybutyric acid, 2-atnino-4-picoline, aminopropylon, aminopyrine, amixetrine, ammonium salicylate, ampiroxicam, amtolmetin guacil, anileridine, antipyrine, antipyrine salicylate, antrafenine, apazone, bendazac, benorylate, benoxaprofen, benzpiperylon, benzydamine, benzylmorphine, bermoprofen, bezitramide, .alpha.-bisabolol, bromfenac, p-bromoacetanilide, 5-bromosalicylic acid acetate, bromosaligenin, bucetin, bucloxic acid, bucolome, bufexamac, bumadizon, buprenorphine, butacetin, butibufen, butophanol, calcium acetylsalicylate, carbamazepine, carbiphene, carprofen, carsalam, chlorobutanol, chlorthenoxazin, choline salicylate, cinchophen, cinmetacin, ciramadol, clidanac, clometacin, clonitazene, clonixin, clopirac, clove, codeine, codeine methyl bromide, codeine phosphate, codeine sulfate, cropropamide, crotethamide, desomorphine, dexoxadrol, dextromoramide, dezocine, diampromide, diclofenac sodium, difenamizole, difenpiramide, diflunisal, dihydrocodeine, dihydrocodeinone enol acetate, dihydromorphine, dihydroxyalutninum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, flufenamic acid, flunoxaprofen, fluoresone, flupirtine, fluproquazone, flurbiprofen, fosfosal, gentisic acid, glafenine, glucametacin, glycol salicylate, guaiazulene, hydrocodone, hydromorphone, hydroxypethidine, ibufenac, ibuprofen, ibuproxam, imidazole salicylate, indomethacin, indoprofen, isofezolac, isoladol, isomethadone, isonixin, isoxepac, isoxicam, ketobemidone, ketoprofen, ketorolac, p-lactophenetide, lefetamine, levorphanol, lofentanil, lonazolac, lomoxicam, loxoprofen, lysine acetylsalicylate, magnesium acetylsalicylate, meclofenamic acid, mefenamic acid, meperidine, meptazinol, mesalamine, metazocine, methadone hydrochloride, methotrimeprazine, metiazinic acid, metofoline, metopon, mofebutazone, mofezolac, morazone, morphine, morphine hydrochloride, morphine sulfate, morpholine salicylate, myrophine, nabumetone, nalbuphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paranyline, parsalmide, pentazocine, perisoxal, phenacetin, phenadoxone, phenazocine, phenazopyridine hydrochloride, phenocoll, phenoperidine, phenopyrazone, phenyl acetylsalicylate, phenylbutazone, phenyl salicylate, phenyramidol, piketoprofen, piminodine, pipebuzone, piperylone, piprofen, pirazolac, piritramide, piroxicam, pranoprofen, proglumetacin, proheptazine, promedol, propacetamol, propiram, propoxyphene, propyphenazone, proquazone, protizinic acid, ramifenazone, remifentanil, rimazolium metilsulfate, salacetamide, salicin, salicylamide, salicylamide o-acetic acid, salicylsulfuric acid, salsalte, salverine, simetride, sodium salicylate, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tolfenamic acid, tolmetin, tramadol, tropesin, viminol, xenbucin, ximoprofen, zaltoprofen and zomepirac. Analgesics are well known in the art. See, for example, The Merck Index, 12th Edition (1996), Therapeutic Category and Biological Activity Index, and the lists provided under "Analgesic", "Anti-inflammatory" and "Antipyretic". As used herein, the recitation of an analgesic inherently encompasses the pharmaceutically acceptable salts thereof.

viii. Immunostimulants

The term "immunostimulant" is used herein to describe a substance which evokes, increases, and/or prolongs an immune response to an antigen. Immunomodulatory agents modulate the immune system, and, as used herein, immunostimulants are also referred to as immunomodulatory agents, where it is understood that the desired modulation is to stimulate the immune system. There are two main categories of immunostimulants, specific and non-specific. Specific immunostimulants provide antigenic specificity in immune response, such as vaccines or any antigen, and non-specific immunostimulants act irrespective of antigenic specificity to augment immune response of other antigen or stimulate components of the immune system without antigenic specificity, such as adjuvants and non-specific immunostimulators. Immunostimulants can include, but are not limited to, levamisole, thalidomide, erythema nodosum leprosum, BCG, cytokines such as interleukins or interferons, including recombinant cytokines and interleukin 2 (aldeslukin), 3D-MPL, QS21, CpG ODN 7909, miltefosine, anti-PD-1 or PD-1 targeting drugs, and acid (DCA, a macrophage stimulator), imiquimod and resiquimod (which activate immune cells through the toll-like receptor 7), chlorooxygen compounds such as tetrachlorodecaoxide (TCDO), agonistic CD40 antibodies, soluble CD40L, 4-1BB:4-1BBL agonists, OX40 agonists, TLR agonists, moieties that deplete regulatory T cells, arabinitol-ceramide, glycerol-ceramide, 6-deoxy and 6-sulfono-myo-insitolceramide, iNKT agonists, and TLR agonists. As used herein, the recitation of an immunostimulant inherently encompasses the pharmaceutically acceptable salts thereof.

ix. Immune-Based Product

As used herein, immune-based products include, but are not limited to, toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 agonists; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107, interleukin-15/Fc fusion protein, normferon, peginterferon alfa-2a, peginterferon alfa-2b, recombinant interleukin-15, RPI-MN, GS-9620, and IR-103. As used herein, the recitation of an immune-based product inherently encompasses the pharmaceutically acceptable salts thereof.

x. Blood Derived Products

As used herein, blood-derived products are obtained from subjects that have recovered from a SARS-CoV-2 infection and include convalescent plasma, immunoglobulin products, and neutralizing monoclonal antibodies.

C. 8-Hydroxyquinoline Structural Class

1. Methods Comprising 8-Hydroxyquinoline Structural Class

General Methods

Disclosed herein is a method comprising administering a composition comprising an effective amount of one or more compounds belonging to the 8-hydroxyquinoline structural class; and inhibiting or ameliorating a SARS-CoV-2 infection. Disclosed herein is a method comprising administering a composition comprising an effective amount of CLQ, CLBQ14, or CLCQ, or analogs or derivatives thereof, or a combination thereof, and inhibiting or ameliorating a SARS-CoV-2 infection. Disclosed herein is a method comprising administering a composition comprising an effective amount of one or more compounds belonging to the 8-hydroxyquinoline structural class; administering one or more clinically approved active agents; and inhibiting or ameliorating a SARS-CoV-2 infection. Disclosed herein is a method comprising administering a composition comprising an effective amount of CLQ, CLBQ14, or CLCQ, or analogs or derivatives thereof, or a combination thereof; administering one or more clinically approved active agents; and inhibiting or ameliorating a SARS-CoV-2 infection. Disclosed herein is a method comprising inhibiting or ameliorating a SARS-CoV-2 infection by administering a composition comprising one or more compounds belonging to the 8-hydroxyquinoline structural class. Disclosed herein is a method comprising inhibiting or ameliorating a SARS-CoV-2 infection by administering a composition comprising an effective amount of CLQ, CLBQ14, or CLCQ, or analogs or derivatives thereof, or a combination thereof. Disclosed herein is a method of inhibiting or ameliorating a SARS-CoV-2 infection comprising administering a composition comprising an effective amount of one or more compounds belonging to the 8-hydroxyquinoline structural class, thereby inhibiting or ameliorating a SARS-CoV-2 infection. Disclosed herein is a method of inhibiting or ameliorating a SARS-CoV-2 infection comprising administering a composition comprising an effective amount of CLQ, CLBQ14, or CLCQ, or analogs or derivatives thereof, or a combination thereof, thereby inhibiting or ameliorating a SARS-CoV-2 infection. Disclosed herein is a method of inhibiting or ameliorating a SARS-CoV-2 infection comprising administering a composition comprising an effective amount of one or more compounds belonging to the 8-hydroxyquinoline structural class; and inhibiting or ameliorating a SARS-CoV-2 infection. Disclosed herein is a method of inhibiting or ameliorating a SARS-CoV-2 infection comprising administering a composition comprising an effective amount of CLQ, CLBQ14, or CLCQ, or analogs or derivatives thereof, or a combination thereof, and inhibiting or ameliorating a SARS-CoV-2 infection. Disclosed herein is a method of inhibiting or ameliorating a SARS-CoV-2 infection comprising prophylactically administering a composition comprising an effective amount of one or more compounds belonging to the 8-hydroxyquinoline structural class; and inhibiting or ameliorating a SARS-CoV-2 infection. Disclosed herein is a method of inhibiting or ameliorating a SARS-CoV-2 infection comprising prophylactically administering a composition comprising an effective amount of CLQ, CLBQ14, or CLCQ, or analogs or derivatives thereof, or a combination thereof, and inhibiting or ameliorating a SARS-CoV-2 infection.

The 8-hydroxyquinoline structural class is known to the art. For example, 8-hydroxyquinoline (Quinolin-8-ol) comprises the formula $C_{18}H_{12}CuN_2O_2$ or $C_9H_7NO$ and has a molecular weight of 145.16 g/mol. 8-hydroxyquinoline is a monohydroxyquinoline comprising a quinoline substituted by a hydroxy group at position 8. The 8-hydroxyquinoline structural class comprises at least CLQ, CLBQ14, and CLCQ. 5-chloro-7-iodoquinolin-8-ol (Clioquinol or CLQ) comprises the formula $C_9H_5ClINO$ and has a molecular weight of 305.5 g/mol. 5-chloro-7-iodoquinolin-8-ol is a monohydroxyquinoline that is a quinolin-8-ol in which the hydrogens at positions 5 and 7 are replaced by chlorine and iodine, respectively. 7-bromo-5-chloro-8-hydroxyquinoline (CLBQ14) comprises the formula $C_9H_5BrClNO$ and has a molecular weight of 258.5 g/mol. 7-bromo-5-chloro-8-hydroxyquinoline is a monohydroxyquinoline that is a quinolin-8-ol in which the hydrogens at positions 5 and 7 are replaced by chlorine and bromine, respectively. 5,7-dichloro-8-hydroxyquinoline (CLCQ) comprise the formula $C_9H_5Cl_2NO$ and has a molecular weight of 214.04 g/mol. 5,7-Dichloro-8-hydroxyquinoline (CLCQ) is a monohydroxyquinoline that is a quinolin-8-ol in which the hydrogens at positions 5 and 7 have been substituted by chlorine.

In an aspect, a disclosed method or a disclosed method of inhibiting or ameliorating a SARS-CoV-2 infection can comprise administering one or more active agents, one or more biologically active agents, one or more pharmaceutically active agents, one or more immune-based therapeutic agents, one or more clinically approved agents, or a combination thereof. Biologically active agents are described herein and are known to the art. Pharmaceutically active agents are described herein and are known to the art. Immune-based therapeutic agents are described herein and are known to the art. Clinically approved active agents can comprise one or more FDA-approved active agents regardless of whether an active agent is a biologically active agent, a pharmaceutically active agent, or an immune-based therapeutic agent.

In an aspect, a disclosed composition in a disclosed method or a disclosed method of inhibiting or ameliorating a SARS-CoV-2 infection can comprise (i) one or more active agents, (ii) one or more biologically active agents, (iii) one or more pharmaceutically active agents, (iv) one or more immune-based therapeutic agents, (v) one or more clinically approved agents, or (vi) a combination thereof. In an aspect, a disclosed method or a disclosed method of inhibiting or ameliorating a SARS-CoV-2 infection can comprise administering (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof. In an aspect, a disclosed composition in a disclosed method or a disclosed method of inhibiting or ameliorating a SARS-CoV-2 infection can comprise (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof.

In an aspect, a composition in a disclosed method or a disclosed method of inhibiting or ameliorating a SARS-CoV-2 infection may comprise CLQ, CLBQ14, and/or CLCQ, or analogs or derivatives thereof, or a combination thereof. The composition may be administered in various formats, such as tablet, capsule, syrup, dry powder sachets, inhalation solution/nebulization, drops, ampules, suppository, creams or ointments. For example, the composition may be administered in a tablet format. Tablets may be formulated for controlled release formulation, delayed release formulation, extended release formulation, sustained release formulation, pulsatile release formulation, or mixed immediate release formulation. Tablets may be effervescent. The composition may be administered in a capsule format. Capsules may be formulated for immediate release or sustained release, as examples. Capsules may be hard capsules or and soft capsules. Solution formats may be oil based, aqueous, or emulsions.

In various embodiments, the composition comprising CLQ, CLBQ14, and/or CLCQ, or analogs or derivatives thereof, or a combination thereof, may be administered via any suitable administration route. Example administration routes include parenteral administration, which may include intramuscular, intraarterial, or intravenous, as examples. Example administration routes include nonparenteral administration, such as oral, rectal, vaginal, nasal, mucosal, percutaneous, transdermal, or ophthalmic, as examples.

The composition comprising CLQ, CLBQ14, and/or CLCQ, or analogs or derivatives thereof, or a combination thereof, may be administered in a suitable dosage format, via a suitable route of administration, such as any of those identified above, and in an effective daily dose to inhibit or ameliorate a SARS-CoV-2 infection, such as by any mechanism identified herein. The daily dose may be between 30 mg up to 2,000 mg. Example daily dosages may include greater than 200 mg, greater than 400 mg, greater than 500 mg, greater than 600 mg, greater than 700 mg, greater than 800 mg, greater than 900 mg, greater than 1000 mg, between 50 mg and 100 mg, between 100 mg and 200 mg, between 150 mg and 300 mg, between 200 mg and 1000 mg, between 500 mg and 1500 mg, between 450 mg and 1200 mg, between 500 mg and 2000 mg, between 1000 mg and 2000 mg, or any range between 30 mg and 2000 mg. The composition will typically be administered once daily, twice daily, or three times daily; however, additional administrations may be used.

In an aspect, a disclosed method or a disclosed method of inhibiting or ameliorating a SARS-CoV-2 infection can comprise repeating one or more steps.

In an aspect, a disclosed method or a disclosed method of inhibiting or ameliorating a SARS-CoV-2 infection can comprise identifying a subject having been diagnosed with or suspected of having a SARS-CoV-2 infection. As known to the art, a SARS-CoV-2 infection can be diagnosed and/or confirmed through various tests (such as, e.g., a PCR test or an antigen test).

In an aspect, a disclosed method or a disclosed method of inhibiting or ameliorating a SARS-CoV-2 infection can comprise identifying a subject having been diagnosed with or suspected of having a SARS-CoV-2 re-infection. As known to the art, a past SARS-CoV-2 infection can be diagnosed and/or confirmed through an antibody test. In an aspect, an antibody test (also known as serology testing) can check for Immunoglobulin G (IgG) antibody. In an aspect, a variety of factors can impact the results from an antibody test in a disclosed method (e.g., the time the test was taken after experiencing symptoms, the absence of or time since exposure to the virus, or the lack of an adequate immune response, which can be due to conditions or treatments that suppress immune function).

In an aspect, the administering step of a disclosed method or a disclosed method of inhibiting or ameliorating a SARS-CoV-2 infection can comprise administering to a subject. In an aspect, a subject can be a human. In an aspect, a human subject can be a participant in a clinical trial. In an aspect, a subject can be a human or a non-human primate diagnosed with or suspected of having a SARS-CoV-2 infection.

In an aspect, a disclosed method or a disclosed method of inhibiting or ameliorating a SARS-CoV-2 infection can comprise identifying and/or characterizing one or more comorbidities in a subject. In an aspect, a subject can have one or more comorbidities. Comorbidities are known to the art and can comprise cancer, chronic kidney disease, COPD (chronic obstructive pulmonary disease), an immunocompromised state (weakened immune system) from a solid organ transplant or from a blood or bone marrow transplant, obesity (body mass index [BMI] of 30 or higher), heart conditions (such as, e.g., heart failure, coronary artery disease, or cardiomyopathies), sickle cell disease, type 1 diabetes mellitus or type 2 diabetes mellitus, asthma, cerebrovascular disease, cystic fibrosis, hypertension or high blood pressure, immune deficiencies, HIV, use of corticosteroids, or use of other immune weakening medicines, neurologic conditions, liver disease, pregnancy, pulmonary fibrosis (having damaged or scarred lung tissues), a history of smoking, and thalassemia (a type of blood disorder).

In an aspect, a disclosed method or a disclosed method of inhibiting or ameliorating a SARS-CoV-2 infection can comprise treating or ameliorating one or more comorbidities in a subject. For example, in an aspect, a disclosed method or a disclosed method of inhibiting or ameliorating a SARS-CoV-2 infection can comprise (i) administering one or more active agents to treat or ameliorate one or more comorbidities, (ii) administering one or more active agents to treat or ameliorate the same comorbidity, (iii) administering one or more active agents to treat or ameliorate different comorbidities (e.g., an active agent for type 2 diabetes and a different active agent for hypertension), or (iv) a combination thereof. In an aspect, administering an active agent to treat or ameliorate one or more comorbidities can occur prior to, concurrently with, or after the administering of a disclosed composition. In an aspect, a disclosed method or a disclosed method of inhibiting or ameliorating a SARS-CoV-2 infection can comprise repeating the administering step of an active agent to treat or ameliorate one or more comorbidities.

In an aspect, a disclosed method or a disclosed method of inhibiting or ameliorating a SARS-CoV-2 infection can comprise modifying or altering one or more steps of a disclosed method. For example, in an aspect, a disclosed method or a disclosed method of inhibiting or ameliorating a SARS-CoV-2 infection can comprise modifying or altering an administering step. In an aspect, an administering step can be modified or altered, for example, by changing the route of administration, or changing the dose of a disclosed composition, or changing the timing of administration, or changing the frequency of the administration, or a combination thereof.

In an aspect, altering or modifying one or more steps of a disclosed method or a disclosed method of inhibiting or ameliorating a SARS-CoV-2 infection can be based on the identification and/or characterization of one or more comorbidities in a subject.

In an aspect, a disclosed method or a disclosed method of inhibiting or ameliorating a SARS-CoV-2 infection can comprise modifying or altering the administering step of an active agent to treat or ameliorate one or more comorbidities.

In an aspect, a disclosed method or a disclosed method of inhibiting or ameliorating a SARS-CoV-2 infection can comprise determining, measuring, and/or ascertaining the presence and/or severity of an infection, such as, for example, a SARS-CoV-2 infection, a bacterial infection, a viral infection, a fungal infection, or a combination thereof. Methods and techniques used to determine, measure, and/or ascertain the presence and/or severity of an infection such as a SARS-CoV-2 infection are typically known to the medical arts.

In an aspect, a disclosed method or a disclosed method of inhibiting or ameliorating a SARS-CoV-2 infection can comprise monitoring a subject's response to the administration of a disclosed composition comprising CLQ, CLBQ14, or CLCQ, or analogs or derivatives thereof, or a combination thereof. In an aspect of a disclosed method, a monitoring step can be repeated one or more times.

In an aspect, a disclosed method or a disclosed method of inhibiting or ameliorating a SARS-CoV-2 infection can comprise monitoring a subject's response to the administration of a disclosed composition comprising (i) CLQ, CLBQ14, or CLCQ, or analogs or derivatives thereof, or a combination thereof and (ii) one or more disclosed active agents, one or more biologically active agents, one or more pharmaceutically active agents, one or more immune-based therapeutic agents, one or more clinically approved agents, or a combination thereof. In an aspect of a disclosed method, a monitoring step can be repeated one or more times.

Methods and techniques to monitor a subject's response to a disclosed method can comprise qualitative (or subjective) means as well as quantitative (or objective) means. In an aspect, qualitative means (or subjective means) can comprise a subject's own perspective. For example, a subject can report how he/she is feeling, whether he/she has experienced improvements and/or setbacks, whether he/she has experienced an amelioration or an intensification of one or more symptoms, or a combination thereof. In an aspect, quantitative means (or objective means) can comprise methods and techniques that include, but are not limited to, the following: (i) fluid analysis (e.g., tests of a subject's fluids including but not limited to aqueous humor and vitreous humor, bile, blood, blood serum, breast milk, cerebrospinal fluid, cerumen (earwax), digestive fluids, endolymph and perilymph, female ejaculate, gastric juice, mucus (including nasal drainage and phlegm), peritoneal fluid, pleural fluid, saliva, sebum (skin oil), semen, sweat, synovial fluid, tears, vaginal secretion, vomit, and urine), (ii) imaging (e.g., ordinary x-rays, ultrasonography, radioisotope (nuclear) scanning, computed tomography (CT), magnetic resonance imaging (MRI), positron emission tomography (PET), and angiography), (iii) endoscopy (e.g., laryngoscopy, bronchoscopy, esophagoscopy, gastroscopy, GI endoscopy, colloscopy, cystoscopy, hysteroscopy, arthroscopy, laparoscopy, mediastinoscopy, and thoracoscopy), (iv) analysis of organ activity (e.g., electrocardiography (ECG), electroencephalography (EEG), and pulse oximetry), (v) biopsy (e.g., removal of tissue samples for microscopic evaluation), and (vi) genetic testing.

In an aspect, a disclosed method or a disclosed method of inhibiting or ameliorating a SARS-CoV-2 infection can comprise obtaining a disclosed compound (e.g., CLQ, CLBQ14, or CLCQ, or an analog or derivative thereof), obtaining a disclosed composition, obtaining a disclosed formulation comprising a disclosed composition, obtaining one or more active agents, one or more biologically active agents, pharmaceutically active agents, immune-based therapeutic agents, clinically approved agents, or obtaining a combination thereof.

In an aspect, a disclosed method or a disclosed method of inhibiting or ameliorating a SARS-CoV-2 infection can comprise preparing a disclosed compound (e.g., CLQ, CLBQ14, or CLCQ, or an analog or derivative thereof) or preparing a disclosed composition comprising CLQ, CLBQ14, or CLCQ, or analogs or derivatives thereof, or a combination thereof. In an aspect, a disclosed method or a disclosed method of inhibiting or ameliorating a SARS-CoV-2 infection can comprise (1) preparing a disclosed composition comprising CLQ, CLBQ14, or CLCQ, or analogs or derivatives thereof, or a combination thereof, and (2) preparing (i) one or more active agents, (ii) one or more biologically active agents, (iii) one or more pharmaceutically active agents, (iv) one or more immune-based therapeutic agents, (v) one or more clinically approved agents, or (vi) a combination thereof. In an aspect, a disclosed method or a disclosed method of inhibiting or ameliorating a SARS-CoV-2 can comprise preparing one or more active agents, one or more biologically active agents, one or more pharmaceutically active agents, one or more immune-based therapeutic agents, one or more clinically approved agents, or a combination thereof. In an aspect, a disclosed method or a disclosed method of inhibiting or ameliorating a SARS-CoV-2 infection can comprise preparing a disclosed composition comprising (i) CLQ, CLBQ14, or CLCQ, or analogs or derivatives thereof, or a combination thereof, and (ii) one or more active agents, biologically active agents, pharmaceutically active agents, immune-based therapeutic agents, clinically approved agents, or a combination thereof.

i. Method of Inhibiting or Ameliorating One or More SARS-CoV-2 Infection Induced Cytopathic Effects Disclosed herein is a method comprising administering a composition comprising an effective amount of CLQ, CLBQ14, or CLCQ, or analogs or derivatives thereof, or a combination thereof, and inhibiting or ameliorating one or more SARS-CoV-2 infection induced cytopathic effects. Disclosed herein is a method comprising inhibiting or ameliorating one or more SARS-CoV-2 infection induced cytopathic effects by administering a composition comprising an effective amount of CLQ, CLBQ14, or CLCQ, or analogs or derivatives thereof, or a combination thereof. Disclosed herein is a method of inhibiting or ameliorating one or more SARS-CoV-2 infection induced cytopathic effects comprising administering a composition comprising an effective amount of CLQ, CLBQ14, or CLCQ, or analogs or derivatives thereof, or a combination thereof. Disclosed herein is a method of inhibiting or ameliorating one or more SARS-CoV-2 infection induced cytopathic effects in a subject comprising administering to a subject a composition comprising an effective amount of CLQ, CLBQ14, or CLCQ, or analogs or derivatives thereof, or a combination thereof, and inhibiting or ameliorating one or more SARS-CoV-2 infection induced cytopathic effects in the subject. Disclosed herein is a method of inhibiting or ameliorating one or more SARS-CoV-2 infection induced cytopathic effects in a subject comprising inhibiting or ameliorating one or more SARS-CoV-2 infection induced cytopathic effects in the subject by administering to a subject a composition comprising an effective amount of CLQ, CLBQ14, or CLCQ, or analogs or derivatives thereof, or a combination thereof.

In an aspect, a disclosed method or a disclosed method of inhibiting or ameliorating one or more SARS-CoV-2 infection induced cytopathic effects can comprise administering one or more active agents, one or more biologically active agents, pharmaceutically active agents, immune-based therapeutic agents, clinically approved agents, or a combination thereof. Biologically active agents are described herein and are known to the art. Pharmaceutically active agents are described herein and are known to the art. Immune-based therapeutic agents are described herein and are known to the art. Clinically approved active agents can comprise one or more FDA-approved active agents regardless of whether an active agent is a biologically active agent, a pharmaceutically active agent, or an immune-based therapeutic agent.

In an aspect, a disclosed composition in a disclosed method or a disclosed method of inhibiting or ameliorating one or more SARS-CoV-2 infection induced cytopathic effects can comprise (i) one or more active agents, (ii) biologically active agents, (iii) one or more pharmaceutically active agents, (iv) one or more immune-based therapeutic agents, (v) one or more clinically approved agents, or (vi) a combination thereof. In an aspect, a disclosed method or a disclosed method of inhibiting or ameliorating one or more SARS-CoV-2 infection induced cytopathic effects can comprise administering (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof. In an aspect, a disclosed composition in a disclosed method or a disclosed method of inhibiting or ameliorating one or more SARS-CoV-2 infection induced cytopathic effects can comprise (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof.

In an aspect, a composition in a disclosed method or a disclosed method of inhibiting or ameliorating one or more SARS-CoV-2 infection induced cytopathic effects may comprise CLQ, CLBQ14, and/or CLCQ, or analogs or derivatives thereof, or a combination thereof. The composition may be administered in various formats, such as tablet, capsule, syrup, dry powder sachets, inhalation solution/nebulization, drops, ampules, suppository, creams or ointments. For example, the composition may be administered in a tablet format. Tablets may be formulated for controlled release formulation, delayed release formulation, extended release formulation, sustained release formulation, pulsatile release formulation, or mixed immediate release formulation. Tablets may be effervescent. The composition may be administered in a capsule format. Capsules may be formulated for immediate release or sustained release, as examples. Capsules may be hard capsules or and soft capsules. Solution formats may be oil based, aqueous, or emulsions.

In various embodiments, the composition comprising CLQ, CLBQ14, and/or CLCQ, or analogs or derivatives thereof, or a combination thereof, may be administered via any suitable administration route. Example administration routes include parenteral administration, which may include intramuscular, intraarterial, or intravenous, as examples. Example administration routes include nonparenteral administration, such as oral, rectal, vaginal, nasal, mucosal, percutaneous, transdermal, or ophthalmic, as examples.

The composition comprising CLQ, CLBQ14, and/or CLCQ, or analogs or derivatives thereof, or a combination thereof, may be administered in a suitable dosage format, via a suitable route of administration, such as any of those identified above, and in an effective daily dose to inhibit or ameliorate a SARS-CoV-2 infection, such as by any mechanism identified herein. The daily dose may be between 30 mg up to 2,000 mg. Example daily dosages may include greater than 200 mg, greater than 400 mg, greater than 500 mg, greater than 600 mg, greater than 700 mg, greater than 800 mg, greater than 900 mg, greater than 1000 mg, between 50 mg and 100 mg, between 100 mg and 200 mg, between 150 mg and 300 mg, between 200 mg and 1000 mg, between 500 mg and 1500 mg, between 450 mg and 1200 mg, between 500 mg and 2000 mg, between 1000 mg and 2000 mg, or any range between 30 mg and 2000 mg. The composition will typically be administered once daily, twice daily, or three times daily; however, additional administrations may be used.

In an aspect, a disclosed method or a disclosed method of inhibiting or ameliorating one or more SARS-CoV-2 infection induced cytopathic effects can comprise repeating one or more steps.

In an aspect, a disclosed method or a disclosed method of inhibiting or ameliorating one or more SARS-CoV-2 infection induced cytopathic effects can comprise identifying a subject having been diagnosed with or suspected of having a SARS-CoV-2 infection. As known to the art, a SARS-CoV-2 infection can be diagnosed and/or confirmed through various tests (such as, e.g., a PCR test or an antigen test). In an aspect, a disclosed method or a disclosed method of inhibiting or ameliorating one or more SARS-CoV-2 infection induced cytopathic effects can comprise identifying a subject having been diagnosed with or suspected of having a SARS-CoV-2 re-infection. As known to the art, a past SARS-CoV-2 infection can be diagnosed and/or confirmed through an antibody test. In an aspect, an antibody test (also known as serology testing) can check for Immunoglobulin G (IgG) antibody. In an aspect, a variety of factors can impact the results from an antibody test in a disclosed method (e.g., the time the test was taken after experiencing symptoms, the absence of or time since exposure to the virus, or the lack of an adequate immune response, which can be due to conditions or treatments that suppress immune function).

In an aspect, the administering step of a disclosed method or a disclosed method of inhibiting or ameliorating one or more SARS-CoV-2 infection induced cytopathic effects can comprise administering to a subject. In an aspect, a subject can be a human. In an aspect, a human subject can be a participant in a clinical trial. In an aspect, a subject can be a human or a non-human primate diagnosed with or suspected of having a SARS-CoV-2 infection.

In an aspect, a disclosed method or a disclosed method of inhibiting or ameliorating one or more SARS-CoV-2 infection induced cytopathic effects can comprise identifying and/or characterizing one or more comorbidities in a subject. In an aspect, a subject can have one or more comorbidities. Comorbidities are known to the art and can comprise cancer, chronic kidney disease, COPD (chronic obstructive pulmonary disease), an immunocompromised state (weakened immune system) from a solid organ transplant or from a blood or bone marrow transplant, obesity (body mass index [BMI] of 30 or higher), heart conditions (such as, e.g., heart failure, coronary artery disease, or cardiomyopathies), sickle cell disease, type 1 diabetes mellitus or type 2 diabetes mellitus, asthma, cerebrovascular disease, cystic fibrosis, hypertension or high blood pressure, immune deficiencies, HIV, use of corticosteroids, or use of other immune weakening medicines, neurologic conditions, liver disease, pregnancy, pulmonary fibrosis (having damaged or scarred lung tissues), a history of smoking, and thalassemia (a type of blood disorder).

In an aspect, a disclosed method or a disclosed method of inhibiting or ameliorating one or more SARS-CoV-2 infection induced cytopathic effects can comprise treating or ameliorating one or more comorbidities in a subject. For example, in an aspect, a disclosed method or a disclosed method of inhibiting or ameliorating one or more SARS-CoV-2 infection induced cytopathic effects can comprise (i) administering one or more active agents to treat or ameliorate one or more comorbidities, (ii) administering one or more active agents to treat or ameliorate the same comorbidity, (iii) administering one or more active agents to treat or ameliorate different comorbidities (e.g., an active agent for type 2 diabetes and a different active agent for hypertension), or (iv) a combination thereof. In an aspect, administering an active agent to treat or ameliorate one or more comorbidities can occur prior to, concurrently with, or after the administering of a disclosed composition. In an aspect, a disclosed method or a disclosed method of inhibiting or ameliorating one or more SARS-CoV-2 infection induced cytopathic effects can comprise repeating the administering step of an active agent to treat or ameliorate one or more comorbidities.

In an aspect, a disclosed method or a disclosed method of inhibiting or ameliorating one or more SARS-CoV-2 infection induced cytopathic effects can comprise modifying or altering one or more steps of a disclosed method. For example, in an aspect, a disclosed method can comprise modifying or altering an administering step. In an aspect, an administering step can be modified or altered, for example, by changing the route of administration, or changing the dose of a disclosed composition, or changing the timing of administration, or changing the frequency of the administration, or a combination thereof.

In an aspect, altering or modifying one or more steps of a disclosed method or a disclosed method of inhibiting or ameliorating one or more SARS-CoV-2 infection induced cytopathic effects, such as, for example, an administering step, can be based on the identification and/or characterization of one or more comorbidities in a subject. In an aspect, a disclosed method or a disclosed method of inhibiting or ameliorating one or more SARS-CoV-2 infection induced cytopathic effects can comprise modifying or altering the administering step of an active agent to treat or ameliorate one or more comorbidities.

In an aspect, a disclosed method or a disclosed method of inhibiting or ameliorating one or more SARS-CoV-2 infection induced cytopathic effects can comprise determining, measuring, and/or ascertaining the presence and/or severity of an infection, such as, for example, a SARS-CoV-2 infection, a bacterial infection, a viral infection, a fungal infection, or a combination thereof. Methods and techniques used to determine, measure, and/or ascertain the presence and/or severity of an infection such as a SARS-CoV-2 infection are typically known to the medical arts.

In an aspect, a disclosed method or a disclosed method of inhibiting or ameliorating one or more SARS-CoV-2 infection induced cytopathic effects can comprise monitoring a subject's response to the administration of a disclosed composition comprising CLQ, CLBQ14, or CLCQ, or analogs or derivatives thereof, or a combination thereof. In an aspect of a disclosed method, a monitoring step can be repeated one or more times.

In an aspect, a disclosed method or a disclosed method of inhibiting or ameliorating one or more SARS-CoV-2 infection induced cytopathic effects can comprise monitoring a subject's response to the administration of a disclosed composition comprising (i) CLQ, CLBQ14, or CLCQ, or analogs or derivatives thereof, or a combination thereof and (ii) one or more disclosed active agents, one or more biologically active agents, one or more pharmaceutically active agents, one or more immune-based therapeutic agents, one or more clinically approved agents, or a combination thereof. In an aspect of a disclosed method, a monitoring step can be repeated one or more times.

Methods and techniques to monitor a subject's response to a disclosed method of inhibiting or ameliorating one or more SARS-CoV-2 infection induced cytopathic effects can comprise qualitative (or subjective) means as well as quantitative (or objective) means. In an aspect, qualitative means (or subjective means) can comprise a subject's own perspective. For example, a subject can report how he/she is feeling, whether he/she has experienced improvements and/or setbacks, whether he/she has experienced an amelioration or an intensification of one or more symptoms, or a combination thereof. In an aspect, quantitative means (or objective means) can comprise methods and techniques that include, but are not limited to, the following: (i) fluid analysis (e.g., tests of a subject's fluids including but not limited to aqueous humor and vitreous humor, bile, blood, blood serum, breast milk, cerebrospinal fluid, cerumen (earwax), digestive fluids, endolymph and perilymph, female ejaculate, gastric juice, mucus (including nasal drainage and phlegm), peritoneal fluid, pleural fluid, saliva, sebum (skin oil), semen, sweat, synovial fluid, tears, vaginal secretion, vomit, and urine), (ii) imaging (e.g., ordinary x-rays, ultrasonography, radioisotope (nuclear) scanning, computed tomography (CT), magnetic resonance imaging (MRI), positron emission tomography (PET), and angiography), (iii) endoscopy (e.g., laryngoscopy, bronchoscopy, esophagoscopy, gastroscopy, GI endoscopy, coloscopy, cystoscopy, hysteroscopy, arthroscopy, laparoscopy, mediastinoscopy, and thoracoscopy), (iv) analysis of organ activity (e.g., electrocardiography (ECG), electroencephalography (EEG), and pulse oximetry), (v) biopsy (e.g., removal of tissue samples for microscopic evaluation), and (vi) genetic testing.

In an aspect, a disclosed method or a disclosed method of inhibiting or ameliorating one or more SARS-CoV-2 infection induced cytopathic effects can comprise obtaining a disclosed compound (e.g., CLQ, CLBQ14, or CLCQ, or an analog or derivative thereof), obtaining a disclosed composition, obtaining a disclosed formulation comprising a disclosed composition, obtaining one or more active agents, one or more biologically active agents, pharmaceutically active agents, immune-based therapeutic agents, clinically approved agents, or obtaining a combination thereof. In an aspect, a disclosed method or a disclosed method of inhibiting or ameliorating one or more SARS-CoV-2 infection induced cytopathic effects can comprise preparing a disclosed compound (e.g., CLQ, CLBQ14, or CLCQ, or an analog or derivative thereof) or preparing a disclosed composition comprising CLQ, CLBQ14, or CLCQ, or analogs or derivatives thereof, or a combination thereof. In an aspect, a disclosed method or a disclosed method of inhibiting or ameliorating one or more SARS-CoV-2 infection induced cytopathic effects can comprise (1) preparing a disclosed composition comprising CLQ, CLBQ14, or CLCQ, or analogs or derivatives thereof, or a combination thereof, and (2) preparing (i) one or more active agents, (ii) one or more biologically active agents, (iii) one or more pharmaceutically active agents, (iv) one or more immune-based therapeutic agents, (v) one or more clinically approved agents, or (vi) a combination thereof. In an aspect, a disclosed method or a disclosed method of inhibiting or ameliorating one or more SARS-CoV-2 infection induced cytopathic effects can comprise preparing one or more active agents, one or more biologically active agents, one or more pharmaceutically active agents, one or more immune-based therapeutic agents, one or more clinically approved agents, or a combination thereof. In an aspect, a disclosed method or a disclosed method of inhibiting or ameliorating one or more SARS-CoV-2 infection induced cytopathic effects can comprise preparing a disclosed composition comprising (i) CLQ, CLBQ14, or CLCQ, or analogs or derivatives thereof, or a combination thereof, and (ii) one or more active agents, biologically active agents, pharmaceutically active agents, immune-based therapeutic agents, clinically approved agents, or a combination thereof.

ii. Method of Inhibiting or Reducing the Exopeptidase Activity of ACE2

Disclosed herein is a method comprising inhibiting or reducing the exopeptidase activity of angiotensin converting enzyme 2 (ACE2) by administering a composition comprising an effective amount of CLQ, CLBQ14, or CLCQ, or analogs or derivatives thereof, or a combination thereof. Disclosed herein is a method comprising inhibiting or reducing the exopeptidase activity of angiotensin converting enzyme 2 (ACE2) by administering a composition comprising an effective amount of CLQ, CLBQ14, or CLCQ, or analogs or derivatives thereof, or a combination thereof, and by administering a composition comprising an effective amount of zinc chloride. Disclosed herein is a method of inhibiting or reducing exopeptidase activity of an enzyme comprising administering a composition comprising an effective amount of CLQ, CLBQ14, or CLCQ, or analogs or derivatives thereof, or a combination thereof, and inhibiting or reducing the exopeptidase activity of angiotensin converting enzyme 2 (ACE2). Disclosed herein is a method of inhibiting or reducing exopeptidase activity of an enzyme comprising administering a composition comprising an effective amount of CLQ, CLBQ14, or CLCQ, or analogs or derivatives thereof, or a combination thereof, administering a composition comprising an effective amount of zinc chloride; and inhibiting or reducing the exopeptidase activity of angiotensin converting enzyme 2 (ACE2). Disclosed herein is a method of inhibiting or reducing exopeptidase activity of an enzyme comprising inhibiting or reducing the exopeptidase activity of angiotensin converting enzyme 2 (ACE2) by administering a composition comprising an effective amount of CLQ, CLBQ14, or CLCQ, or analogs or derivatives thereof, or a combination thereof. Disclosed herein is method of inhibiting or reducing exopeptidase activity of an enzyme comprising inhibiting or reducing the exopeptidase activity of angiotensin converting enzyme 2 (ACE2) by administering a composition comprising an effective amount of CLQ, CLBQ14, or CLCQ, or analogs or derivatives thereof, or a combination thereof and by administering a composition comprising an effective amount of zinc chloride.

In an aspect, the receptor binding domain (RBD) of the Spike glycoprotein can bind to the metallopeptidase domain (MPD) of ACE2.

In an aspect, a disclosed method of inhibiting or reducing exopeptidase activity of an enzyme can comprise administering one or more active agents, one or more biologically active agents, one or more pharmaceutically active agents, one or more immune-based therapeutic agents, one or more clinically approved agents, or a combination thereof. Biologically active agents are described herein and are known to the art. Pharmaceutically active agents are described herein and are known to the art. Immune-based therapeutic agents are described herein and are known to the art. Clinically approved active agents can comprise one or more FDA-approved active agents regardless of whether an active agent is a biologically active agent, a pharmaceutically active agent, or an immune-based therapeutic agent.

In an aspect, a disclosed composition in a disclosed method of inhibiting or reducing exopeptidase activity of an enzyme can comprise (i) one or more active agents, (ii) one or more biologically active agents, (iii) one or more pharmaceutically active agents, (iv) one or more immune-based therapeutic agents, (v) one or more clinically approved agents, or (vi) a combination thereof. In an aspect, a disclosed method of inhibiting or reducing exopeptidase activity of an enzyme can comprise administering (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof. In an aspect, a disclosed composition in a disclosed method of inhibiting or reducing exopeptidase activity of an enzyme can comprise (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof.

In an aspect, a composition in a disclosed method or a disclosed method of inhibiting or reducing the exopeptidase activity of angiotensin converting enzyme 2 (ACE2) may comprise CLQ, CLBQ14, and/or CLCQ, or analogs or derivatives thereof, or a combination thereof. The composition may be administered in various formats, such as tablet, capsule, syrup, dry powder sachets, inhalation solution/nebulization, drops, ampules, suppository, creams or ointments. For example, the composition may be administered in a tablet format. Tablets may be formulated for controlled release formulation, delayed release formulation, extended release formulation, sustained release formulation, pulsatile release formulation, or mixed immediate release formulation. Tablets may be effervescent. The composition may be administered in a capsule format. Capsules may be formulated for immediate release or sustained release, as examples. Capsules may be hard capsules or and soft capsules. Solution formats may be oil based, aqueous, or emulsions.

In various embodiments, the composition comprising CLQ, CLBQ14, and/or CLCQ, or analogs or derivatives thereof, or a combination thereof, may be administered via any suitable administration route. Example administration routes include parenteral administration, which may include intramuscular, intraarterial, or intravenous, as examples. Example administration routes include nonparenteral administration, such as oral, rectal, vaginal, nasal, mucosal, percutaneous, transdermal, or ophthalmic, as examples.

The composition comprising CLQ, CLBQ14, and/or CLCQ, or analogs or derivatives thereof, or a combination thereof, may be administered in a suitable dosage format, via a suitable route of administration, such as any of those identified above, and in an effective daily dose to inhibit or ameliorate a SARS-CoV-2 infection, such as by any mechanism identified herein. The daily dose may be between 30 mg up to 2,000 mg. Example daily dosages may include greater than 200 mg, greater than 400 mg, greater than 500 mg, greater than 600 mg, greater than 700 mg, greater than 800 mg, greater than 900 mg, greater than 1000 mg, between 50 mg and 100 mg, between 100 mg and 200 mg, between 150 mg and 300 mg, between 200 mg and 1000 mg, between 500 mg and 1500 mg, between 450 mg and 1200 mg, between 500 mg and 2000 mg, between 1000 mg and 2000 mg, or any range between 30 mg and 2000 mg. The composition will typically be administered once daily, twice daily, or three times daily; however, additional administrations may be used.

In an aspect, a disclosed method or a disclosed method of inhibiting or reducing the exopeptidase activity of angiotensin converting enzyme 2 (ACE2) can comprise repeating one or more steps.

In an aspect, a disclosed method or a disclosed method of inhibiting or reducing the exopeptidase activity of angiotensin converting enzyme 2 (ACE2) can comprise identifying a subject having been diagnosed with or suspected of having a SARS-CoV-2 infection. As known to the art, a SARS-CoV-2 infection can be diagnosed and/or confirmed through various tests (such as, e.g., a PCR test or an antigen test).

In an aspect, a disclosed method or a disclosed method of inhibiting or reducing the exopeptidase activity of angiotensin converting enzyme 2 (ACE2) can comprise identifying a subject having been diagnosed with or suspected of having a SARS-CoV-2 re-infection. As known to the art, a past SARS-CoV-2 infection can be diagnosed and/or confirmed through an antibody test. In an aspect, an antibody test (also known as serology testing) can check for Immunoglobulin G (IgG) antibody. In an aspect, a variety of factors can impact the results from an antibody test in a disclosed method (e.g., the time the test was taken after experiencing symptoms, the absence of or time since exposure to the virus, or the lack of an adequate immune response, which can be due to conditions or treatments that suppress immune function).

In an aspect, the administering step of a disclosed method or a disclosed method of inhibiting or reducing the exopeptidase activity of angiotensin converting enzyme 2 (ACE2) can comprise administering to a subject. In an aspect, a subject can be a human. In an aspect, a human subject can be a participant in a clinical trial. In an aspect, a subject can be a human or a non-human primate diagnosed with or suspected of having a SARS-CoV-2 infection.

In an aspect, a disclosed method or a disclosed method of inhibiting or reducing the exopeptidase activity of angiotensin converting enzyme 2 (ACE2) can comprise identifying and/or characterizing one or more comorbidities in a subject. In an aspect of a disclosed method, a subject can have one or more comorbidities. Comorbidities are known to the art and can comprise cancer, chronic kidney disease, COPD (chronic obstructive pulmonary disease), an immunocompromised state (weakened immune system) from a solid organ transplant or from a blood or bone marrow transplant, obesity (body mass index [BMI] of 30 or higher), heart conditions (such as, e.g., heart failure, coronary artery disease, or cardiomyopathies), sickle cell disease, type 1 diabetes mellitus or type 2 diabetes mellitus, asthma, cerebrovascular disease, cystic fibrosis, hypertension or high blood pressure, immune deficiencies, HIV, use of corticosteroids, or use of other immune weakening medicines, neurologic conditions, liver disease, pregnancy, pulmonary fibrosis (having damaged or scarred lung tissues), a history of smoking, and thalassemia (a type of blood disorder).

In an aspect, a disclosed method or a disclosed method of inhibiting or reducing the exopeptidase activity of angiotensin converting enzyme 2 (ACE2) can comprise treating or ameliorating one or more comorbidities in a subject. For example, in an aspect, a disclosed method or a disclosed method of inhibiting or ameliorating a SARS-CoV-2 infection can comprise (i) administering one or more active agents to treat or ameliorate one or more comorbidities, (ii) administering one or more active agents to treat or ameliorate the same comorbidity, (iii) administering one or more active agents to treat or ameliorate different comorbidities (e.g., an active agent for type 2 diabetes and a different active agent for hypertension), or (iv) a combination thereof. In an aspect, administering an active agent to treat or ameliorate one or more comorbidities can occur prior to, concurrently with, or after the administering of a disclosed composition. In an aspect, a disclosed method or a disclosed method of inhibiting or ameliorating a SARS-CoV-2 infection can comprise repeating the administering step of an active agent to treat or ameliorate one or more comorbidities.

In an aspect, a disclosed method or a disclosed method of inhibiting or reducing the exopeptidase activity of angiotensin converting enzyme 2 (ACE2) can comprise modifying or altering one or more steps of a disclosed method. For example, in an aspect, a disclosed method or a disclosed method of inhibiting or reducing the exopeptidase activity of angiotensin converting enzyme 2 (ACE2) can comprise modifying or altering an administering step. In an aspect, an administering step can be modified or altered, for example, by changing the route of administration, or changing the dose of a disclosed composition, or changing the timing of administration, or changing the frequency of the administration, or a combination thereof.

In an aspect, altering or modifying one or more steps of a disclosed method or a disclosed method of inhibiting or reducing the exopeptidase activity of angiotensin converting enzyme 2 (ACE2) can be based on the identification and/or characterization of one or more comorbidities in a subject. In an aspect, a disclosed method or a disclosed method of inhibiting or reducing the exopeptidase activity of angiotensin converting enzyme 2 (ACE2) can comprise modifying or altering the administering step of an active agent to treat or ameliorate one or more comorbidities.

In an aspect, a disclosed method or a disclosed method of inhibiting or reducing the exopeptidase activity of angiotensin converting enzyme 2 (ACE2) can comprise determining, measuring, and/or ascertaining the presence and/or severity of an infection, such as, for example, a SARS-CoV-2 infection, a bacterial infection, a viral infection, a fungal infection, or a combination thereof. Methods and techniques used to determine, measure, and/or ascertain the presence and/or severity of an infection such as a SARS-CoV-2 infection are typically known to the medical arts.

In an aspect, a disclosed method or a disclosed method of inhibiting or reducing the exopeptidase activity of angiotensin converting enzyme 2 (ACE2) can comprise monitoring a subject's response to the administration of a disclosed composition comprising CLQ, CLBQ14, or CLCQ, or analogs or derivatives thereof, or a combination thereof. In an aspect of a disclosed method, a monitoring step can be repeated one or more times.

In an aspect, a disclosed method or a disclosed method of inhibiting or reducing the exopeptidase activity of angiotensin converting enzyme 2 (ACE2) can comprise monitoring a subject's response to the administration of a disclosed composition comprising (i) CLQ, CLBQ14, or CLCQ, or analogs or derivatives thereof, or a combination thereof and (ii) one or more disclosed active agents, one or more biologically active agents, one or more pharmaceutically active agents, one or more immune-based therapeutic agents, one or more clinically approved agents, or a combination thereof. In an aspect of a disclosed method, a monitoring step can be repeated one or more times.

Methods and techniques to monitor a subject's response to a disclosed method can comprise qualitative (or subjective) means as well as quantitative (or objective) means. In an aspect, qualitative means (or subjective means) can comprise a subject's own perspective. For example, a subject can report how he/she is feeling, whether he/she has experienced improvements and/or setbacks, whether he/she has experienced an amelioration of one or more symptoms, or a combination thereof. In an aspect, quantitative means (or objective means) can comprise methods and techniques that include, but are not limited to, the following: (i) fluid analysis (e.g., tests of a subject's fluids including but not limited to aqueous humor and vitreous humor, bile, blood, blood serum, breast milk, cerebrospinal fluid, cerumen (earwax), digestive fluids, endolymph and perilymph, female ejaculate, gastric juice, mucus (including nasal drainage and phlegm), peritoneal fluid, pleural fluid, saliva, sebum (skin oil), semen, sweat, synovial fluid, tears, vaginal secretion, vomit, and urine), (ii) imaging (e.g., ordinary x-rays, ultrasonography, radioisotope (nuclear) scanning, computed tomography (CT), magnetic resonance imaging (MRI), positron emission tomography (PET), and angiography), (iii) endoscopy (e.g., laryngoscopy, bronchoscopy, esophagoscopy, gastroscopy, GI endoscopy, coloscopy, cystoscopy, hysteroscopy, arthroscopy, laparoscopy, mediastinoscopy, and thoracoscopy), (iv) analysis of organ activity (e.g., electrocardiography (ECG), electroencephalography (EEG), and pulse oximetry), (v) biopsy (e.g., removal of tissue samples for microscopic evaluation), and (vi) genetic testing.

In an aspect, a disclosed method or a disclosed method of inhibiting or reducing the exopeptidase activity of angiotensin converting enzyme 2 (ACE2) can comprise obtaining a disclosed compound (e.g., CLQ, CLBQ14, or CLCQ, or an analog or derivative thereof), obtaining a disclosed composition, obtaining a disclosed formulation comprising a disclosed composition, obtaining one or more active agents, one or more biologically active agents, pharmaceutically active agents, immune-based therapeutic agents, clinically approved agents, or obtaining a combination thereof.

In an aspect, a disclosed method or a disclosed method of inhibiting or reducing the exopeptidase activity of angiotensin converting enzyme 2 (ACE2) can comprise preparing a disclosed compound (e.g., CLQ, CLBQ14, or CLCQ, or an analog or derivative thereof) or preparing a disclosed composition comprising CLQ, CLBQ14, or CLCQ, or analogs or derivatives thereof, or a combination thereof. In an aspect, a disclosed method or a disclosed method of inhibiting or reducing the exopeptidase activity of angiotensin converting enzyme 2 (ACE2) can comprise (1) preparing a disclosed composition comprising CLQ, CLBQ14, or CLCQ, or analogs or derivatives thereof, or a combination thereof, and (2) preparing (i) one or more active agents, (ii) one or more biologically active agents, (iii) one or more pharmaceutically active agents, (iv) one or more immune-based therapeutic agents, (v) one or more clinically approved agents, or (vi) a combination thereof. In an aspect, a disclosed method or a disclosed method of inhibiting or reducing the exopeptidase activity of angiotensin converting enzyme 2 (ACE2) can comprise preparing one or more active agents, one or more biologically active agents, one or more pharmaceutically active agents, one or more immune-based therapeutic agents, one or more clinically approved agents, or a combination thereof. In an aspect, a disclosed method or a disclosed method of inhibiting or reducing the exopeptidase activity of angiotensin converting enzyme 2 (ACE2) can comprise preparing a disclosed composition comprising (i) CLQ, CLBQ14, or CLCQ, or analogs or derivatives thereof, or a combination thereof, and (ii) one or more active agents, biologically active agents, pharmaceutically active agents, immune-based therapeutic agents, clinically approved agents, or a combination thereof.

iii. Method of Inhibiting or Disrupting the Interaction Between ACE2 and Spike Protein Disclosed herein is a method comprising administering a composition comprising an effective amount of CLQ, CLBQ14, or CLCQ, or analogs or derivatives thereof, or a combination thereof, and inhibiting or disrupting the physical interaction of angiotensin converting enzyme 2 (ACE2) with the Spike (S) glycoprotein of SARS-CoV-2. Disclosed herein is a method comprising inhibiting or disrupting the physical interaction of angiotensin converting enzyme 2 (ACE2) with the Spike (S) glycoprotein of SARS-CoV-2 by administering a composition comprising an effective amount of CLQ, CLBQ14, or CLCQ, or analogs or derivatives thereof, or a combination thereof. Disclosed herein is a method of inhibiting or disrupting the physical interaction of angiotensin converting enzyme 2 (ACE2) with the Spike (S) glycoprotein of SARS-CoV-2 comprising administering a composition comprising an effective amount of CLQ, CLBQ14, or CLCQ, or analogs or derivatives thereof, or a combination thereof, thereby inhibiting or disrupting the physical interaction of angiotensin converting enzyme 2 (ACE2) with the Spike (S) glycoprotein of SARS-CoV-2. Disclosed herein is a method of inhibiting or reducing viral infectivity in a subject comprising administering to a subject a composition comprising an effective amount of CLQ, CLBQ14, or CLCQ, or analogs or derivatives thereof, or a combination thereof, and inhibiting or disrupting the physical interaction of angiotensin converting enzyme 2 (ACE2) with the Spike (S) glycoprotein of SARS-CoV-2, thereby inhibiting or reducing viral infectivity. Disclosed herein is a method of inhibiting or reducing viral infectivity in a subject comprising inhibiting or disrupting the physical interaction of angiotensin converting enzyme 2 (ACE2) with the Spike (S) glycoprotein of SARS-CoV-2 by administering to a subject a composition comprising an effective amount of CLQ, CLBQ14, or CLCQ, or analogs or derivatives thereof, or a combination thereof, thereby inhibiting or reducing viral infectivity. Disclosed herein is a method of inhibiting or ameliorating a SARS-CoV-2 infection in a subject comprising administering to a subject a composition comprising an effective amount of CLQ, CLBQ14, or CLCQ, or analogs or derivatives thereof, or a combination thereof, and inhibiting or disrupting the physical interaction of angiotensin converting enzyme 2 (ACE2) with the Spike (S) glycoprotein of SARS-CoV-2, thereby inhibiting or ameliorating a SARS-CoV-2 infection. Disclosed herein is a method of inhibiting or ameliorating a SARS-CoV-2 infection in a subject comprising inhibiting or disrupting the physical interaction of angiotensin converting enzyme 2 (ACE2) with the Spike (S) glycoprotein of SARS-CoV-2 by administering to a subject a composition comprising an effective amount of CLQ, CLBQ14, or CLCQ, or analogs or derivatives thereof, or a combination thereof, thereby inhibiting or ameliorating a SARS-CoV-2 infection. Disclosed herein is a method of inhibiting or reducing viral entry into cells of a subject comprising administering to a subject a composition comprising an effective amount of CLQ, CLBQ14, or CLCQ, or analogs or derivatives thereof, or a combination thereof, and inhibiting or disrupting the physical interaction of angiotensin converting enzyme 2 (ACE2) with the Spike (S) glycoprotein of SARS-CoV-2, thereby inhibiting or reducing viral entry into cells of the subject. Disclosed herein is a method of inhibiting or reducing viral entry into cells of a subject comprising inhibiting or disrupting the physical interaction of angiotensin converting enzyme 2 (ACE2) with the Spike (S) glycoprotein of SARS-CoV-2 by administering to a subject a composition comprising an effective amount of CLQ, CLBQ14, or CLCQ, or analogs or derivatives thereof, or a combination thereof, thereby inhibiting or reducing viral entry into cells of the subject.

In an aspect, the receptor binding domain (RBD) of the Spike glycoprotein can bind to the metallopeptidase domain (MPD) of the ACE2 receptor.

In an aspect, a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can comprise administering a composition comprising an effective amount of zinc chloride. In an aspect, a disclosed composition in a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can comprise an effective amount of zinc chloride.

In an aspect, a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can comprise administering one or more active agents, one or more biologically active agents, one or more pharmaceutically active agents, one or more immune-based therapeutic agents, one or more clinically approved agents, or a combination thereof. Biologically active agents are described herein and are known to the art. Pharmaceutically active agents are described herein and are known to the art. Immune-based therapeutic agents are described herein and are known to the art. Clinically approved active agents can comprise one or more FDA-approved active agents regardless of whether an active agent is a biologically active agent, a pharmaceutically active agent, or an immune-based therapeutic agent.

In an aspect, a disclosed composition in a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can comprise (i) one or more active agents, (ii) one or more biologically active agents, (iii) one or more pharmaceutically active agents, (iv) one or more immune-based therapeutic agents, (v) one or more clinically approved agents, or (vi) a combination thereof.

In an aspect, a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can comprise administering (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof.

In an aspect, a disclosed composition in a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can comprise (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof.

In an aspect, a composition in a disclosed method or a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject may comprise CLQ, CLBQ14, and/or CLCQ, or analogs or derivatives thereof, or a combination thereof. The composition may be administered in various formats, such as tablet, capsule, syrup, dry powder sachets, inhalation solution/nebulization, drops, ampules, suppository, creams or ointments. For example, the composition may be administered in a tablet format. Tablets may be formulated for controlled release formulation, delayed release formulation, extended release formulation, sustained release formulation, pulsatile release formulation, or mixed immediate release formulation. Tablets may be effervescent. The composition may be administered in a capsule format. Capsules may be formulated for immediate release or sustained release, as examples. Capsules may be hard capsules or and soft capsules. Solution formats may be oil based, aqueous, or emulsions.

In various embodiments, the composition comprising CLQ, CLBQ14, and/or CLCQ, or analogs or derivatives thereof, or a combination thereof, may be administered via any suitable administration route. Example administration routes include parenteral administration, which may include intramuscular, intraarterial, or intravenous, as examples. Example administration routes include nonparenteral administration, such as oral, rectal, vaginal, nasal, mucosal, percutaneous, transdermal, or ophthalmic, as examples.

The composition comprising CLQ, CLBQ14, and/or CLCQ, or analogs or derivatives thereof, or a combination thereof, may be administered in a suitable dosage format, via a suitable route of administration, such as any of those identified above, and in an effective daily dose to inhibit or ameliorate a SARS-CoV-2 infection, such as by any mechanism identified herein. The daily dose may be between 30 mg up to 2,000 mg. Example daily dosages may include greater than 200 mg, greater than 400 mg, greater than 500 mg, greater than 600 mg, greater than 700 mg, greater than 800 mg, greater than 900 mg, greater than 1000 mg, between 50 mg and 100 mg, between 100 mg and 200 mg, between 150 mg and 300 mg, between 200 mg and 1000 mg, between 500 mg and 1500 mg, between 450 mg and 1200 mg, between 500 mg and 2000 mg, between 1000 mg and 2000 mg, or any range between 30 mg and 2000 mg. The composition will typically be administered once daily, twice daily, or three times daily; however, additional administrations may be used.

In an aspect, a disclosed method or a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can comprise repeating one or more steps.

In an aspect, a disclosed method or a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can comprise identifying a subject having been diagnosed with or suspected of having a SARS-CoV-2 infection. As known to the art, a SARS-CoV-2 infection can be diagnosed and/or confirmed through various tests (such as, e.g., a PCR test or an antigen test).

In an aspect, a disclosed method or a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can comprise identifying a subject having been diagnosed with or suspected of having a SARS-CoV-2 re-infection. As known to the art, a past SARS-CoV-2 infection can be diagnosed and/or confirmed through an antibody test. In an aspect, an antibody test (also known as serology testing) can check for Immunoglobulin G (IgG) antibody. In an aspect, a variety of factors can impact the results from an antibody test in a disclosed method (e.g., the time the test was taken after experiencing symptoms, the absence of or time since exposure to the virus, or the lack of an adequate immune response, which can be due to conditions or treatments that suppress immune function).

In an aspect, the administering step of a disclosed method or a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can comprise administering to a subject. In an aspect, a subject can be a human. In an aspect, a human subject can be a participant in a clinical trial. In an aspect, a subject can be a human or a non-human primate diagnosed with or suspected of having a SARS-CoV-2 infection.

In an aspect, a disclosed method or a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can comprise identifying and/or characterizing one or more comorbidities in a subject. In an aspect, a subject can have one or more comorbidities. Comorbidities are known to the art and can comprise cancer, chronic kidney disease, COPD (chronic obstructive pulmonary disease), an immunocompromised state (weakened immune system) from a solid organ transplant or from a blood or bone marrow transplant, obesity (body mass index [BMI] of 30 or higher), heart conditions (such as, e.g., heart failure, coronary artery disease, or cardiomyopathies), sickle cell disease, type 1 diabetes mellitus or type 2 diabetes mellitus, asthma, cerebrovascular disease, cystic fibrosis, hypertension or high blood pressure, immune deficiencies, HIV, use of corticosteroids, or use of other immune weakening medicines, neurologic conditions, liver disease, pregnancy, pulmonary fibrosis (having damaged or scarred lung tissues), a history of smoking, and thalassemia (a type of blood disorder).

In an aspect, a disclosed method or a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can comprise (i) administering one or more active agents to treat or ameliorate one or more comorbidities, (ii) administering one or more active agents to treat or ameliorate the same comorbidity, (iii) administering one or more active agents to treat or ameliorate different comorbidities (e.g., an active agent for type 2 diabetes and a different active agent for hypertension), or (iv) a combination thereof. In an aspect, administering an active agent to treat or ameliorate one or more comorbidities can occur prior to, concurrently with, or after the administering of a disclosed composition. In an aspect, a disclosed method or a disclosed method of inhibiting or ameliorating a SARS-CoV-2 infection can comprise repeating the administering step of an active agent to treat or ameliorate one or more comorbidities.

In an aspect, a disclosed method or a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can comprise modifying or altering an administering step. In an aspect, an administering step can be modified or altered, for example, by changing the route of administration, or changing the dose of a disclosed composition, or changing the timing of administration, or changing the frequency of the administration, or a combination thereof.

In an aspect, altering or modifying one or more steps of a disclosed method or a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can be based on the identification and/or characterization of one or more comorbidities in a subject.

In an aspect, a disclosed method or a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can comprise modifying or altering the administering step of an active agent to treat or ameliorate one or more comorbidities.

In an aspect, a disclosed method or a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can comprise determining, measuring, and/or ascertaining the presence and/or severity of an infection, such as, for example, a SARS-CoV-2 infection, a bacterial infection, a viral infection, a fungal infection, or a combination thereof. Methods and techniques used to determine, measure, and/or ascertain the presence and/or severity of an infection such as a SARS-CoV-2 infection are typically known to the medical arts.

In an aspect, a disclosed method or a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can comprise monitoring a subject's response to the administration of a disclosed composition comprising CLQ, CLBQ14, or CLCQ, or analogs or derivatives thereof, or a combination thereof. In an aspect of a disclosed method, a monitoring step can be repeated one or more times.

In an aspect, a disclosed method or a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can comprise monitoring a subject's response to the administration of a disclosed composition comprising (i) CLQ, CLBQ14, or CLCQ, or analogs or derivatives thereof, or a combination thereof and (ii) one or more disclosed active agents, one or more biologically active agents, one or more pharmaceutically active agents, one or more immune-based therapeutic agents, one or more clinically approved agents, or a combination thereof. In an aspect of a disclosed method, a monitoring step can be repeated one or more times.

Methods and techniques to monitor a subject's response to a disclosed method can comprise qualitative (or subjective) means as well as quantitative (or objective) means. In an aspect, qualitative means (or subjective means) can comprise a subject's own perspective. For example, a subject can report how he/she is feeling, whether he/she has experienced improvements and/or setbacks, whether he/she has experienced an amelioration or an intensification of one or more symptoms, or a combination thereof. In an aspect, quantitative means (or objective means) can comprise methods and techniques that include, but are not limited to, the following: (i) fluid analysis (e.g., tests of a subject's fluids including but not limited to aqueous humor and vitreous humor, bile, blood, blood serum, breast milk, cerebrospinal fluid, cerumen (earwax), digestive fluids, endolymph and perilymph, female ejaculate, gastric juice, mucus (including nasal drainage and phlegm), peritoneal fluid, pleural fluid, saliva, sebum (skin oil), semen, sweat, synovial fluid, tears, vaginal secretion, vomit, and urine), (ii) imaging (e.g., ordinary x-rays, ultrasonography, radioisotope (nuclear) scanning, computed tomography (CT), magnetic resonance imaging (MRI), positron emission tomography (PET), and angiography), (iii) endoscopy (e.g., laryngoscopy, bronchoscopy, esophagoscopy, gastroscopy, GI endoscopy, coloscopy, cystoscopy, hysteroscopy, arthroscopy, laparoscopy, mediastinoscopy, and thoracoscopy), (iv) analysis of organ activity (e.g., electrocardiography (ECG), electroencephalography (EEG), and pulse oximetry), (v) biopsy (e.g., removal of tissue samples for microscopic evaluation), and (vi) genetic testing.

In an aspect, a disclosed method or a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can comprise obtaining a disclosed compound (e.g., CLQ, CLBQ14, or CLCQ, or an analog or derivative thereof), obtaining a disclosed composition, obtaining a disclosed formulation comprising a disclosed composition, obtaining one or more active agents, one or more biologically active agents, pharmaceutically active agents, immune-based therapeutic agents, clinically approved agents, or obtaining a combination thereof.

In an aspect, a disclosed method or a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can comprise preparing a disclosed compound (e.g., CLQ, CLBQ14, or CLCQ, or an analog or derivative thereof) or preparing a disclosed composition comprising CLQ, CLBQ14, or CLCQ, or analogs or derivatives thereof, or a combination thereof.

In an aspect, a disclosed method or a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject infection can comprise (1) preparing a disclosed composition comprising CLQ, CLBQ14, or CLCQ, or analogs or derivatives thereof, or a combination thereof, and (2) preparing (i) one or more active agents, (ii) one or more biologically active agents, (iii) one or more pharmaceutically active agents, (iv) one or more immune-based therapeutic agents, (v) one or more clinically approved agents, or (vi) a combination thereof.

In an aspect, a disclosed method or a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can comprise preparing one or more active agents, one or more biologically active agents, one or more pharmaceutically active agents, one or more immune-based therapeutic agents, one or more clinically approved agents, or a combination thereof.

In an aspect, a disclosed method or a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a method of inhibiting or reducing viral entry into cells of a subject can comprise preparing a disclosed composition comprising (i) CLQ, CLBQ14, or CLCQ, or analogs or derivatives thereof, or a combination thereof, and (ii) one or more active agents, biologically active agents, pharmaceutically active agents, immune-based therapeutic agents, clinically approved agents, or a combination thereof.

2. Compositions Comprising 8-Hydroxyquinoline Structural Class i. General Composition Disclosed herein is composition comprising an effective amount of one or more compounds belonging to the 8-hydroxyquinoline structural class; and a pharmaceutically acceptable diluent, carrier, excipient, or stabilizer, or a combination thereof, wherein the composition inhibits or ameliorates a SARS-CoV-2 infection. Disclosed herein is a composition comprising an effective amount of CLQ, CLBQ14, or CLCQ, or analogs or derivatives thereof, or a combination thereof, and a pharmaceutically acceptable diluent, carrier, excipient, or stabilizer, or a combination thereof, wherein the composition inhibits or ameliorates a SARS-CoV-2 infection. Disclosed herein is composition comprising an effective amount of one or more compounds belonging to the 8-hydroxyquinoline structural class; an effective amount of one or more clinically approved active agents; and a pharmaceutically acceptable diluent, carrier, excipient, or stabilizer, or a combination thereof, wherein the composition inhibits or ameliorates a SARS-CoV-2 infection. Disclosed herein is a composition comprising an effective amount of CLQ, CLBQ14, or CLCQ, or analogs or derivatives thereof, or a combination thereof, an effective amount of one or more clinically approved active agents; and a pharmaceutically acceptable diluent, carrier, excipient, or stabilizer, or a combination thereof, wherein the composition inhibits or ameliorates a SARS-CoV-2 infection.

The 8-hydroxyquinoline structural class is known to the art and discussed herein. Pharmaceutically acceptable diluents, carriers, excipients, and stabilizers are known to the art and discussed herein.

In an aspect, a disclosed composition comprising one or more compounds belonging to the 8-hydroxyquinoline structural class or a disclosed composition comprising CLQ, CLBQ14, or CLCQ, or analogs or derivatives thereof, or a combination thereof can inhibit or ameliorate a SARS-CoV-2 infection.

In an aspect, a disclosed composition comprising one or more compounds belonging to the 8-hydroxyquinoline structural class or a disclosed composition comprising CLQ, CLBQ14, or CLCQ, or analogs or derivatives thereof, or a combination thereof can comprise one or more active agents, one or more biologically active agents, one or more pharmaceutically active agents, one or more immune-based therapeutic agents, one or more clinically approved agents, or a combination thereof. Biologically active agents are described herein and are known to the art. Pharmaceutically active agents are described herein and are known to the art. Immune-based therapeutic agents are described herein and are known to the art. Clinically approved active agents can comprise one or more FDA-approved active agents regardless of whether an active agent is a biologically active agent, a pharmaceutically active agent, or an immune-based therapeutic agent.

In an aspect, a disclosed composition comprising one or more compounds belonging to the 8-hydroxyquinoline structural class or a disclosed composition comprising CLQ, CLBQ14, or CLCQ, or analogs or derivatives thereof, or a combination thereof can comprise (i) one or more active agents, (ii) one or more biologically active agents, (iii) one or more pharmaceutically active agents, (iv) one or more immune-based therapeutic agents, (v) one or more clinically approved agents, or (vi) a combination thereof.

In an aspect, a disclosed composition comprising one or more compounds belonging to the 8-hydroxyquinoline structural class or a disclosed composition comprising CLQ, CLBQ14, or CLCQ, or analogs or derivatives thereof, or a combination thereof can comprise (i) one or more antibacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof.

A disclosed composition comprising CLQ, CLBQ14, and/or CLCQ, or analogs or derivatives thereof, or a combination thereof, may be administered in various formats, such as tablet, capsule, syrup, dry powder sachets, inhalation solution/nebulization, drops, ampules, suppository, creams or ointments. For example, the composition may be administered in a tablet format. Tablets may be formulated for controlled release formulation, delayed release formulation, extended release formulation, sustained release formulation, pulsatile release formulation, or mixed immediate release formulation. Tablets may be effervescent. The composition may be administered in a capsule format. Capsules may be formulated for immediate release or sustained release, as examples. Capsules may be hard capsules or and soft capsules. Solution formats may be oil based, aqueous, or emulsions.

In various embodiments, the composition comprising CLQ, CLBQ14, and/or CLCQ, or analogs or derivatives thereof, or a combination thereof, may be administered via any suitable administration route. Example administration routes include parenteral administration, which may include intramuscular, intraarterial, or intravenous, as examples. Example administration routes include nonparenteral administration, such as oral, rectal, vaginal, nasal, mucosal, percutaneous, transdermal, or ophthalmic, as examples.

The composition comprising CLQ, CLBQ14, and/or CLCQ, or analogs or derivatives thereof, or a combination thereof, may be administered in a suitable dosage format, via a suitable route of administration, such as any of those identified above, and in an effective daily dose to inhibit or ameliorate a SARS-CoV-2 infection, such as by any mechanism identified herein. The daily dose may be between 30 mg up to 2,000 mg. Example daily dosages may include greater than 200 mg, greater than 400 mg, greater than 500 mg, greater than 600 mg, greater than 700 mg, greater than 800 mg, greater than 900 mg, greater than 1000 mg, between 50 mg and 100 mg, between 100 mg and 200 mg, between 150 mg and 300 mg, between 200 mg and 1000 mg, between 500 mg and 1500 mg, between 450 mg and 1200 mg, between 500 mg and 2000 mg, between 1000 mg and 2000 mg, or any range between 30 mg and 2000 mg. The composition will typically be administered once daily, twice daily, or three times daily; however, additional administrations may be used.

In an aspect, a disclosed composition comprising one or more compounds belonging to the 8-hydroxyquinoline structural class or a disclosed composition comprising CLQ, CLBQ14, or CLCQ, or analogs or derivatives thereof, or a combination thereof can be administered to a subject. In an aspect, a subject can be a human. In an aspect, a human subject can be a participant in a clinical trial. In an aspect, a subject can be a human or a non-human primate diagnosed with or suspected of having a SARS-CoV-2 infection.

In an aspect, a disclosed composition comprising one or more compounds belonging to the 8-hydroxyquinoline structural class or a disclosed composition comprising CLQ, CLBQ14, or CLCQ, or analogs or derivatives thereof, or a combination thereof can be administered to a subject having one or more comorbidities. In an aspect, a disclosed composition comprising one or more compounds belonging to the 8-hydroxyquinoline structural class or a disclosed composition comprising CLQ, CLBQ14, or CLCQ, or analogs or derivatives thereof, or a combination thereof can comprise one or more active agents to treat or ameliorate one or more comorbidities. Comorbidities are known to the art and are discussed herein.

ii. Compositions for Inhibiting or Ameliorating a SARS-CoV-2 Infection

Disclosed herein is a composition comprising an effective amount of CLQ, CLBQ14, or CLCQ, or analogs or derivatives thereof, or a combination thereof, and a pharmaceutically acceptable diluent, carrier, excipient, or stabilizer, or a combination thereof, wherein the composition inhibits or ameliorates one or more SARS-CoV-2 infection induced cytopathic effects. Disclosed herein is a composition comprising an effective amount of CLQ, CLBQ14, or CLCQ, or analogs or derivatives thereof, or a combination thereof; an effective amount of one or more anti-viral agents; and a pharmaceutically acceptable diluent, carrier, excipient, or stabilizer, or a combination thereof, wherein the composition inhibits or ameliorates one or more SARS-CoV-2 infection induced cytopathic effects. Disclosed herein is a composition for inhibiting or ameliorating cytopathic effects in a subject comprising an effective amount of CLQ, CLBQ14, or CLCQ, or analogs or derivatives thereof, or a combination thereof, and a pharmaceutically acceptable diluent, carrier, excipient, or stabilizer, or a combination thereof, wherein the composition inhibits or ameliorates one or more SARS-CoV-2 infection induced cytopathic effects in a subject in need thereof. Disclosed herein is a composition for inhibiting or ameliorating one or more SARS-CoV-2 infection induced cytopathic effects in a subject comprising an effective amount of CLQ, CLBQ14, or CLCQ, or analogs or derivatives thereof, or a combination thereof, an effective amount of one or more anti-viral agents; and a pharmaceutically acceptable diluent, carrier, excipient, or stabilizer, or a combination thereof, wherein the composition inhibits or ameliorates one or more cytopathic effects in a subject in need thereof. Disclosed herein is a composition for inhibiting or ameliorating one or more SARS-CoV-2 infection induced cytopathic effects in a subject comprising an effective amount of CLQ, CLBQ14, or CLCQ, or analogs or derivatives thereof, or a combination thereof, and a pharmaceutically acceptable diluent, carrier, excipient, or stabilizer, or a combination thereof, wherein the composition inhibits or ameliorates one or more SARS-CoV-2 infection induced cytopathic effects in a subject diagnosed with or suspected of having a SARS-CoV-2 infection. Disclosed herein is a composition for inhibiting or ameliorating one or more SARS-CoV-2 infection induced cytopathic effects in a subject comprising an effective amount of CLQ, CLBQ14, or CLCQ, or analogs or derivatives thereof, or a combination thereof, an effective amount of one or more anti-viral agents; and a pharmaceutically acceptable diluent, carrier, excipient, or stabilizer, or a combination thereof; wherein the composition inhibits or ameliorates one or more SARS-CoV-2 infection induced cytopathic effects in a subject diagnosed with or suspected of having a SARS-CoV-2 infection.

In an aspect, a disclosed composition comprising one or more compounds belonging to the 8-hydroxyquinoline structural class or a disclosed composition comprising CLQ, CLBQ14, or CLCQ, or analogs or derivatives thereof, or a combination thereof can inhibit or ameliorate one or more SARS-CoV-2 infection induced cytopathic effects.

In an aspect, a disclosed composition comprising CLQ, CLBQ14, or CLCQ, or analogs or derivatives thereof, or a combination thereof can comprise one or more active agents, one or more biologically active agents, one or more pharmaceutically active agents, one or more immune-based therapeutic agents, one or more clinically approved agents, or a combination thereof. Biologically active agents are described herein and are known to the art. Pharmaceutically active agents are described herein and are known to the art. Immune-based therapeutic agents are described herein and are known to the art. Clinically approved active agents can comprise one or more FDA-approved active agents regardless of whether an active agent is a biologically active agent, a pharmaceutically active agent, or an immune-based therapeutic agent.

In an aspect, a disclosed composition comprising CLQ, CLBQ14, or CLCQ, or analogs or derivatives thereof, or a combination thereof can comprise (i) one or more active agents, (ii) one or more biologically active agents, (iii) one or more pharmaceutically active agents, (iv) one or more immune-based therapeutic agents, (v) one or more clinically approved agents, or (vi) a combination thereof. In an aspect, a disclosed composition comprising CLQ, CLBQ14, or CLCQ, or analogs or derivatives thereof, or a combination thereof can comprise (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof.

A disclosed composition comprising CLQ, CLBQ14, and/or CLCQ, or analogs or derivatives thereof, or a combination thereof, may be administered in various formats, such as tablet, capsule, syrup, dry powder sachets, inhalation solution/nebulization, drops, ampules, suppository, creams or ointments. For example, the composition may be administered in a tablet format. Tablets may be formulated for controlled release formulation, delayed release formulation, extended release formulation, sustained release formulation, pulsatile release formulation, or mixed immediate release formulation. Tablets may be effervescent. The composition may be administered in a capsule format. Capsules may be formulated for immediate release or sustained release, as examples. Capsules may be hard capsules or and soft capsules. Solution formats may be oil based, aqueous, or emulsions.

In various embodiments, the composition comprising CLQ, CLBQ14, and/or CLCQ, or analogs or derivatives thereof, or a combination thereof, may be administered via any suitable administration route. Example administration routes include parenteral administration, which may include intramuscular, intraarterial, or intravenous, as examples. Example administration routes include nonparenteral administration, such as oral, rectal, vaginal, nasal, mucosal, percutaneous, transdermal, or ophthalmic, as examples.

The composition comprising CLQ, CLBQ14, and/or CLCQ, or analogs or derivatives thereof, or a combination thereof, may be administered in a suitable dosage format, via a suitable route of administration, such as any of those identified above, and in an effective daily dose to inhibit or ameliorate a SARS-CoV-2 infection, such as by any mechanism identified herein. The daily dose may be between 30 mg up to 2,000 mg. Example daily dosages may include greater than 200 mg, greater than 400 mg, greater than 500 mg, greater than 600 mg, greater than 700 mg, greater than 800 mg, greater than 900 mg, greater than 1000 mg, between 50 mg and 100 mg, between 100 mg and 200 mg, between 150 mg and 300 mg, between 200 mg and 1000 mg, between 500 mg and 1500 mg, between 450 mg and 1200 mg, between 500 mg and 2000 mg, between 1000 mg and 2000 mg, or any range between 30 mg and 2000 mg. The composition will typically be administered once daily, twice daily, or three times daily; however, additional administrations may be used.

In an aspect, a disclosed composition comprising CLQ, CLBQ14, or CLCQ, or analogs or derivatives thereof, or a combination thereof can be administered to a subject. In an aspect, a subject can be a human. In an aspect, a human subject can be a participant in a clinical trial. In an aspect, a subject can be a non-human primate diagnosed with or suspected of having a SARS-CoV-2 infection.

In an aspect, a disclosed composition comprising CLQ, CLBQ14, or CLCQ, or analogs or derivatives thereof, or a combination thereof can be administered to a subject having one or more comorbidities. In an aspect, a disclosed composition comprising CLQ, CLBQ14, or CLCQ, or analogs or derivatives thereof, or a combination thereof can comprise one or more active agents to treat or ameliorate one or more comorbidities. Comorbidities are known to the art and are discussed herein.

iii. Compositions for Inhibiting or Reducing the Exopeptidase Activity of ACE2

Disclosed herein is a composition for inhibiting or reducing exopeptidase activity of an enzyme comprising an effective amount of CLQ, CLBQ14, or CLCQ, or analogs or derivatives thereof, or a combination thereof, and a pharmaceutically acceptable diluent, carrier, excipient, or stabilizer, or a combination thereof, wherein the composition inhibits or reduces the exopeptidase activity of angiotensin converting enzyme 2 (ACE2). Disclosed herein is a composition for inhibiting or reducing exopeptidase activity of an enzyme comprising an effective amount of CLQ, CLBQ14, or CLCQ, or analogs or derivatives thereof, or a combination thereof, and an effective amount of zinc chloride; wherein the composition inhibits or reduces the exopeptidase activity of angiotensin converting enzyme 2 (ACE2). Disclosed herein is a composition for inhibiting or reducing exopeptidase activity of an enzyme comprising an effective amount of CLQ, CLBQ14, or CLCQ, or analogs or derivatives thereof, or a combination thereof, wherein the composition inhibits or disrupts the physical interaction of angiotensin converting enzyme 2 (ACE2) with the Spike (S) glycoprotein of SARS-CoV-2, thereby inhibiting or reducing the exopeptidase activity of angiotensin converting enzyme 2 (ACE2). Disclosed herein is a composition for inhibiting or reducing exopeptidase activity of an enzyme comprising an effective amount of CLQ, CLBQ14, or CLCQ, or analogs or derivatives thereof, or a combination thereof, and an effective amount of zinc chloride, wherein the composition inhibits or disrupts the physical interaction of angiotensin converting enzyme 2 (ACE2) with the Spike (S) glycoprotein of SARS-CoV-2, thereby inhibiting or reducing the exopeptidase activity of angiotensin converting enzyme 2 (ACE2).

In an aspect, a disclosed composition comprising one or more compounds belonging to the 8-hydroxyquinoline structural class or a disclosed composition comprising CLQ, CLBQ14, or CLCQ, or analogs or derivatives thereof, or a combination thereof can inhibit or reduce the exopeptidase activity of angiotensin converting enzyme 2 (ACE2). In an aspect, a disclosed composition comprising one or more compounds belonging to the 8-hydroxyquinoline structural class or a disclosed composition comprising CLQ, CLBQ14, or CLCQ, or analogs or derivatives thereof, or a combination thereof can inhibit or disrupt the physical interaction of angiotensin converting enzyme 2 (ACE2) with the Spike (S) glycoprotein of SARS-CoV-2

CLQ, CLBQ14, CLCQ, and analogs or derivatives thereof are known to the art and are discussed herein. Pharmaceutically acceptable diluents, carriers, excipients, stabilizers, and combinations thereof are known to the art and are discussed herein.

In an aspect, the receptor binding domain (RBD) of the Spike glycoprotein can bind to the metallopeptidase domain (MPD) of the ACE2 receptor.

In an aspect, a disclosed composition comprising CLQ, CLBQ14, or CLCQ, or analogs or derivatives thereof, or a combination thereof can comprise one or more active agents, one or more biologically active agents, one or more pharmaceutically active agents, one or more immune-based therapeutic agents, one or more clinically approved agents, or a combination thereof. Biologically active agents are described herein and are known to the art. Pharmaceutically active agents are described herein and are known to the art. Immune-based therapeutic agents are described herein and are known to the art. Clinically approved active agents can comprise one or more FDA-approved active agents regardless of whether an active agent is a biologically active agent, a pharmaceutically active agent, or an immune-based therapeutic agent.

In an aspect, a disclosed composition comprising CLQ, CLBQ14, or CLCQ, or analogs or derivatives thereof, or a combination thereof can comprise (i) one or more active agents, (ii) one or more biologically active agents, (iii) one or more pharmaceutically active agents, (iv) one or more immune-based therapeutic agents, (v) one or more clinically approved agents, or (vi) a combination thereof. In an aspect, a disclosed composition comprising CLQ, CLBQ14, or CLCQ, or analogs or derivatives thereof, or a combination thereof can comprise (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof.

In an aspect, a disclosed composition comprising CLQ, CLBQ14, or CLCQ, or analogs or derivatives thereof, or a combination thereof may be administered in various formats, such as tablet, capsule, syrup, dry powder sachets, inhalation solution/nebulization, drops, ampules, suppository, creams or ointments. For example, the composition may be administered in a tablet format. Tablets may be formulated for controlled release formulation, delayed release formulation, extended release formulation, sustained release formulation, pulsatile release formulation, or mixed immediate release formulation. Tablets may be effervescent. The composition may be administered in a capsule format. Capsules may be formulated for immediate release or sustained release, as examples. Capsules may be hard capsules or and soft capsules. Solution formats may be oil based, aqueous, or emulsions.

In various embodiments, the composition comprising CLQ, CLBQ14, and/or CLCQ, or analogs or derivatives thereof, or a combination thereof, may be administered via any suitable administration route. Example administration routes include parenteral administration, which may include intramuscular, intraarterial, or intravenous, as examples. Example administration routes include nonparenteral administration, such as oral, rectal, vaginal, nasal, mucosal, percutaneous, transdermal, or ophthalmic, as examples.

The composition comprising CLQ, CLBQ14, and/or CLCQ, or analogs or derivatives thereof, or a combination thereof, may be administered in a suitable dosage format, via a suitable route of administration, such as any of those identified above, and in an effective daily dose to inhibit or ameliorate a SARS-CoV-2 infection, such as by any mechanism identified herein. The daily dose may be between 30 mg up to 2,000 mg. Example daily dosages may include greater than 200 mg, greater than 400 mg, greater than 500 mg, greater than 600 mg, greater than 700 mg, greater than 800 mg, greater than 900 mg, greater than 1000 mg, between 50 mg and 100 mg, between 100 mg and 200 mg, between 150 mg and 300 mg, between 200 mg and 1000 mg, between 500 mg and 1500 mg, between 450 mg and 1200 mg, between 500 mg and 2000 mg, between 1000 mg and 2000 mg, or any range between 30 mg and 2000 mg. The composition will typically be administered once daily, twice daily, or three times daily; however, additional administrations may be used.

In an aspect, a disclosed composition can be administered to a subject. In an aspect, a subject can be a human. In an aspect, a human subject can be a participant in a clinical trial. In an aspect, a subject can be a human or a non-human primate diagnosed with or suspected of having a SARS-CoV-2 infection.

In an aspect, a disclosed composition comprising CLQ, CLBQ14, or CLCQ, or analogs or derivatives thereof, or a combination thereof can be administered to a subject having one or more comorbidities. In an aspect, a disclosed composition comprising CLQ, CLBQ14, or CLCQ, or analogs or derivatives thereof, or a combination thereof can comprise one or more active agents to treat or ameliorate one or more comorbidities. Comorbidities are known to the art and are discussed herein.

iv. Compositions for Inhibiting or Disrupting the Interaction Between ACE2 and Spike Protein Disclosed herein is a composition comprising an effective amount of CLQ, CLBQ14, or CLCQ, or analogs or derivatives thereof, or a combination thereof, wherein the composition inhibits or disrupts the physical interaction of angiotensin converting enzyme 2 (ACE2) with the Spike (S) glycoprotein of SARS-CoV-2. Disclosed herein is a composition for inhibiting or disrupting the physical interaction of an angiotensin converting enzyme 2 (ACE2) with the Spike (S) glycoprotein of SARS-CoV-2 comprising an effective amount of CLQ, CLBQ14, or CLCQ, or analogs or derivatives thereof, or a combination thereof. Disclosed herein is a composition for inhibiting or reducing viral infectivity in a subject comprising an effective amount of CLQ, CLBQ14, or CLCQ, or analogs or derivatives thereof, or a combination thereof, wherein the composition inhibits or disrupts the physical interaction of angiotensin converting enzyme 2 (ACE2) receptor with the Spike (S) glycoprotein of SARS-CoV-2, thereby inhibiting or reducing viral infectivity. Disclosed herein is a composition for inhibiting or ameliorating a SARS-CoV-2 infection in a subject comprising an effective amount of CLQ, CLBQ14, or CLCQ, or analogs or derivatives thereof, or a combination thereof, wherein the composition inhibits or disrupts the physical interaction of angiotensin converting enzyme 2 (ACE2) with the Spike (S) glycoprotein of SARS-CoV-2, thereby inhibiting or ameliorating a SARS-CoV-2 infection. Disclosed herein is a composition for inhibiting or reducing viral entry into cells of a subject comprising an effective amount of CLQ, CLBQ14, or CLCQ, or analogs or derivatives thereof, or a combination thereof, and wherein the composition inhibits or disrupts they physical interactions of angiotensin converting enzyme 2 (ACE2) and the Spike (S) glycoprotein of SARS-CoV-2, thereby inhibiting or reducing viral entry into cells of the subject.

In an aspect, a disclosed composition comprising one or more compounds belonging to the 8-hydroxyquinoline structural class or a disclosed composition comprising CLQ, CLBQ14, or CLCQ, or analogs or derivatives thereof, or a combination thereof can inhibit or disrupt the physical interaction of angiotensin converting enzyme 2 (ACE2) with the Spike (S) glycoprotein of SARS-CoV-2. In an aspect, a disclosed composition comprising one or more compounds belonging to the 8-hydroxyquinoline structural class or a disclosed composition comprising CLQ, CLBQ14, or CLCQ, or analogs or derivatives thereof, or a combination thereof can inhibit or reduce viral infectivity. In an aspect, a disclosed composition comprising one or more compounds belonging to the 8-hydroxyquinoline structural class or a disclosed composition comprising CLQ, CLBQ14, or CLCQ, or analogs or derivatives thereof, or a combination thereof can inhibit or ameliorate a SARS-CoV-2 infection. In an aspect, a disclosed composition comprising one or more compounds belonging to the 8-hydroxyquinoline structural class or a disclosed composition comprising CLQ, CLBQ14, or CLCQ, or analogs or derivatives thereof, or a combination thereof can inhibit or reduce viral entry into cells of the subject.

In an aspect, the receptor binding domain (RBD) of the Spike glycoprotein can bind to the metallopeptidase domain (MPD) of the ACE2 receptor.

In an aspect, a disclosed composition comprising CLQ, CLBQ14, or CLCQ, or analogs or derivatives thereof, or a combination thereof can comprise an effective amount of zinc chloride.

CLQ, CLBQ14, CLCQ, and analogs or derivatives thereof are known to the art and are discussed herein. Pharmaceutically acceptable diluents, carriers, excipients, stabilizers, and combinations thereof are known to the art and are discussed herein.

In an aspect, a disclosed composition comprising CLQ, CLBQ14, or CLCQ, or analogs or derivatives thereof, or a combination thereof can comprise one or more active agents, one or more biologically active agents, one or more pharmaceutically active agents, one or more immune-based therapeutic agents, one or more clinically approved agents, or a combination thereof. Biologically active agents are described herein and are known to the art. Pharmaceutically active agents are described herein and are known to the art. Immune-based therapeutic agents are described herein and are known to the art. Clinically approved active agents can comprise one or more FDA-approved active agents regardless of whether an active agent is a biologically active agent, a pharmaceutically active agent, or an immune-based therapeutic agent.

In an aspect, a disclosed composition comprising CLQ, CLBQ14, or CLCQ, or analogs or derivatives thereof, or a combination thereof can comprise (i) one or more active agents, (ii) one or more biologically active agents, (iii) one or more pharmaceutically active agents, (iv) one or more immune-based therapeutic agents, (v) one or more clinically approved agents, or (vi) a combination thereof. In an aspect, a disclosed composition comprising CLQ, CLBQ14, or CLCQ, or analogs or derivatives thereof, or a combination thereof can comprise (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof.

In an aspect, a disclosed composition comprising CLQ, CLBQ14, or CLCQ, or analogs or derivatives thereof, or a combination thereof may be administered in various formats, such as tablet, capsule, syrup, dry powder sachets, inhalation solution/nebulization, drops, ampules, suppository, creams or ointments. For example, the composition may be administered in a tablet format. Tablets may be formulated for controlled release formulation, delayed release formulation, extended release formulation, sustained release formulation, pulsatile release formulation, or mixed immediate release formulation. Tablets may be effervescent. The composition may be administered in a capsule format. Capsules may be formulated for immediate release or sustained release, as examples. Capsules may be hard capsules or and soft capsules. Solution formats may be oil based, aqueous, or emulsions.

In various embodiments, the composition comprising CLQ, CLBQ14, and/or CLCQ, or analogs or derivatives thereof, or a combination thereof, may be administered via any suitable administration route. Example administration routes include parenteral administration, which may include intramuscular, intraarterial, or intravenous, as examples. Example administration routes include nonparenteral administration, such as oral, rectal, vaginal, nasal, mucosal, percutaneous, transdermal, or ophthalmic, as examples.

The composition comprising CLQ, CLBQ14, and/or CLCQ, or analogs or derivatives thereof, or a combination thereof, may be administered in a suitable dosage format, via a suitable route of administration, such as any of those identified above, and in an effective daily dose to inhibit or ameliorate a SARS-CoV-2 infection, such as by any mechanism identified herein. The daily dose may be between 30 mg up to 2,000 mg. Example daily dosages may include greater than 200 mg, greater than 400 mg, greater than 500 mg, greater than 600 mg, greater than 700 mg, greater than 800 mg, greater than 900 mg, greater than 1000 mg, between 50 mg and 100 mg, between 100 mg and 200 mg, between 150 mg and 300 mg, between 200 mg and 1000 mg, between 500 mg and 1500 mg, between 450 mg and 1200 mg, between 500 mg and 2000 mg, between 1000 mg and 2000 mg, or any range between 30 mg and 2000 mg. The composition will typically be administered once daily, twice daily, or three times daily; however, additional administrations may be used.

In an aspect, a disclosed composition can be administered to a subject. In an aspect, a subject can be a human. In an aspect, a human subject can be a participant in a clinical trial. In an aspect, a subject can be a human or a non-human primate diagnosed with or suspected of having a SARS-CoV-2 infection.

In an aspect, a disclosed composition comprising CLQ, CLBQ14, or CLCQ, or analogs or derivatives thereof, or a combination thereof can be administered to a subject having one or more comorbidities. In an aspect, a disclosed composition comprising CLQ, CLBQ14, or CLCQ, or analogs or derivatives thereof, or a combination thereof can comprise one or more active agents to treat or ameliorate one or more comorbidities. Comorbidities are known to the art and are discussed herein.

D. Benzylamine Structural Class

SARS-CoV-2 enters the host cells through two main pathways, both involving key interactions between viral envelope-anchored spike glycoprotein and the host receptor angiotensin-converting enzyme 2 (ACE2). AMB has been available as an over the counter mucolytic medication since 1970s and has been proven to be safe and well tolerated in adults and children. Through focused search for clinically approved drugs to target the coronavirus pathway for cell entry, we discovered that Ambroxol hydrochloride (AMB) exerts superior pharmacological efficacy at the molecular and cellular level against SARS-CoV-2 viral infection. More excitingly, nano- to micromolar concentrations of AMB effectively: (1) blocks the pathway of SARS-CoV-2 entry into human cells via modulating ACE2's interaction with receptor binding domain protein of SARS-CoV-2; (2) inhibit SARS-CoV-2 infection-induced cytopathic effect; and (3) protect ACE2 exopeptidase function, while modulating its interaction with SARS-CoV-2 Spike glycoprotein, thus avoiding potential non-target cardiac toxicities observed in other ACE2 modulating agents. In various embodiments, one or both of AMB or its progenitor, bromhexine hydrochloride (BHH) may be administered to a subject to (1) block the pathway of SARS-CoV-2 entry into human cells via modulating ACE2's interaction with receptor binding domain protein of SARS-CoV-2; (2) inhibit SARS-CoV-2 infection-induced cytopathic effect; and/or (3) protect ACE2 exopeptidase function, while modulating its interaction with SARS-CoV-2 Spike glycoprotein, thus avoiding potential non-target cardiac toxicities observed in other ACE2 modulating agents. AMB has shown better clinical safety and pharmacologic profile compared to BHH historically. AMB accumulates in the lungs (a key site for SARS-CoV-2 viral replication), increases surfactant production, inhibits autophagy and reduces the production of certain inflammatory cytokines by bronchoalveolar macrophages. As described herein AMB and/or BHH may be administered to a subject for the treatment of moderate COVID-19 to effectively inhibit SARS-CoV-2 pathways, and therefore results in decreased viral load, reduced inflammation, reduced rate of hospitalization and improved clinical outcomes in moderate COVID-19 subjects.

Effective therapeutic interventions against SARS-CoV-2 infection require inhibiting essential viral entry and/or post-entry pathways by targeting viral enzymes or host receptors. The emergence of SARS-CoV-2 variants with mutations on the viral genes have made it more imperative to discover therapeutics that targets the host receptors for COVID-19 treatment. Benzylamine structural class targets two critical host entry receptors: Angiotensin-converting enzyme-2 (ACE2) and tyrosine-protein kinase receptor (AXL) for SARS-CoV-2 entry into the human cells.

According to various embodiments, an effective amount of Ambroxol Hydrochloride (AMB) may be administered to a subject to therein target the interaction between RBD and ACE2, without inactivating the exopeptidase activity of human Angiotensin-Converting Enzyme-2 (ACE2).

ACE2, a membrane-bound metalloprotease is an essential cellular receptor for SARS-CoV-2 entry into host cells. It is an important component in the Renin-Angiotensin system converting Angiotensin II (Ang II) to Angiotensin 1-7, a potent vasopressor. Although ACE2 facilitates viral entry, it provides defense against acute lung damage, indicating that the ACE2/Ang 1-7 pathway must be carefully manipulated to reduce SARS-CoV-2 induced lung injuries.

Applicant has discovered that Ambroxol hydrochloride (AMB) and its progenitor Bromhexine hydrochloride (BHH) inhibits the interaction of SARS-CoV-2 spike protein receptor-binding domain (RBD) with human recombinant ACE2 (rhACE2) in a nano to micro molar range thereby blocking its entry into human cells. Applicant has further discovered that AMB targets the interaction between RBD and rhACE2, without inactivating the exopeptidase activity of rhACE2. Our findings reveal that AMB binding to rhACE2 may preserving its physiological function, unlike BHH which inhibits rhACE2 exopeptidase activity at high concentrations (Tables 1(a), 1(b)). Thus, potentially prevents non-target cardiac toxicities observed in other ACE2 modulating drugs.

According to various embodiments, an effective amount of Ambroxol Hydrochloride (AMB) and/or Bromhexine Hydrochloride may be administered to a subject to therein inhibit the Interaction between Severe Acute Respiratory Syndrome Coronavirus 2 Spike Protein's N-Terminal Binding Domain and Tyrosine-Protein kinase Receptor (AXL).

AXL is a plasma membrane associated with the Tyro3/Axl/Mer (TAM) family: a group of tyrosine kinase receptors that mediate apoptotic cells' clearance and regulate innate immunity response. Previously, AXL was identified as a receptor for the Zika virus, allowing viral entry into the human glial cells and facilitating infection by downregulating interferon signaling. It also serves as an entry factor for the dengue virus and facilitates the entry of filoviruses. Studies have identified AXL as an additional critical entry receptor that promotes the entry of SARS-CoV-2 into cells of the respiratory system. The interaction of the N-terminal domain (NTD) of SARS-CoV-2 Spike protein with AXL facilitates the viral entry into the human cells. In this study, we discovered for the first time that AMB and BHH both inhibit the interaction of recombinant AXL with the NTD of the spike protein in the micromolar range (Table 2).

Inhibition of the two critical viral entry pathways into host cells represents a promising therapeutic possibility to combat SARS-CoV-2 infection. Therefore, compounds such as AMB and BHH, with potent efficacy, excellent safety and pharmacologic profile along with their availability and affordability makes this pharmacophore promising candidates for drug repurposing as a possible prophylactical and or treatment options against COVID-19 infection.

TABLE 1(a)

Effect of Bromhexine Hydrochloride (BHH) and Ambroxol Hydrochloride (AMB) on ACE2 Exopeptidase Activity: Percent Activity

| Concentration (uM) | Percent Activity (%) | |
|---|---|---|
| | BHH | AMB |
| 500 | −6.6 | 141.0 |
| 250 | −6.7 | 144.7 |
| 100 | −6.2 | 156.9 |
| 50 | 2.7 | 157.1 |
| 10 | 104.6 | 159.9 |
| 1 | 114.7 | 152.3 |
| 0.1 | 111.3 | 148.7 |

TABLE 1(b)

Effect of Bromhexine Hydrochloride (BHH) and Ambroxol Hydrochloride (AMB) on the ACE2 Exopeptidase Activity: Percent Inhibition

| Concentration (uM) | Percent Inhibition (%) | |
|---|---|---|
| | BHH | AMB |
| 500 | 106.6 | −41.0 |
| 250 | 106.7 | −44.7 |
| 100 | 106.2 | −56.9 |
| 50 | 97.3 | −57.1 |
| 10 | −4.6 | −59.9 |
| 1 | −14.7 | −52.3 |
| 0.1 | −11.3 | −48.7 |

TABLE 2

Effect of Bromhexine Hydrochloride (BHH) and Ambroxol Hydrochloride (AMB) on the interaction between rhAXL and SARS-CoV-2 Spike (NTD) protein Interaction.

According to various embodiments, an effective amount of Ambroxol Hydrochloride (AMB) and/or Bromhexine Hydrochloride may be administered to a subject to therein blocks the entry of SARS-CoV-2 spike pseudotyped lentivirus into human cells.

To date, there are rapidly spreading new variants with mutations on the viral genes of SARS-CoV-2. Successful intervention measures are needed now more than ever to contain the pandemic. Inhibiting critical viral entry and post-entry processes by targeting viral enzymes or host receptors is necessary to develop effective therapeutic interventions against SARS-CoV-2 infection. Therefore, Applicant has also focused research on blocking the first step of viral fusion of SARS-CoV-2 spike protein receptor-binding domain (RBD) with host receptor; Angiotensin-converting enzyme 2 (ACE2) and thereby prevent the cellular entry of SARS-CoV-2 into the human cells.

Applicant tested the ability of Ambroxol Hydrochloride (AMB) and Bromhexine Hydrochloride (BHH) to inhibit the cellular entry of the SARS-CoV-2 spike pseudotyped lentivirus in a low micromolar range. Briefly, Spike (SARS-CoV-2) pseudotyped lentivirus containing luciferase reporter gene was purchased from BPS Bioscience (Catalog no 79942, San Diego, CA). HEK293 cells with stable expression of full-length ACE2 were seeded at a density of 7500 cells per well into a white 96-well cell culture microplate. On day two, pseudotyped lentivirus was preincubated with AMB and BHH at concentrations ranging from 100, 50, 25, and M for 30 minutes at room temperature (RT); the reaction mixture was then added to the cells. After 48 hours on day four, luciferase activity was measured by adding 50 μl Luciferase reagent (BPS Bioscience, catalog no. 60690) for 30 min at RT luminescence was measured with Spectra max ID3 (molecular devices). The measured luminescence signal was directly proportional to the amount of pseudo-typed lentivirus successfully transduced into the cells. Data are presented as percent inhibition of entry of pseudo-type lentivirus into the HEK293-ACE2 cells. All experiments were done in duplicates and were repeated twice. Taken together, our in vitro data on SARS-CoV-2 spike pseudo-typed lentivirus suggest that administration of AMB and BHH may be effective and safe prophylaxis or treatment for SARS-CoV-2 infection (Tables 1(a), 1(b)).

TABLE 3

Effect of Ambroxol Hydrochloride (AMB) and Bromhexine Hydrochloride (BHH) on the fusion of SARS-CoV-2 spike pseudotyped lentivirus with HEK293-ACE2 Cells

| Concentration (μM) | Percent Inhibition % | | | |
|---|---|---|---|---|
| | BHH | BHH | AMB | AMB |
| 100 | 73 | 76 | 41 | 47 |
| 50 | 57 | 61 | 72 | 59 |
| 25 | 8 | 27 | 78 | 64 |
| 10 | −195 | −81 | 86 | 55 |

According to various embodiments, an effective amount of Ambroxol Hydrochloride (AMB) and/or Bromhexine Hydrochloride may be administered to a subject to block or affect entry of SARS-CoV-2 spike (B.1.617.2 Delta Variant) pseudotyped lentivirus into HEK293-ACE2 Cells.

Applicant Ambroxol Hydrochloride (AMB) and Bromhexine Hydrochloride against the newly emerged delta variant of SARSC0V-2. Briefly, Spike (B.1.617.2 Delta Variant) pseudo typed lentivirus containing luciferase reporter gene was purchased from BPS Bioscience (Catalog no 78215-1, San Diego, CA). HEK293 cells with stable expression of full-length ACE2 were seeded at a density of 7500 cells per well into a white 96-well cell culture microplate. On the same day, pseudo typed lentivirus was preincubated with AMB and BHH at concentrations ranging from 100, 50, 25, and 10 μM for 30 minutes at room temperature (RT); the reaction mixture was then added to the cells. After 48 hours on day four, luciferase activity was measured by adding 100 μl Luciferase reagent (BPS Bioscience, catalog no. 60690) for 30 min at RT luminescence was measured with Spectra max ID3 (molecular devices). The measured luminescence signal is directly proportional to the amount of pseudotyped lentivirus successfully transduced into the cells.

1. Methods Comprising the Benzylamine Structural Class

General Methods

Disclosed herein is a method comprising administering a composition comprising an effective amount of one or more compounds belonging to the benzylamine structural class; and inhibiting or ameliorating a SARS-CoV-2 infection. Disclosed herein is a method comprising administering a composition comprising an effective amount of AMB or BHH, or analogs or derivatives thereof, or a combination thereof, and inhibiting or ameliorating a SARS-CoV-2 infection. Disclosed herein is a method comprising administering a composition comprising an effective amount of one or more compounds belonging to the benzylamine structural class; administering one or more clinically approved active agents; and inhibiting or ameliorating a SARS-CoV-2 infection. Disclosed herein is a method comprising administering a composition comprising an effective amount of AMB or BHH, or analogs or derivatives thereof, or a combination thereof; administering one or more clinically approved active agents; and inhibiting or ameliorating a SARS-CoV-2 infection. Disclosed herein is a method comprising inhibiting or ameliorating a SARS-CoV-2 infection by administering a composition comprising one or more compounds belonging to the benzylamine structural class. Disclosed herein is a method comprising inhibiting or ameliorating a SARS-CoV-2 infection by administering a composition comprising an effective amount of AMB or BHH, or analogs or derivatives thereof, or a combination thereof. Disclosed herein is a method of inhibiting or ameliorating a SARS-CoV-2 infection comprising administering a composition comprising an effective amount of one or more compounds belonging to the benzylamine structural class, thereby inhibiting or ameliorating a SARS-CoV-2 infection. Disclosed herein is a method of inhibiting or ameliorating a SARS-CoV-2 infection comprising administering a composition comprising an effective amount of AMB or BHH, or analogs or derivatives thereof, or a combination thereof, thereby inhibiting or ameliorating a SARS-CoV-2 infection. Disclosed herein is a method of inhibiting or ameliorating a SARS-CoV-2 infection comprising prophylactically administering a composition comprising an effective amount of AMB or BHH, or analogs or derivatives thereof, or a combination thereof, and inhibiting or ameliorating a SARS-CoV-2 infection. Disclosed herein is a method of inhibiting or ameliorating a SARS-CoV-2 infection comprising prophylactically administering a composition comprising an effective amount of one or more compounds belonging to the benzylamine structural class; and inhibiting or ameliorating a SARS-CoV-2 infection.

The benzylamine structural class structural class is known to the art. The benzylamine structural class comprises at least Ambroxol hydrochloride (AMH) and bromhexine hydrochloride (BHH). For example, Ambroxol hydrochloride (AMH) is an aromatic amine that comprises the formula $C_{13}H_{19}Br_2ClN_2O$ and has a molecular weight of 414.56 g/mol. Bromhexine hydrochloride is the hydrochloride salt form of bromhexine. Bromhexine hydrochloride comprises the formula $C_{14}H_{21}Br_2ClN_2$ and has a molecular weight of 412.59 g/mol.

In an aspect, a disclosed method or a disclosed method of inhibiting or ameliorating a SARS-CoV-2 infection can comprise administering one or more active agents, one or more biologically active agents, one or more pharmaceutically active agents, one or more immune-based therapeutic agents, one or more clinically approved agents, or a combination thereof. Biologically active agents are described herein and are known to the art. Pharmaceutically active agents are described herein and are known to the art. Immune-based therapeutic agents are described herein and are known to the art. Clinically approved active agents can comprise one or more FDA-approved active agents regardless of whether an active agent is a biologically active agent, a pharmaceutically active agent, or an immune-based therapeutic agent.

In an aspect, a disclosed composition in a disclosed method or a disclosed method of inhibiting or ameliorating a SARS-CoV-2 infection can comprise can comprise (i) one or more active agents, (ii) one or more biologically active agents, (iii) one or more pharmaceutically active agents, (iv) one or more immune-based therapeutic agents, (v) one or more clinically approved agents, or (vi) a combination thereof. In an aspect, a disclosed method or a disclosed method of inhibiting or ameliorating a SARS-CoV-2 infection can comprise administering (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof. In an aspect, a disclosed composition in a disclosed method or a disclosed method of inhibiting or ameliorating a SARS-CoV-2 infection can comprise (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof.

In an aspect, a composition in a disclosed method or a disclosed method of inhibiting or ameliorating a SARS-CoV-2 infection can comprise a AMB and/or BHH, or analogs or derivatives thereof, or a combination thereof. The composition may be administered in various formats, such as tablet, capsule, syrup, dry powder sachets, inhalation solution/nebulization, drops, ampules, suppository, creams or ointments. For example, the composition may be administered in a tablet format. Tablets may be formulated for controlled release formulation, delayed release formulation, extended release formulation, sustained release formulation, pulsatile release formulation, or mixed immediate release formulation. Tablets may be effervescent. The composition may be administered in a capsule format. Capsules may be formulated for immediate release or sustained release, as examples. Capsules may be hard capsules or and soft capsules. Solution formats may be oil based, aqueous, or emulsions.

In various embodiments, the composition comprising AMB and/or BHH, or analogs or derivatives thereof, or a combination thereof, may be administered via any suitable administration route. Example administration routes include parenteral administration, which may include intramuscular, intraarterial, or intravenous, as examples. Example administration routes include nonparenteral administration, such as oral, rectal, vaginal, nasal, mucosal, percutaneous, transdermal, or ophthalmic, as examples.

The composition comprising AMB and/or BHH, or analogs or derivatives thereof, or a combination thereof, may be administered in a suitable dosage format, via a suitable route of administration, such as any of those identified above, and in an effective daily dose to inhibit or ameliorate a SARS- CoV-2 infection, such as by any mechanism identified herein. The daily dose may be between 30 mg up to 2,000 mg. Example daily dosages may include greater than 200 mg, greater than 400 mg, greater than 500 mg, greater than 600 mg, greater than 700 mg, greater than 800 mg, greater than 900 mg, greater than 1000 mg, between 50 mg and 100 mg, between 100 mg and 200 mg, between 150 mg and 300 mg, between 200 mg and 1000 mg, between 500 mg and 1500 mg, between 450 mg and 1200 mg, between 500 mg and 2000 mg, between 1000 mg and 2000 mg, or any range between 30 mg and 2000 mg. The composition will typically be administered once daily, twice daily, or three times daily; however, additional administrations may be used.

In one example, AMB and/or BHH is administered at a total daily dose of 240 mg, 480 mg or 960 mg, twice daily. The administration route may be oral. In one example, AMB and/or BHH is administered orally in a tablet or capsule.

In an aspect, a disclosed method or a disclosed method of inhibiting or ameliorating a SARS-CoV-2 infection can comprise repeating one or more steps.

In an aspect, a disclosed method or a disclosed method of inhibiting or ameliorating a SARS-CoV-2 infection can comprise identifying a subject having been diagnosed with or suspected of having a SARS-CoV-2 infection. As known to the art, a SARS-CoV-2 infection can be diagnosed and/or confirmed through various tests (such as, e.g., a PCR test or an antigen test).

In an aspect, a disclosed method or a disclosed method of inhibiting or ameliorating a SARS-CoV-2 infection can comprise identifying a subject having been diagnosed with or suspected of having a SARS-CoV-2 re-infection. As known to the art, a past SARS-CoV-2 infection can be diagnosed and/or confirmed through an antibody test. In an aspect, an antibody test (also known as serology testing) can check for Immunoglobulin G (IgG) antibody. In an aspect, a variety of factors can impact the results from an antibody test in a disclosed method (e.g., the time the test was taken after experiencing symptoms, the absence of or time since exposure to the virus, or the lack of an adequate immune response, which can be due to conditions or treatments that suppress immune function).

In an aspect, the administering step of a disclosed method or a disclosed method of inhibiting or ameliorating a SARS-CoV-2 infection can comprise administering to a subject. In an aspect, a subject can be a human. In an aspect, a human subject can be a participant in a clinical trial. In an aspect, a subject can be a human or a non-human primate diagnosed with or suspected of having a SARS-CoV-2 infection.

In an aspect, a disclosed method or a disclosed method of inhibiting or ameliorating a SARS-CoV-2 infection can comprise identifying and/or characterizing one or more comorbidities in a subject. In an aspect of a disclosed method, a subject can have one or more comorbidities. Comorbidities are known to the art and can comprise cancer, chronic kidney disease, COPD (chronic obstructive pulmonary disease), an immunocompromised state (weakened immune system) from a solid organ transplant or from a blood or bone marrow transplant, obesity (body mass index [BMI] of 30 or higher), heart conditions (such as, e.g., heart failure, coronary artery disease, or cardiomyopathies), sickle cell disease, type 1 diabetes mellitus or type 2 diabetes mellitus, asthma, cerebrovascular disease, cystic fibrosis, hypertension or high blood pressure, immune deficiencies, HIV, use of corticosteroids, or use of other immune weakening medicines, neurologic conditions, liver disease, pregnancy, pulmonary fibrosis (having damaged or scarred lung tissues), a history of smoking, and thalassemia (a type of blood disorder).

In an aspect, a disclosed method or a disclosed method of inhibiting or ameliorating a SARS-CoV-2 infection can comprise treating or ameliorating one or more comorbidities in a subject. For example, in an aspect, a disclosed method or a disclosed method of inhibiting or ameliorating a SARS-CoV-2 infection can comprise (i) administering one or more active agents to treat or ameliorate one or more comorbidities, (ii) administering one or more active agents to treat or ameliorate the same comorbidity, (iii) administering one or more active agents to treat or ameliorate different comorbidities (e.g., an active agent for type 2 diabetes and a different active agent for hypertension), or (iv) a combination thereof. In an aspect, administering an active agent to treat or ameliorate one or more comorbidities can occur prior to, concurrently with, or after the administering of a disclosed composition. In an aspect, a disclosed method or a disclosed method of inhibiting or ameliorating a SARS-CoV-2 infection can comprise repeating the administering step of an active agent to treat or ameliorate one or more comorbidities.

In an aspect, a disclosed method or a disclosed method of inhibiting or ameliorating a SARS-CoV-2 infection can comprise modifying or altering one or more steps of a disclosed method. For example, in an aspect, a disclosed method or a disclosed method of inhibiting or ameliorating a SARS-CoV-2 infection can comprise modifying or altering an administering step. In an aspect, an administering step can be modified or altered, for example, by changing the route of administration, or changing the dose of a disclosed composition, or changing the timing of administration, or changing the frequency of the administration, or a combination thereof. In an aspect, altering or modifying one or more steps of a disclosed method or a disclosed method of inhibiting or ameliorating a SARS-CoV-2 infection can be based on the identification and/or characterization of one or more comorbidities in a subject.

In an aspect, a disclosed method or a disclosed method of inhibiting or ameliorating a SARS-CoV-2 infection can comprise modifying or altering the administering step of an active agent to treat or ameliorate one or more comorbidities.

In an aspect, a disclosed method or a disclosed method of inhibiting or ameliorating a SARS-CoV-2 infection can comprise determining, measuring, and/or ascertaining the presence and/or severity of an infection, such as, for example, a SARS-CoV-2 infection, a bacterial infection, a viral infection, a fungal infection, or a combination thereof. Methods and techniques used to determine, measure, and/or ascertain the presence and/or severity of an infection such as a SARS-CoV-2 infection are typically known to the medical arts.

In an aspect, a disclosed method or a disclosed method of inhibiting or ameliorating a SARS-CoV-2 infection can comprise monitoring a subject's response to the administration of a disclosed composition comprising AMB or BHH, or analogs or derivatives thereof, or a combination thereof. In an aspect of a disclosed method, a monitoring step can be repeated one or more times. In an aspect, a disclosed method or a disclosed method of inhibiting or ameliorating a SARS-CoV-2 infection can comprise monitoring a subject's response to the administration of a disclosed composition comprising (i) AMB or BHH, or analogs or derivatives thereof, or a combination thereof and (ii) one or more disclosed active agents, one or more biologically active agents, one or more pharmaceutically active agents, one or more immune-based therapeutic agents, one or more clinically approved agents, or a combination thereof. In an aspect of a disclosed method, a monitoring step can be repeated one or more times.

Methods and techniques to monitor a subject's response to a disclosed method can comprise qualitative (or subjective) means as well as quantitative (or objective) means. In an aspect, qualitative means (or subjective means) can comprise a subject's own perspective. For example, a subject can report how he/she is feeling, whether he/she has experienced improvements and/or setbacks, whether he/she has experienced an amelioration of one or more symptoms, or a combination thereof. In an aspect, quantitative means (or objective means) can comprise methods and techniques that include, but are not limited to, the following: (i) fluid analysis (e.g., tests of a subject's fluids including but not limited to aqueous humor and vitreous humor, bile, blood, blood serum, breast milk, cerebrospinal fluid, cerumen (earwax), digestive fluids, endolymph and perilymph, female ejaculate, gastric juice, mucus (including nasal drainage and phlegm), peritoneal fluid, pleural fluid, saliva, sebum (skin oil), semen, sweat, synovial fluid, tears, vaginal secretion, vomit, and urine), (ii) imaging (e.g., ordinary x-rays, ultrasonography, radioisotope (nuclear) scanning, computed tomography (CT), magnetic resonance imaging (MRI), positron emission tomography (PET), and angiography), (iii) endoscopy (e.g., laryngoscopy, bronchoscopy, esophagoscopy, gastroscopy, GI endoscopy, coloscopy, cystoscopy, hysteroscopy, arthroscopy, laparoscopy, mediastinoscopy, and thoracoscopy), (iv) analysis of organ activity (e.g., electrocardiography (ECG), electroencephalography (EEG), and pulse oximetry), (v) biopsy (e.g., removal of tissue samples for microscopic evaluation), and (vi) genetic testing.

In an aspect, a disclosed method or a disclosed method of inhibiting or ameliorating a SARS-CoV-2 infection can comprise obtaining a disclosed compound (e.g., AMB or BHH, or an analog or derivative thereof), obtaining a disclosed composition, obtaining a disclosed formulation comprising a disclosed composition, obtaining one or more active agents, one or more biologically active agents, pharmaceutically active agents, immune-based therapeutic agents, clinically approved agents, or obtaining a combination thereof.

In an aspect, a disclosed method or a disclosed method of inhibiting or ameliorating a SARS-CoV-2 infection can comprise preparing a disclosed compound (e.g., AMB or BHH, or an analog or derivative thereof) or preparing a disclosed composition comprising CLQ, CLBQ14, or CLCQ, or analogs or derivatives thereof, or a combination thereof. In an aspect, a disclosed method or a disclosed method of inhibiting or ameliorating a SARS-CoV-2 infection can comprise (1) preparing a disclosed composition comprising AMB or BHH, or analogs or derivatives thereof, or a combination thereof, and (2) preparing (i) one or more active agents, (ii) one or more biologically active agents, (iii) one or more pharmaceutically active agents, (iv) one or more immune-based therapeutic agents, (v) one or more clinically approved agents, or (vi) a combination thereof. In an aspect, a disclosed method or a disclosed method of inhibiting or ameliorating a SARS-CoV-2 infection can comprise preparing one or more active agents, one or more biologically active agents, one or more pharmaceutically active agents, one or more immune-based therapeutic agents, one or more clinically approved agents, or a combination thereof. In an aspect, a disclosed method or a disclosed method of inhibiting or ameliorating a SARS-CoV-2 infection can comprise preparing a disclosed composition comprising (i) AMB or BHH, or analogs or derivatives thereof, or a combination thereof, and (ii) one or more active agents, biologically active agents, pharmaceutically active agents, immune-based therapeutic agents, clinically approved agents, or a combination thereof.

i. Method of Inhibiting or Ameliorating One or More SARS-CoV-2 Infection Induced Cytopathic Effects Disclosed herein is a method comprising administering a composition comprising an effective amount of AMB or BHH, or analogs or derivatives thereof, or a combination thereof, and inhibiting or ameliorating one or more SARS-CoV-2 infection induced cytopathic effects. Disclosed herein is a method comprising inhibiting or ameliorating one or more SARS-CoV-2 infection induced cytopathic effects by administering a composition comprising an effective amount of AMB or BHH, or analogs or derivatives thereof, or a combination thereof. Disclosed herein is a method of inhibiting or ameliorating one or more SARS-CoV-2 infection induced cytopathic effects comprising administering a composition comprising an effective amount of AMB or BHH, or analogs or derivatives thereof, or a combination thereof. Disclosed herein is a method of inhibiting or ameliorating one or more SARS-CoV-2 infection induced cytopathic effects in a subject comprising administering to a subject a composition comprising an effective amount of AMB or BHH, or analogs or derivatives thereof, or a combination thereof, and inhibiting or ameliorating one or more SARS-CoV-2 infection induced cytopathic effects in the subject. Disclosed herein is a method of inhibiting or ameliorating one or more SARS-CoV-2 infection induced cytopathic effects in a subject comprising inhibiting or ameliorating one or more SARS-CoV-2 infection induced cytopathic effects in the subject by administering to a subject a composition comprising an effective amount of AMB or BHH, or analogs or derivatives thereof, or a combination thereof.

In an aspect, a disclosed method or a disclosed method of inhibiting or ameliorating one or more SARS-CoV-2 infection induced cytopathic effects can comprise administering one or more active agents, one or more biologically active agents, one or more pharmaceutically active agents, one or more immune-based therapeutic agents, one or more clinically approved agents, or a combination thereof. Biologically active agents are described herein and are known to the art. Pharmaceutically active agents are described herein and are known to the art. Immune-based therapeutic agents are described herein and are known to the art. Clinically approved active agents can comprise one or more FDA-approved active agents regardless of whether an active agent is a biologically active agent, a pharmaceutically active agent, or an immune-based therapeutic agent.

In an aspect, a disclosed method or a disclosed method of inhibiting or ameliorating one or more SARS-CoV-2 infection induced cytopathic effects can comprise (i) one or more active agents, (ii) biologically active agents, (iii) one or more pharmaceutically active agents, (iv) one or more immune-based therapeutic agents, (v) one or more clinically approved agents, or (vi) a combination thereof. In an aspect, a disclosed method or a disclosed method of inhibiting or ameliorating one or more SARS-CoV-2 infection induced cytopathic effects can comprise administering (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof. In an aspect, a disclosed method or a disclosed method of inhibiting or ameliorating one or more SARS-CoV-2 infection induced cytopathic effects can comprise (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof.

In an aspect, a composition in a disclosed method or a disclosed method of inhibiting or ameliorating one or more SARS-CoV-2 infection induced cytopathic effects can comprise AMB and/or BHH, or analogs or derivatives thereof, or a combination thereof. The composition may be administered in various formats, such as tablet, capsule, syrup, dry powder sachets, inhalation solution/nebulization, drops, ampules, suppository, creams or ointments. For example, the composition may be administered in a tablet format. Tablets may be formulated for controlled release formulation, delayed release formulation, extended release formulation, sustained release formulation, pulsatile release formulation, or mixed immediate release formulation. Tablets may be effervescent. The composition may be administered in a capsule format. Capsules may be formulated for immediate release or sustained release, as examples. Capsules may be hard capsules or and soft capsules. Solution formats may be oil based, aqueous, or emulsions.

In various embodiments, the composition comprising AMB and/or BHH, or analogs or derivatives thereof, or a combination thereof, may be administered via any suitable administration route. Example administration routes include parenteral administration, which may include intramuscular, intraarterial, or intravenous, as examples. Example administration routes include nonparenteral administration, such as oral, rectal, vaginal, nasal, mucosal, percutaneous, transdermal, or ophthalmic, as examples.

The composition comprising AMB and/or BHH, or analogs or derivatives thereof, or a combination thereof, may be administered in a suitable dosage format, via a suitable route of administration, such as any of those identified above, and in an effective daily dose to inhibit or ameliorate a SARS-CoV-2 infection, such as by any mechanism identified herein. The daily dose may be between 30 mg up to 2,000 mg. Example daily dosages may include greater than 200 mg, greater than 400 mg, greater than 500 mg, greater than 600 mg, greater than 700 mg, greater than 800 mg, greater than 900 mg, greater than 1000 mg, between 50 mg and 100 mg, between 100 mg and 200 mg, between 150 mg and 300 mg, between 200 mg and 1000 mg, between 500 mg and 1500 mg, between 450 mg and 1200 mg, between 500 mg and 2000 mg, between 1000 mg and 2000 mg, or any range between 30 mg and 2000 mg. The composition will typically be administered once daily, twice daily, or three times daily; however, additional administrations may be used.

In one example, AMB and/or BHH is administered at a total daily dose of 240 mg, 480 mg or 960 mg, twice daily. The administration route may be oral. In one example, AMB and/or BHH is administered orally in a tablet or capsule.

In an aspect, a disclosed method or a disclosed method of inhibiting or ameliorating one or more SARS-CoV-2 infection induced cytopathic effects can further comprise repeating one or more steps.

In an aspect, a disclosed method or a disclosed method of inhibiting or ameliorating one or more SARS-CoV-2 infection induced cytopathic effects can comprise identifying a subject having been diagnosed with or suspected of having a SARS-CoV-2 infection. As known to the art, a SARS-CoV-2 infection can be diagnosed and/or confirmed through various tests (such as, e.g., a PCR test or an antigen test). In an aspect, a disclosed method or a disclosed method of inhibiting or ameliorating one or more SARS-CoV-2 infection induced cytopathic effects can comprise identifying a subject having been diagnosed with or suspected of having a SARS-CoV-2 re-infection. As known to the art, a past SARS-CoV-2 infection can be diagnosed and/or confirmed through an antibody test. In an aspect, an antibody test (also known as serology testing) can check for Immunoglobulin G (IgG) antibody. In an aspect, a variety of factors can impact the results from an antibody test in a disclosed method (e.g., the time the test was taken after experiencing symptoms, the absence of or time since exposure to the virus, or the lack of an adequate immune function.

In an aspect, the administering step of a disclosed method or a disclosed method of inhibiting or ameliorating one or more SARS-CoV-2 infection induced cytopathic effects can comprise administering to a subject. In an aspect, a subject can be a human. In an aspect, a human subject can be a participant in a clinical trial. In an aspect, a subject can be a human or non-human primate diagnosed with or suspected of having a SARS-CoV-2 infection.

In an aspect, a disclosed method or a disclosed method of inhibiting or ameliorating one or more SARS-CoV-2 infection induced cytopathic effects can comprise identifying and/or characterizing one or more comorbidities in a subject. In an aspect of a disclosed method, a subject can have one or more comorbidities. Comorbidities are known to the art and can comprise cancer, chronic kidney disease, COPD (chronic obstructive pulmonary disease), an immunocompromised state (weakened immune system) from a solid organ transplant or from a blood or bone marrow transplant, obesity (body mass index [BMI] of 30 or higher), heart conditions (such as, e.g., heart failure, coronary artery disease, or cardiomyopathies), sickle cell disease, type 1 diabetes mellitus or type 2 diabetes mellitus, asthma, cerebrovascular disease, cystic fibrosis, hypertension or high blood pressure, immune deficiencies, HIV, use of corticosteroids, or use of other immune weakening medicines, neurologic conditions, liver disease, pregnancy, pulmonary fibrosis (having damaged or scarred lung tissues), a history of smoking, and thalassemia (a type of blood disorder).

In an aspect, a disclosed method or a disclosed method of inhibiting or ameliorating one or more SARS-CoV-2 infection induced cytopathic effects can comprise treating or ameliorating one or more comorbidities in a subject. For example, in an aspect, a disclosed method or a disclosed method of inhibiting or ameliorating one or more SARS-CoV-2 infection induced cytopathic effects can comprise (i) administering one or more active agents to treat or ameliorate one or more comorbidities, (ii) administering one or more active agents to treat or ameliorate the same comorbidity, (iii) administering one or more active agents to treat or ameliorate different comorbidities (e.g., an active agent for type 2 diabetes and a different active agent for hypertension), or (iv) a combination thereof. In an aspect, administering an active agent to treat or ameliorate one or more comorbidities can occur prior to, concurrently with, or after the administering of a disclosed composition. In an aspect, a disclosed method or a disclosed method of inhibiting or ameliorating one or more SARS-CoV-2 infection induced cytopathic effects can comprise repeating the administering step of an active agent to treat or ameliorate one or more comorbidities.

In an aspect, a disclosed method or a disclosed method of inhibiting or ameliorating one or more SARS-CoV-2 infection induced cytopathic effects can comprise modifying or altering one or more steps of a disclosed method. For example, in an aspect, a disclosed method or a disclosed method of inhibiting or ameliorating one or more SARS-CoV-2 infection induced cytopathic effects can comprise modifying or altering an administering step. In an aspect, an administering step can be modified or altered, for example, by changing the route of administration, or changing the dose of a disclosed composition, or changing the timing of administration, or changing the frequency of the administration, or a combination thereof.

In an aspect, altering or modifying one or more steps of a disclosed method or a disclosed method of inhibiting or ameliorating one or more SARS-CoV-2 infection induced cytopathic effects, such as, for example, an administering step, can be based on the identification and/or characterization of one or more comorbidities in a subject. In an aspect a disclosed method or a disclosed method of inhibiting or ameliorating one or more SARS-CoV-2 infection induced cytopathic effects can comprise modifying or altering the administering step of an active agent to treat or ameliorate one or more comorbidities.

In an aspect, a disclosed method or a disclosed method of inhibiting or ameliorating one or more SARS-CoV-2 infection induced cytopathic effects can comprise determining, measuring, and/or ascertaining the presence and/or severity of an infection, such as, for example, a SARS-CoV-2 infection, a bacterial infection, a viral infection, a fungal infection, or a combination thereof. Methods and techniques used to determine, measure, and/or ascertain the presence and/or severity of an infection such as a SARS-CoV-2 infection are typically known to the medical arts.

In an aspect, a disclosed method or a disclosed method of inhibiting or ameliorating one or more SARS-CoV-2 infection induced cytopathic effects can comprise monitoring a subject's response to the administration of a disclosed composition comprising AMB or BHH, or analogs or derivatives thereof, or a combination thereof. In an aspect of a disclosed method or a disclosed method of inhibiting or ameliorating one or more SARS-CoV-2 infection induced cytopathic effects, a monitoring step can be repeated one or more times.

In an aspect, a disclosed method or a disclosed method of inhibiting or ameliorating one or more SARS-CoV-2 infection induced cytopathic effects can comprise monitoring a subject's response to the administration of a disclosed composition comprising (i) AMB or BHH, or analogs or derivatives thereof, or a combination thereof and (ii) one or more disclosed active agents, one or more biologically active agents, one or more pharmaceutically active agents, one or more immune-based therapeutic agents, one or more clinically approved agents, or a combination thereof. In an aspect of a disclosed method or a disclosed method of inhibiting or ameliorating one or more SARS-CoV-2 infection induced cytopathic effects, a monitoring step can be repeated one or more times.

Methods and techniques to monitor a subject's response to a disclosed method or a disclosed method of inhibiting or ameliorating one or more SARS-CoV-2 infection induced cytopathic effects can comprise qualitative (or subjective) means as well as quantitative (or objective) means. In an aspect, qualitative means (or subjective means) can comprise a subject's own perspective. For example, a subject can report how he/she is feeling, whether he/she has experienced improvements and/or setbacks, whether he/she has experienced an amelioration or an intensification of one or more symptoms, or a combination thereof. In an aspect, quantitative means (or objective means) can comprise methods and techniques that include, but are not limited to, the following: (i) fluid analysis (e.g., tests of a subject's fluids including but not limited to aqueous humor and vitreous humor, bile, blood, blood serum, breast milk, cerebrospinal fluid, cerumen (earwax), digestive fluids, endolymph and perilymph, female ejaculate, gastric juice, mucus (including nasal drainage and phlegm), peritoneal fluid, pleural fluid, saliva, sebum (skin oil), semen, sweat, synovial fluid, tears, vaginal secretion, vomit, and urine), (ii) imaging (e.g., ordinary x-rays, ultrasonography, radioisotope (nuclear) scanning, computed tomography (CT), magnetic resonance imaging (MRI), positron emission tomography (PET), and angiography), (iii) endoscopy (e.g., laryngoscopy, bronchoscopy, esophagoscopy, gastroscopy, GI endoscopy, coloscopy, cystoscopy, hysteroscopy, arthroscopy, laparoscopy, mediastinoscopy, and thoracoscopy), (iv) analysis of organ activity (e.g., electrocardiography (ECG), electroencephalography (EEG), and pulse oximetry), (v) biopsy (e.g., removal of tissue samples for microscopic evaluation), and (vi) genetic testing.

In an aspect, a disclosed method or a disclosed method of inhibiting or ameliorating one or more SARS-CoV-2 infection induced cytopathic effects can comprise obtaining a disclosed compound (e.g., AMB or BHH, or an analog or derivative thereof), obtaining a disclosed composition, obtaining a disclosed formulation comprising a disclosed composition, obtaining one or more active agents, one or more biologically active agents, pharmaceutically active agents, immune-based therapeutic agents, clinically approved agents, or obtaining a combination thereof. In an aspect a disclosed method or a disclosed method of inhibiting or ameliorating one or more SARS-CoV-2 infection induced cytopathic effects can comprise preparing a disclosed compound (e.g., AMB or BHH, or an analog or derivative thereof) or preparing a disclosed composition comprising AMB or BHH, or analogs or derivatives thereof, or a combination thereof. In an aspect, a disclosed method or a disclosed method of inhibiting or ameliorating one or more SARS-CoV-2 infection induced cytopathic effects can comprise (1) preparing a disclosed composition comprising AMB or BHH, or analogs or derivatives thereof, or a combination thereof, and (2) preparing (i) one or more active agents, (ii) one or more biologically active agents, (iii) one or more pharmaceutically active agents, (iv) one or more immune-based therapeutic agents, (v) one or more clinically approved agents, or (vi) a combination thereof. In an aspect, a disclosed method or a disclosed method of inhibiting or ameliorating one or more SARS-CoV-2 infection induced cytopathic effects can comprise preparing one or more active agents, one or more biologically active agents, one or more pharmaceutically active agents, one or more immune-based therapeutic agents, one or more clinically approved agents, or a combination thereof. In an aspect, a disclosed method or a disclosed method of inhibiting or ameliorating one or more SARS-CoV-2 infection induced cytopathic effects can comprise preparing a disclosed composition comprising (i) AMB or BHH, or analogs or derivatives thereof, or a combination thereof, and (ii) one or more active agents, biologically active agents, pharmaceutically active agents, immune-based therapeutic agents, clinically approved agents, or a combination thereof.

ii. Method of Inhibiting or Reducing the Exopeptidase Activity of ACE2

Disclosed herein is a method comprising inhibiting or reducing the exopeptidase activity of angiotensin converting enzyme 2 (ACE2) by administering a composition comprising an effective amount of AMB or BHH, or analogs or derivatives thereof, or a combination thereof. Disclosed herein is a method of inhibiting or reducing exopeptidase activity of an enzyme comprising administering a composition comprising an effective amount of AMB or BHH, or analogs or derivatives thereof, or a combination thereof; and inhibiting or reducing the exopeptidase activity of angiotensin converting enzyme 2 (ACE2). Disclosed herein is a method of inhibiting or reducing exopeptidase activity of an enzyme comprising inhibiting or reducing the exopeptidase activity of angiotensin converting enzyme 2 (ACE2) by administering a composition comprising an effective amount of AMB or BHH, or analogs or derivatives thereof, or a combination thereof.

In an aspect, the receptor binding domain (RBD) of the Spike glycoprotein can bind to the metallopeptidase domain (MPD) of ACE2.

In an aspect, a disclosed method or a disclosed method of inhibiting or reducing exopeptidase activity of an enzyme or a disclosed method of inhibiting or reducing the exopeptidase activity of angiotensin converting enzyme 2 (ACE2) can comprise administering one or more active agents, one or more biologically active agents, one or more pharmaceutically active agents, one or more immune-based therapeutic agents, one or more clinically approved agents, or a combination thereof. Biologically active agents are described herein and are known to the art. Pharmaceutically active agents are described herein and are known to the art. Immune-based therapeutic agents are described herein and are known to the art. Clinically approved active agents can comprise one or more FDA-approved active agents regardless of whether an active agent is a biologically active agent, a pharmaceutically active agent, or an immune-based therapeutic agent.

In an aspect, a disclosed method or a disclosed method of inhibiting or reducing exopeptidase activity of an enzyme or a disclosed method of inhibiting or reducing the exopeptidase activity of angiotensin converting enzyme 2 (ACE2) can comprise (i) one or more active agents, (ii) one or more biologically active agents, (iii) one or more pharmaceutically active agents, (iv) one or more immune-based therapeutic agents, (v) one or more clinically approved agents, or (vi) a combination thereof. In an aspect, a disclosed method or a disclosed method of inhibiting or reducing exopeptidase activity of an enzyme or a disclosed method of inhibiting or reducing the exopeptidase activity of angiotensin converting enzyme 2 (ACE2) can comprise administering (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof. In an aspect, a disclosed method or a disclosed method of inhibiting or reducing exopeptidase activity of an enzyme or a disclosed method of inhibiting or reducing the exopeptidase activity of angiotensin converting enzyme 2 (ACE2) can comprise (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof.

In an aspect, a composition in a disclosed method or a disclosed method of inhibiting or reducing exopeptidase activity of an enzyme or a disclosed method of inhibiting or reducing the exopeptidase activity of angiotensin converting enzyme 2 (ACE2) can comprise AMB and/or BHH, or analogs or derivatives thereof, or a combination thereof. The composition may be administered in various formats, such as tablet, capsule, syrup, dry powder sachets, inhalation solution/nebulization, drops, ampules, suppository, creams or ointments. For example, the composition may be administered in a tablet format. Tablets may be formulated for controlled release formulation, delayed release formulation, extended release formulation, sustained release formulation, pulsatile release formulation, or mixed immediate release formulation. Tablets may be effervescent. The composition may be administered in a capsule format. Capsules may be formulated for immediate release or sustained release, as examples. Capsules may be hard capsules or and soft capsules. Solution formats may be oil based, aqueous, or emulsions.

In various embodiments, the composition comprising AMB and/or BHH, or analogs or derivatives thereof, or a combination thereof, may be administered via any suitable administration route. Example administration routes include parenteral administration, which may include intramuscular, intraarterial, or intravenous, as examples. Example administration routes include nonparenteral administration, such as oral, rectal, vaginal, nasal, mucosal, percutaneous, transdermal, or ophthalmic, as examples.

The composition comprising AMB and/or BHH, or analogs or derivatives thereof, or a combination thereof, may be administered in a suitable dosage format, via a suitable route of administration, such as any of those identified above, and in an effective daily dose to inhibit or ameliorate a SARS-CoV-2 infection, such as by any mechanism identified herein. The daily dose may be between 30 mg up to 2,000 mg. Example daily dosages may include greater than 200 mg, greater than 400 mg, greater than 500 mg, greater than 600 mg, greater than 700 mg, greater than 800 mg, greater than 900 mg, greater than 1000 mg, between 50 mg and 100 mg, between 100 mg and 200 mg, between 150 mg and 300 mg, between 200 mg and 1000 mg, between 500 mg and 1500 mg, between 450 mg and 1200 mg, between 500 mg and 2000 mg, between 1000 mg and 2000 mg, or any range between 30 mg and 2000 mg. The composition will typically be administered once daily, twice daily, or three times daily; however, additional administrations may be used.

In one example, AMB and/or BHH is administered at a total daily dose of 240 mg, 480 mg or 960 mg, twice daily. The administration route may be oral. In one example, AMB and/or BHH is administered orally in a tablet or capsule.

In an aspect, a disclosed method or a disclosed method of inhibiting or reducing exopeptidase activity of an enzyme or a disclosed method of inhibiting or reducing the exopeptidase activity of angiotensin converting enzyme 2 (ACE2)) can comprise repeating one or more steps.

In an aspect, a disclosed method or a disclosed method of inhibiting or reducing exopeptidase activity of an enzyme or a disclosed method of inhibiting or reducing the exopeptidase activity of angiotensin converting enzyme 2 (ACE2) can comprise identifying a subject having been diagnosed with or suspected of having a SARS-CoV-2 infection. As known to the art, a SARS-CoV-2 infection can be diagnosed and/or confirmed through various tests (such as, e.g., a PCR test or an antigen test).

In an aspect, a disclosed method or a disclosed method of inhibiting or reducing exopeptidase activity of an enzyme or a disclosed method of inhibiting or reducing the exopeptidase activity of angiotensin converting enzyme 2 (ACE2) can comprise identifying a subject having been diagnosed with or suspected of having a SARS-CoV-2 re-infection. As known to the art, a past SARS-CoV-2 infection can be diagnosed and/or confirmed through an antibody test. In an aspect, an antibody test (also known as serology testing) can check for immunoglobulin G (IgG) antibody. In an aspect, a variety of factors can impact the results from an antibody test in a disclosed method (e.g., the time the test was taken after experiencing symptoms, the absence of or time since exposure to the virus, or the lack of an adequate immune response, which can be due to conditions or treatments that suppress immune function).

In an aspect, the administering step of a disclosed method or a disclosed method of inhibiting or reducing exopeptidase activity of an enzyme or a disclosed method of inhibiting or reducing the exopeptidase activity of angiotensin converting enzyme 2 (ACE2) can comprise administering to a subject. In an aspect, a subject can be a human. In an aspect, a human subject can be a participant in a clinical trial. In an aspect, a subject can be a human or a non-human primate diagnosed with or suspected of having a SARS-CoV-2 infection.

In an aspect, a disclosed method or a disclosed method of inhibiting or reducing exopeptidase activity of an enzyme or a disclosed method of inhibiting or reducing the exopeptidase activity of angiotensin converting enzyme 2 (ACE2) can comprise identifying and/or characterizing one or more comorbidities in a subject. In an aspect of a disclosed method, a subject can have one or more comorbidities. Comorbidities are known to the art and can comprise cancer, chronic kidney disease, COPD (chronic obstructive pulmonary disease), an immunocompromised state (weakened immune system) from a solid organ transplant or from a blood or bone marrow transplant, obesity (body mass index [BMI] of 30 or higher), heart conditions (such as, e.g., heart failure, coronary artery disease, or cardiomyopathies), sickle cell disease, type 1 diabetes mellitus or type 2 diabetes mellitus, asthma, cerebrovascular disease, cystic fibrosis, hypertension or high blood pressure, immune deficiencies, HIV, use of corticosteroids, or use of other immune weakening medicines, neurologic conditions, liver disease, pregnancy, pulmonary fibrosis (having damaged or scarred lung tissues), a history of smoking, and thalassemia (a type of blood disorder).

In an aspect, a disclosed method or a disclosed method of inhibiting or reducing exopeptidase activity of an enzyme or a disclosed method of inhibiting or reducing the exopeptidase activity of angiotensin converting enzyme 2 (ACE2) can comprise treating or ameliorating one or more comorbidities in a subject. For example, in an aspect, a disclosed method or a disclosed method of inhibiting or reducing exopeptidase activity of an enzyme or a disclosed method of inhibiting or reducing the exopeptidase activity of angiotensin converting enzyme 2 (ACE2) can comprise (i) administering one or more active agents to treat or ameliorate one or more comorbidities, (ii) administering one or more active agents to treat or ameliorate the same comorbidity, (iii) administering one or more active agents to treat or ameliorate different comorbidities (e.g., an active agent for type 2 diabetes and a different active agent for hypertension), or (iv) a combination thereof. In an aspect, administering an active agent to treat or ameliorate one or more comorbidities can occur prior to, concurrently with, or after the administering of a disclosed composition. In an aspect, a disclosed method or a disclosed method of inhibiting or reducing exopeptidase activity of an enzyme or a disclosed method of inhibiting or reducing the exopeptidase activity of angiotensin converting enzyme 2 (ACE2) can comprise repeating the administering step of an active agent to treat or ameliorate one or more comorbidities.

In an aspect, a disclosed method or a disclosed method of inhibiting or reducing exopeptidase activity of an enzyme or a disclosed method of inhibiting or reducing the exopeptidase activity of angiotensin converting enzyme 2 (ACE2) can comprise modifying or altering one or more steps of a disclosed method. For example, in an aspect, a disclosed method or a disclosed method of inhibiting or reducing exopeptidase activity of an enzyme or a disclosed method of inhibiting or reducing the exopeptidase activity of angiotensin converting enzyme 2 (ACE2) can comprise modifying or altering an administering step. In an aspect, an administering step can be modified or altered, for example, by changing the route of administration, or changing the dose of a disclosed composition, or changing the timing of administration, or changing the frequency of the administration, or a combination thereof.

In an aspect, altering or modifying one or more steps of a disclosed method or a disclosed method of inhibiting or reducing exopeptidase activity of an enzyme or a disclosed method of inhibiting or reducing the exopeptidase activity of angiotensin converting enzyme 2 (ACE2) can be based on the identification and/or characterization of one or more comorbidities in a subject. In an aspect, a disclosed method or a disclosed method of inhibiting or reducing exopeptidase activity of an enzyme or a disclosed method of inhibiting or reducing the exopeptidase activity of angiotensin converting enzyme 2 (ACE2) can comprise modifying or altering the administering step of an active agent to treat or ameliorate one or more comorbidities.

In an aspect, a disclosed method or a disclosed method of inhibiting or reducing exopeptidase activity of an enzyme or a disclosed method of inhibiting or reducing the exopeptidase activity of angiotensin converting enzyme 2 (ACE2) can comprise determining, measuring, and/or ascertaining the presence and/or severity of an infection, such as, for example, a SARS-CoV-2 infection, a bacterial infection, a viral infection, a fungal infection, or a combination thereof. Methods and techniques used to determine, measure, and/or ascertain the presence and/or severity of an infection such as a SARS-CoV-2 infection are typically known to the medical arts.

In an aspect, a disclosed method or a disclosed method of inhibiting or reducing exopeptidase activity of an enzyme or a disclosed method of inhibiting or reducing the exopeptidase activity of angiotensin converting enzyme 2 (ACE2) can comprise monitoring a subject's response to the administration of a disclosed composition comprising CLQ, CLBQ14, or CLCQ, or analogs or derivatives thereof, or a combination thereof. In an aspect of a disclosed method or a disclosed method of inhibiting or reducing exopeptidase activity of an enzyme or a disclosed method of inhibiting or reducing the exopeptidase activity of angiotensin converting enzyme 2 (ACE2), a monitoring step can be repeated one or more times.

In an aspect, a disclosed method or a disclosed method of inhibiting or reducing exopeptidase activity of an enzyme or a disclosed method of inhibiting or reducing the exopeptidase activity of angiotensin converting enzyme 2 (ACE2)

can comprise monitoring a subject's response to the administration of a disclosed composition comprising (i) CLQ, CLBQ14, or CLCQ, or analogs or derivatives thereof, or a combination thereof and (ii) one or more disclosed active agents, one or more biologically active agents, one or more pharmaceutically active agents, one or more immune-based therapeutic agents, one or more clinically approved agents, or a combination thereof. In an aspect of a disclosed method, a monitoring step can be repeated one or more times.

Methods and techniques to monitor a subject's response to a disclosed method can comprise qualitative (or subjective) means as well as quantitative (or objective) means. In an aspect, qualitative means (or subjective means) can comprise a subject's own perspective. For example, a subject can report how he/she is feeling, whether he/she has experienced improvements and/or setbacks, whether he/she has experienced an amelioration of one or more symptoms, or a combination thereof. In an aspect, quantitative means (or objective means) can comprise methods and techniques that include, but are not limited to, the following: (i) fluid analysis (e.g., tests of a subject's fluids including but not limited to aqueous humor and vitreous humor, bile, blood, blood serum, breast milk, cerebrospinal fluid, cerumen (earwax), digestive fluids, endolymph and perilymph, female ejaculate, gastric juice, mucus (including nasal drainage and phlegm), peritoneal fluid, pleural fluid, saliva, sebum (skin oil), semen, sweat, synovial fluid, tears, vaginal secretion, vomit, and urine), (ii) imaging (e.g., ordinary x-rays, ultrasonography, radioisotope (nuclear) scanning, computed tomography (CT), magnetic resonance imaging (MRI), positron emission tomography (PET), and angiography), (iii) endoscopy (e.g., laryngoscopy, bronchoscopy, esophagoscopy, gastroscopy, GI endoscopy, coloscopy, cystoscopy, hysteroscopy, arthroscopy, laparoscopy, mediastinoscopy, and thoracoscopy), (iv) analysis of organ activity (e.g., electrocardiography (ECG), electroencephalography (EEG), and pulse oximetry), (v) biopsy (e.g., removal of tissue samples for microscopic evaluation), and (vi) genetic testing.

In an aspect, a disclosed method or a disclosed method of inhibiting or reducing exopeptidase activity of an enzyme or a disclosed method of inhibiting or reducing the exopeptidase activity of angiotensin converting enzyme 2 (ACE2) can comprise obtaining a disclosed compound (e.g., CLQ, CLBQ14, or CLCQ, or an analog or derivative thereof), obtaining a disclosed composition, obtaining a disclosed formulation comprising a disclosed composition, obtaining one or more active agents, one or more biologically active agents, pharmaceutically active agents, immune-based therapeutic agents, clinically approved agents, or obtaining a combination thereof.

In an aspect, a disclosed method or a disclosed method of inhibiting or reducing exopeptidase activity of an enzyme or a disclosed method of inhibiting or reducing the exopeptidase activity of angiotensin converting enzyme 2 (ACE2) can comprise preparing a disclosed compound (e.g., CLQ, CLBQ14, or CLCQ, or an analog or derivative thereof) or preparing a disclosed composition comprising CLQ, CLBQ14, or CLCQ, or analogs or derivatives thereof, or a combination thereof. In an aspect, a disclosed method or a disclosed method of inhibiting or reducing exopeptidase activity of an enzyme or a disclosed method of inhibiting or reducing the exopeptidase activity of angiotensin converting enzyme 2 (ACE2) can comprise (1) preparing a disclosed composition comprising CLQ, CLBQ14, or CLCQ, or analogs or derivatives thereof, or a combination thereof, and (2) preparing (i) one or more active agents, (ii) one or more biologically active agents, (iii) one or more pharmaceutically active agents, (iv) one or more immune-based therapeutic agents, (v) one or more clinically approved agents, or (vi) a combination thereof. In an aspect, a disclosed method or a disclosed method of inhibiting or reducing exopeptidase activity of an enzyme or a disclosed method of inhibiting or reducing the exopeptidase activity of angiotensin converting enzyme 2 (ACE2) can comprise preparing one or more active agents, one or more biologically active agents, one or more pharmaceutically active agents, one or more immune-based therapeutic agents, one or more clinically approved agents, or a combination thereof. In an aspect, a disclosed method or a disclosed method of inhibiting or reducing exopeptidase activity of an enzyme or a disclosed method of inhibiting or reducing the exopeptidase activity of angiotensin converting enzyme 2 (ACE2) can comprise preparing a disclosed composition comprising (i) CLQ, CLBQ14, or CLCQ, or analogs or derivatives thereof, or a combination thereof, and (ii) one or more active agents, biologically active agents, pharmaceutically active agents, immune-based therapeutic agents, clinically approved agents, or a combination thereof.

iii. Method of Inhibiting or Disrupting the Interaction Between ACE2 and Spike Protein Disclosed herein is a method comprising administering a composition comprising an effective amount of AMB or BHH, or analogs or derivatives thereof, or a combination thereof, and inhibiting or disrupting the physical interaction of angiotensin converting enzyme 2 (ACE2) with the Spike (S) glycoprotein of SARS-CoV-2. Disclosed herein is a method comprising inhibiting or disrupting the physical interaction of angiotensin converting enzyme 2 (ACE2) with the Spike (S) glycoprotein of SARS-CoV-2 by administering a composition comprising an effective amount of AMB or BHH, or analogs or derivatives thereof, or a combination thereof. Disclosed herein is a method of inhibiting or disrupting the physical interaction of an angiotensin converting enzyme 2 (ACE2) with the Spike (S) glycoprotein of SARS-CoV-2 comprising administering a composition comprising an effective amount of AMB or BHH, or analogs or derivatives thereof, or a combination thereof, thereby inhibiting or disrupting the physical interaction of angiotensin converting enzyme 2 (ACE2) with the Spike (S) glycoprotein of SARS-CoV-2. Disclosed herein is a method of inhibiting or reducing viral infectivity in a subject comprising administering to a subject a composition comprising an effective amount of AMVB or BHH, or analogs or derivatives thereof, or a combination thereof; and inhibiting or disrupting the physical interaction of angiotensin converting enzyme 2 (ACE2) with the Spike (S) glycoprotein of SARS-CoV-2, thereby inhibiting or reducing viral infectivity. Disclosed herein is a method of inhibiting or reducing viral infectivity in a subject comprising inhibiting or disrupting the physical interaction of angiotensin converting enzyme 2 (ACE2) with the Spike (S) glycoprotein of SARS-CoV-2 by administering to a subject a composition comprising an effective amount of AMB or BHH, or analogs or derivatives thereof, or a combination thereof, thereby inhibiting or reducing viral infectivity. Disclosed herein is a method of inhibiting or ameliorating a SARS-CoV-2 infection in a subject comprising administering to a subject a composition comprising an effective amount of AMB or BHH, or analogs or derivatives thereof, or a combination thereof, and inhibiting or disrupting the physical interaction of angiotensin converting enzyme 2 (ACE2) with the Spike (S) glycoprotein of SARS-CoV-2, thereby inhibiting or ameliorating a SARS-CoV-2 infection. Disclosed herein is a method of inhibiting or ameliorating a SARS-CoV-2 infection in a subject comprising inhibiting or disrupting the physical interaction of angiotensin converting enzyme 2 (ACE2) with the Spike (S) glycoprotein of SARS-CoV-2 by administering to a subject a composition comprising an effective amount of AMB or BHH, or analogs or derivatives thereof, or a combination thereof, thereby inhibiting or ameliorating a SARS-CoV-2 infection. Disclosed herein is a method of inhibiting or reducing viral entry into cells of a subject comprising administering to a subject a composition comprising an effective amount of AMB or BHH, or analogs or derivatives thereof, or a combination thereof, and inhibiting or disrupting the physical interaction of angiotensin converting enzyme 2 (ACE2) with the Spike (S) glycoprotein of SARS-CoV-2, thereby inhibiting or reducing viral entry into cells of the subject. Disclosed herein is a method of inhibiting or reducing viral entry into cells of a subject comprising inhibiting or disrupting the physical interaction of angiotensin converting enzyme 2 (ACE2) with the Spike (S) glycoprotein of SARS-CoV-2 by administering to a subject a composition comprising an effective amount of AMB or BHH, or analogs or derivatives thereof, or a combination thereof, thereby inhibiting or reducing viral entry into cells of the subject. Disclosed herein is a method comprising administering a composition comprising an effective amount AMB or BHH, or analogs or derivatives thereof, or a combination thereof; inhibiting or reducing the activity of a type II transmembrane serine protease; and inhibiting or disrupting the physical interaction of angiotensin converting enzyme 2 (ACE2) with the Spike (S) glycoprotein of SARS-CoV-2. Disclosed herein is a method comprising inhibiting or reducing the activity of a type II transmembrane serine protease and inhibiting or disrupting the physical interaction of an angiotensin converting enzyme 2 (ACE2) with the Spike (S) glycoprotein of SARS-CoV-2 by administering a composition comprising an effective amount of AMB or BHH, or analogs or derivatives thereof, or a combination thereof. Disclosed herein is a method of inhibiting or disrupting the physical interaction of angiotensin converting enzyme 2 (ACE2) with the Spike (S) glycoprotein of SARS-CoV-2 comprising administering a composition comprising an effective amount of AMB or BHH, or analogs or derivatives thereof, or a combination thereof, and inhibiting or reducing the activity of a type II transmembrane serine protease, thereby inhibiting or disrupting the physical interaction of an angiotensin converting enzyme 2 (ACE). Disclosed herein is a method of inhibiting or reducing viral infectivity in a subject comprising administering to a subject a composition comprising an effective amount of AMB or BHH, or analogs or derivatives thereof, or a combination thereof, or a combination thereof; inhibiting or reducing the activity of a type II transmembrane serine protease; and inhibiting or disrupting the physical interaction of angiotensin converting enzyme 2 (ACE2) with the Spike (S) glycoprotein of SARS-CoV-2, thereby inhibiting or reducing viral infectivity. Disclosed herein is a method of inhibiting or reducing viral infectivity in a subject comprising inhibiting or reducing the activity of a type II transmembrane serine protease by administering to a subject a composition comprising an effective amount of AMB or BHH, or analogs or derivatives thereof, or a combination thereof, and inhibiting or disrupting the physical interaction of angiotensin converting enzyme 2 (ACE2) with the Spike (S) glycoprotein of SARS-CoV-2, thereby inhibiting or reducing viral infectivity. Disclosed herein is a method of inhibiting or reducing a SARS-CoV-2 infection in a subject comprising administering to a subject a composition comprising an effective amount of AMB or BHH, or analogs or derivatives thereof, or a combination thereof; inhibiting or reducing the activity of a type II transmembrane serine protease; and inhibiting or disrupting the physical interaction of angiotensin converting enzyme 2 (ACE2) with the Spike (S) glycoprotein of SARS-CoV-2, thereby inhibiting or reducing a SARS-CoV-2 infection. Disclosed herein is a method of inhibiting or reducing a SARS-CoV-2 infection in a subject comprising inhibiting or reducing the activity of a type II transmembrane serine protease and inhibiting or disrupting the physical interaction of angiotensin converting enzyme 2 (ACE2) with the Spike (S) glycoprotein of SARS-CoV-2 by administering to a subject a composition comprising an effective amount of AMB or BHH, or analogs or derivatives thereof, or a combination thereof, thereby inhibiting or reducing a SARS-CoV-2 infection. Disclosed herein is a method of inhibiting or reducing viral entry into cells of a subject comprising administering to a subject a composition comprising an effective amount of AMB or BHH, or analogs or derivatives thereof, or a combination thereof; inhibiting or reducing the activity of a type II transmembrane serine protease; and inhibiting or disrupting the physical interaction of angiotensin converting enzyme 2 (ACE2) with the Spike (S) glycoprotein of SARS-CoV-2, thereby inhibiting or reducing viral entry into cells of the subject. Disclosed herein is a method of inhibiting or reducing viral entry into cells of a subject comprising disrupting the physical interaction of angiotensin converting enzyme 2 (ACE2) with the Spike (S) glycoprotein of SARS-CoV-2 by administering to a subject a composition comprising an effective amount of AMB or BHH, or analogs or derivatives thereof, or a combination thereof, and inhibiting or reducing the activity of a type II transmembrane serine protease, thereby inhibiting or reducing viral entry into cells of the subject.

In an aspect, the receptor binding domain (RBD) of the Spike glycoprotein can bind to the metallopeptidase domain (MPD) of the ACE2 receptor. In an aspect, the type II transmembrane serine protease is TMPRSS2.

In an aspect, a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise administering one or more active agents, one or more biologically active agents, one or more pharmaceutically active agents, one or more immune-based therapeutic agents, one or more clinically approved agents, or a combination thereof. Biologically active agents are described herein and are known to the art. Pharmaceutically active agents are described herein and are known to the art. Immune-based therapeutic agents are described herein and are known to the art. Clinically approved active agents can comprise one or more FDA-approved active agents regardless of whether an active agent is a biologically active agent, a pharmaceutically active agent, or an immune-based therapeutic agent.

In an aspect, a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise (i) one or more active agents, (ii) one or more biologically active agents, (iii) one or more pharmaceutically active agents, (iv) one or more immune-based therapeutic agents, (v) one or more clinically approved agents, or (vi) a combination thereof.

In an aspect, a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise administering (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof. In an aspect, a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof.

In an aspect, a composition in a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise a AMB and/or BHH, or analogs or derivatives thereof, or a combination thereof. The composition may be administered in various formats, such as tablet, capsule, syrup, dry powder sachets, inhalation solution/nebulization, drops, ampules, suppository, creams or ointments. For example, the composition may be administered in a tablet format. Tablets may be formulated for controlled release formulation, delayed release formulation, extended release formulation, sustained release formulation, pulsatile release formulation, or mixed immediate release formulation. Tablets may be effervescent. The composition may be administered in a capsule format. Capsules may be formulated for immediate release or sustained release, as examples. Capsules may be hard capsules or and soft capsules. Solution formats may be oil based, aqueous, or emulsions.

In various embodiments, the composition comprising AMB and/or BHH, or analogs or derivatives thereof, or a combination thereof, may be administered via any suitable administration route. Example administration routes include parenteral administration, which may include intramuscular, intraarterial, or intravenous, as examples. Example administration routes include nonparenteral administration, such as oral, rectal, vaginal, nasal, mucosal, percutaneous, transdermal, or ophthalmic, as examples.

The composition comprising AMB and/or BHH, or analogs or derivatives thereof, or a combination thereof, may be administered in a suitable dosage format, via a suitable route of administration, such as any of those identified above, and in an effective daily dose to inhibit or ameliorate a SARS-CoV-2 infection, such as by any mechanism identified herein. The daily dose may be between 30 mg up to 2,000 mg. Example daily dosages may include greater than 200 mg, greater than 400 mg, greater than 500 mg, greater than 600 mg, greater than 700 mg, greater than 800 mg, greater than 900 mg, greater than 1000 mg, between 50 mg and 100 mg, between 100 mg and 200 mg, between 150 mg and 300 mg, between 200 mg and 1000 mg, between 500 mg and 1500 mg, between 450 mg and 1200 mg, between 500 mg and 2000 mg, between 1000 mg and 2000 mg, or any range between 30 mg and 2000 mg. The composition will typically be administered once daily, twice daily, or three times daily; however, additional administrations may be used.

In one example, AMB and/or BHH is administered at a total daily dose of 240 mg, 480 mg or 960 mg, twice daily. The administration route may be oral. In one example, AMB and/or BHH is administered orally in a tablet or capsule.

In an aspect, a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise repeating one or more steps.

In an aspect, a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise identifying a subject having been diagnosed with or suspected of having a SARS-CoV-2 infection. As known to the art, a SARS-CoV-2 infection can be diagnosed and/or confirmed through various tests (such as, e.g., a PCR test or an antigen test).

In an aspect, a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise identifying a subject having been diagnosed with or suspected of having a SARS-CoV-2 re-infection. As known to the art, a past SARS-CoV-2 infection can be diagnosed and/or confirmed through an antibody test. In an aspect, an antibody test (also known as serology testing) can check for Immunoglobulin G (IgG) antibody. In an aspect, a variety of factors can impact the results from an antibody test in a disclosed method (e.g., the time the test was taken after experiencing symptoms, the absence of or time since exposure to the virus, or the lack of an adequate immune response, which can be due to conditions or treatments that suppress immune function).

In an aspect, the administering step of a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise administering to a subject. In an aspect, a subject can be a human. In an aspect, a human subject can be a participant in a clinical trial. In an aspect, a subject can be human or a non-human primate diagnosed with or suspected of having a SARS-CoV-2 infection.

In an aspect, a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise identifying and/or characterizing one or more comorbidities in a subject. In an aspect of a disclosed method, a subject can have one or more comorbidities. Comorbidities are known to the art and can comprise cancer, chronic kidney disease, COPD (chronic obstructive pulmonary disease), an immunocompromised state (weakened immune system) from a solid organ transplant or from a blood or bone marrow transplant, obesity (body mass index [BMI] of 30 or higher), heart conditions (such as, e.g., heart failure, coronary artery disease, or cardiomyopathies), sickle cell disease, type 1 diabetes mellitus or type 2 diabetes mellitus, asthma, cerebrovascular disease, cystic fibrosis, hypertension or high blood pressure, immune deficiencies, HIV, use of corticosteroids, or use of other immune weakening medicines, neurologic conditions, liver disease, pregnancy, pulmonary fibrosis (having damaged or scarred lung tissues), a history of smoking, and thalassemia (a type of blood disorder).

In an aspect, a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise (i) administering one or more active agents to treat or ameliorate one or more comorbidities, (ii) administering one or more active agents to treat or ameliorate the same comorbidity, (iii) administering one or more active agents to treat or ameliorate different comorbidities (e.g., an active agent for type 2 diabetes and a different active agent for hypertension), or (iv) a combination thereof. In an aspect, administering an active agent to treat or ameliorate one or more comorbidities can occur prior to, concurrently with, or after the administering of a disclosed composition. In an aspect, a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise repeating the administering step of an active agent to treat or ameliorate one or more comorbidities.

In an aspect, a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise modifying or altering an administering step. In an aspect, an administering step can be modified or altered, for example, by changing the route of administration, or changing the dose of a disclosed composition, or changing the timing of administration, or changing the frequency of the administration, or a combination thereof.

In an aspect, altering or modifying one or more steps of a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can be based on the identification and/or characterization of one or more comorbidities in a subject.

In an aspect a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise modifying or altering the administering step of an active agent to treat or ameliorate one or more comorbidities.

In an aspect, a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise determining, measuring, and/or ascertaining the presence and/or severity of an infection, such as, for example, a SARS-CoV-2 infection, a bacterial infection, a viral infection, a fungal infection, or a combination thereof. Methods and techniques used to determine, measure, and/or ascertain the presence and/or severity of an infection such as a SARS-CoV-2 infection are typically known to the medical arts.

In an aspect, a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise monitoring a subject's response to the administration of a disclosed composition comprising AMB or BHH, or analogs or derivatives thereof, or a combination thereof. In an aspect of a disclosed method, a monitoring step can be repeated one or more times.

In an aspect, a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise monitoring a subject's response to the administration of a disclosed composition comprising (i) AMB or BHH, or analogs or derivatives thereof, or a combination thereof and (ii) one or more disclosed active agents, one or more biologically active agents, one or more pharmaceutically active agents, one or more immune-based therapeutic agents, one or more clinically approved agents, or a combination thereof. In an aspect of a disclosed method, a monitoring step can be repeated one or more times.

Methods and techniques to monitor a subject's response to a disclosed method can comprise qualitative (or subjective) means as well as quantitative (or objective) means. In an aspect, qualitative means (or subjective means) can comprise a subject's own perspective. For example, a subject can report how he/she is feeling, whether he/she has experienced improvements and/or setbacks, whether he/she has experienced an amelioration or an intensification of one or more symptoms, or a combination thereof. In an aspect, quantitative means (or objective means) can comprise methods and techniques that include, but are not limited to, the following: (i) fluid analysis (e.g., tests of a subject's fluids including but not limited to aqueous humor and vitreous humor, bile, blood, blood serum, breast milk, cerebrospinal fluid, cerumen (earwax), digestive fluids, endolymph and perilymph, female ejaculate, gastric juice, mucus (including nasal drainage and phlegm), peritoneal fluid, pleural fluid, saliva, sebum (skin oil), semen, sweat, synovial fluid, tears, vaginal secretion, vomit, and urine), (ii) imaging (e.g., ordinary x-rays, ultrasonography, radioisotope (nuclear) scanning, computed tomography (CT), magnetic resonance imaging (MRI), positron emission tomography (PET), and angiography), (iii) endoscopy (e.g., laryngoscopy, bronchoscopy, esophagoscopy, gastroscopy, GI endoscopy, colosopy, cystoscopy, hysteroscopy, arthroscopy, laparoscopy, mediastinoscopy, and thoracoscopy), (iv) analysis of organ activity (e.g., electrocardiography (ECG), electroencephalography (EEG), and pulse oximetry), (v) biopsy (e.g., removal of tissue samples for microscopic evaluation), and (vi) genetic testing.

In an aspect, a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise obtaining a disclosed compound (e.g., AMB or BHH, or an analog or derivative thereof), obtaining a disclosed composition, obtaining a disclosed formulation comprising a disclosed composition, obtaining one or more active agents, one or more biologically active agents, pharmaceutically active agents, immune-based therapeutic agents, clinically approved agents, or obtaining a combination thereof.

In an aspect, a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise preparing a disclosed compound (e.g., AMB or BHH, or an analog or derivative thereof) or preparing a disclosed composition comprising AMB or BHH, or analogs or derivatives thereof, or a combination thereof.

In an aspect a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise (1) preparing a disclosed composition comprising AMB or BHH, or analogs or derivatives thereof, or a combination thereof, and (2) preparing (i) one or more active agents, (ii) one or more biologically active agents, (iii) one or more pharmaceutically active agents, (iv) one or more immune-based therapeutic agents, (v) one or more clinically approved agents, or (vi) a combination thereof.

In an aspect, a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise preparing one or more active agents, one or more biologically active agents, one or more pharmaceutically active agents, one or more immune-based therapeutic agents, one or more clinically approved agents, or a combination thereof.

In an aspect, a disclosed method or a disclosed method of inhibiting or disrupting the physical interaction of angiotensin converting enzyme 2 (ACE2) with the Spike (S) glycoprotein of SARS-CoV-2 or a disclosed method of inhibiting or reducing viral infectivity in a subject or a method of inhibiting or ameliorating a SARS-CoV-2 infection or a disclosed method of inhibiting or reducing viral entry into cells of a subject or a disclosed method of inhibiting or reducing the activity of a type II transmembrane serine protease can comprise preparing a disclosed composition comprising (i) AMB or BHH, or analogs or derivatives thereof, or a combination thereof, and (ii) one or more active agents, biologically active agents, pharmaceutically active agents, immune-based therapeutic agents, clinically approved agents, or a combination thereof.

2. Compositions Comprising the Benzylamine Structural Class General Composition

Disclosed herein is composition comprising an effective amount of one or more compounds belonging to the benzylamine structural class; and a pharmaceutically acceptable diluent, carrier, excipient, or stabilizer, or a combination thereof, wherein the composition inhibits or ameliorates a SARS-CoV-2 infection. Disclosed herein is a composition comprising an effective amount of AMB or BHH, or analogs or derivatives thereof, or a combination thereof; and a pharmaceutically acceptable diluent, carrier, excipient, or stabilizer, or a combination thereof, wherein the composition inhibits or ameliorates a SARS-CoV-2 infection. Disclosed herein is composition comprising an effective amount of one or more compounds belonging to the benzylamine structural class; an effective amount of one or more clinically approved active agents; and a pharmaceutically acceptable diluent, carrier, excipient, or stabilizer, or a combination thereof, wherein the composition inhibits or ameliorates a SARS-CoV-2 infection. Disclosed herein is a composition comprising an effective amount of AMB or BHH, or analogs or derivatives thereof, or a combination thereof; an effective amount of one or more clinically approved active agents; and a pharmaceutically acceptable diluent, carrier, excipient, or stabilizer, or a combination thereof, wherein the composition inhibits or ameliorates a SARS-CoV-2 infection.

The benzylamine structural class is known to the art and discussed herein. Pharmaceutically acceptable diluents, carriers, excipients, and stabilizers are known to the art and discussed herein.

In an aspect, a disclosed composition comprising one or more compounds belonging to the benzylamine structural class or a disclosed composition comprising AMB or BHH, or analogs or derivatives thereof, or a combination thereof can inhibit or ameliorate a SARS-CoV-2 infection.

In an aspect, a disclosed composition comprising one or more compounds belonging to the benzylamine structural class or a disclosed composition comprising AMB or BHH, or analogs or derivatives thereof, or a combination thereof can comprise one or more active agents, one or more biologically active agents, one or more pharmaceutically active agents, one or more immune-based therapeutic agents, one or more clinically approved agents, or a combination thereof. Biologically active agents are described herein and are known to the art. Pharmaceutically active agents are described herein and are known to the art. Immune-based therapeutic agents are described herein and are known to the art. Clinically approved active agents can comprise one or more FDA-approved active agents regardless of whether an active agent is a biologically active agent, a pharmaceutically active agent, or an immune-based therapeutic agent.

In an aspect, a disclosed composition comprising one or more compounds belonging to the benzylamine structural class or a disclosed composition comprising AMB or BHH, or analogs or derivatives thereof, or a combination thereof can comprise (i) one or more active agents, (ii) one or more biologically active agents, (iii) one or more pharmaceutically active agents, (iv) one or more immune-based therapeutic agents, (v) one or more clinically approved agents, or (vi) a combination thereof. In an aspect, a disclosed composition comprising one or more compounds belonging to the benzylamine structural class or a disclosed composition comprising AMB or BHH, or analogs or derivatives thereof, or a combination thereof can comprise (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof.

A disclosed composition comprising AMB and/or BHH, or analogs or derivatives thereof, or a combination thereof, may be administered in various formats, such as tablet, capsule, syrup, dry powder sachets, inhalation solution/nebulization, drops, ampules, suppository, creams or ointments. For example, the composition may be administered in a tablet format. Tablets may be formulated for controlled release formulation, delayed release formulation, extended release formulation, sustained release formulation, pulsatile release formulation, or mixed immediate release formulation. Tablets may be effervescent. The composition may be administered in a capsule format. Capsules may be formulated for immediate release or sustained release, as examples. Capsules may be hard capsules or and soft capsules. Solution formats may be oil based, aqueous, or emulsions.

The composition comprising AMB and/or BHH, or analogs or derivatives thereof, or a combination thereof, may be administered via any suitable administration route. Example administration routes include parenteral administration, which may include intramuscular, intraarterial, or intravenous, as examples. Example administration routes include nonparenteral administration, such as oral, rectal, vaginal, nasal, mucosal, percutaneous, transdermal, or ophthalmic, as examples.

The composition comprising AMB and/or BHH, or analogs or derivatives thereof, or a combination thereof, may be administered in a suitable dosage format, via a suitable route of administration, such as any of those identified above, and in an effective daily dose to inhibit or ameliorate a SARS-CoV-2 infection, such as by any mechanism identified herein. The daily dose may be between 30 mg up to 2,000 mg. Example daily dosages may include greater than 200 mg, greater than 400 mg, greater than 500 mg, greater than 600 mg, greater than 700 mg, greater than 800 mg, greater than 900 mg, greater than 1000 mg, between 50 mg and 100 mg, between 100 mg and 200 mg, between 150 mg and 300 mg, between 200 mg and 1000 mg, between 500 mg and 1500 mg, between 450 mg and 1200 mg, between 500 mg and 2000 mg, between 1000 mg and 2000 mg, or any range between 30 mg and 2000 mg. The composition will typically be administered once daily, twice daily, or three times daily; however, additional administrations may be used.

In one example, AMB and/or BHH is administered at a total daily dose of 240 mg, 480 mg or 960 mg, twice daily. The administration route may be oral. In one example, AMB and/or BHH is administered orally in a tablet or capsule.

In an aspect, a disclosed composition comprising one or more compounds belonging to the benzylamine structural class or a disclosed composition comprising AMB or BHH, or analogs or derivatives thereof, or a combination thereof can be administered to a subject. In an aspect, a subject can be a human. In an aspect, a human subject can be a participant in a clinical trial. In an aspect, a subject can be a human or a non-human primate diagnosed with or suspected of having a SARS-CoV-2 infection.

In an aspect, a disclosed composition comprising one or more compounds belonging to the benzylamine structural class or a disclosed composition comprising AMB or BHH, or analogs or derivatives thereof, or a combination thereof can be administered to a subject having one or more comorbidities.

In an aspect, a disclosed composition comprising one or more compounds belonging to the benzylamine structural class or a disclosed composition comprising AMB or BHH, or analogs or derivatives thereof, or a combination thereof can comprise one or more active agents to treat or ameliorate one or more comorbidities. Comorbidities are known to the art and are discussed herein.

i. Compositions for Inhibiting or Ameliorating a SARS-CoV-2 Infection

Disclosed herein is a composition comprising an effective amount of AMB or BHH, or analogs or derivatives thereof, or a combination thereof; and a pharmaceutically acceptable diluent, carrier, excipient, or stabilizer, or a combination thereof, wherein the composition inhibits or ameliorates one or more SARS-CoV-2 infection induced cytopathic effects. Disclosed herein is a composition comprising an effective amount of AMB or BHH, or analogs or derivatives thereof, or a combination thereof, an effective amount of one or more anti-viral agents; and a pharmaceutically acceptable diluent, carrier, excipient, or stabilizer, or a combination thereof, wherein the composition inhibits or ameliorates one or more SARS-CoV-2 infection induced cytopathic effects. Disclosed herein is a composition for inhibiting or ameliorating cytopathic effects in a subject comprising an effective amount of AMB or BHH, or analogs or derivatives thereof, or a combination thereof, and a pharmaceutically acceptable diluent, carrier, excipient, or stabilizer, or a combination thereof, wherein the composition inhibits or ameliorates one or more SARS-CoV-2 infection induced cytopathic effects in a subject in need thereof. Disclosed herein is a composition for inhibiting or ameliorating cytopathic effects in a subject comprising an effective amount AMB or BHH, or analogs or derivatives thereof, or a combination thereof; an effective amount of one or more anti-viral agents; and a pharmaceutically acceptable diluent, carrier, excipient, or stabilizer, or a combination thereof, wherein the composition inhibits or ameliorates one or more cytopathic effects in a subject in need thereof. Disclosed herein is a composition for inhibiting or ameliorating one or more SARS-CoV-2 infection induced cytopathic effects in a subject comprising an effective amount of AMB or BHH, or analogs or derivatives thereof, or a combination thereof, and a pharmaceutically acceptable diluent, carrier, excipient, or stabilizer, or a combination thereof, wherein the composition inhibits or ameliorates one or more cytopathic effects in a subject diagnosed with or suspected of having a SARS-CoV-2 infection. Disclosed herein is a composition for inhibiting or ameliorating one or more SARS-CoV-2 infection induced cytopathic effects in a subject comprising an effective amount of AMB or BHH, or analogs or derivatives thereof, or a combination thereof, an effective amount of one or more anti-viral agents; and a pharmaceutically acceptable diluent, carrier, excipient, or stabilizer, or a combination thereof; wherein the composition inhibits or ameliorates one or more cytopathic effects in a subject diagnosed with or suspected of having a SARS-CoV-2 infection.

In an aspect, a disclosed composition comprising one or more compounds belonging to the 8-hydroxyquinoline structural class or a disclosed composition comprising AMB or BHH, or analogs or derivatives thereof, or a combination thereof can inhibit or ameliorate one or more SARS-CoV-2 infection induced cytopathic effects.

In an aspect, a disclosed composition comprising AMB or BHH, or analogs or derivatives thereof, or a combination thereof can comprise one or more active agents, one or more biologically active agents, one or more pharmaceutically active agents, one or more immune-based therapeutic agents, one or more clinically approved agents, or a combination thereof. Biologically active agents are described herein and are known to the art. Pharmaceutically active agents are described herein and are known to the art. Immune-based therapeutic agents are described herein and are known to the art. Clinically approved active agents can comprise one or more FDA-approved active agents regardless of whether an active agent is a biologically active agent, a pharmaceutically active agent, or an immune-based therapeutic agent. In an aspect, a disclosed composition comprising AMB or BHH, or analogs or derivatives thereof, or a combination thereof can comprise (i) one or more active agents, (ii) one or more biologically active agents, (iii) one or more pharmaceutically active agents, (iv) one or more immune-based therapeutic agents, (v) one or more clinically approved agents, or (vi) a combination thereof. In an aspect, a disclosed composition comprising AMB or BHH, or analogs or derivatives thereof, or a combination thereof can comprise (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof.

In an aspect, a disclosed composition can be administered to a subject. In an aspect, a subject can be a human. In an aspect, a human subject can be a participant in a clinical trial. In an aspect, a subject can be a human or a non-human primate diagnosed with or suspected of having a SARS-CoV-2 infection.

A disclosed composition comprising AMB and/or BHH, or analogs or derivatives thereof, or a combination thereof, may be administered in various formats, such as tablet, capsule, syrup, dry powder sachets, inhalation solution/nebulization, drops, ampules, suppository, creams or ointments. For example, the composition may be administered in a tablet format. Tablets may be formulated for controlled release formulation, delayed release formulation, extended release formulation, sustained release formulation, pulsatile release formulation, or mixed immediate release formulation. Tablets may be effervescent. The composition may be administered in a capsule format. Capsules may be formulated for immediate release or sustained release, as examples. Capsules may be hard capsules or and soft capsules. Solution formats may be oil based, aqueous, or emulsions.

The composition comprising AMB and/or BHH, or analogs or derivatives thereof, or a combination thereof, may be administered via any suitable administration route. Example administration routes include parenteral administration, which may include intramuscular, intraarterial, or intravenous, as examples. Example administration routes include nonparenteral administration, such as oral, rectal, vaginal, nasal, mucosal, percutaneous, transdermal, or ophthalmic, as examples.

In various embodiments, the composition comprising AMB and/or BHH, or analogs or derivatives thereof, or a combination thereof, may be administered in a suitable dosage format, via a suitable route of administration, such as any of those identified above, and in an effective daily dose to inhibit or ameliorate a SARS-CoV-2 infection, such as by any mechanism identified herein. The daily dose may be between 30 mg up to 2,000 mg. Example daily dosages may include greater than 200 mg, greater than 400 mg, greater than 500 mg, greater than 600 mg, greater than 700 mg, greater than 800 mg, greater than 900 mg, greater than 1000 mg, between 50 mg and 100 mg, between 100 mg and 200 mg, between 150 mg and 300 mg, between 200 mg and 1000 mg, between 500 mg and 1500 mg, between 450 mg and 1200 mg, between 500 mg and 2000 mg, between 1000 mg and 2000 mg, or any range between 30 mg and 2000 mg. The composition will typically be administered once daily, twice daily, or three times daily; however, additional administrations may be used.

In one example, AMB and/or BHH is administered at a total daily dose of 240 mg, 480 mg or 960 mg, twice daily. The administration route may be oral. In one example, AMB and/or BHH is administered orally in a tablet or capsule.

In an aspect, a disclosed composition comprising AMB or BHH, or analogs or derivatives thereof, or a combination thereof can be administered to a subject. In an aspect, a subject can be a human. In an aspect, a human subject can be a participant in a clinical trial. In an aspect, a subject can be a non-human primate diagnosed with or suspected of having a SARS-CoV-2 infection.

In an aspect, a disclosed composition comprising AMB or BHH, or analogs or derivatives thereof, or a combination thereof can be administered to a subject having one or more comorbidities. In an aspect, a disclosed composition comprising AMB or BHH, or analogs or derivatives thereof, or a combination thereof can comprise one or more active agents to treat or ameliorate one or more comorbidities. Comorbidities are known to the art and are discussed herein.

ii. Compositions for Inhibiting or Reducing the Exopeptidase Activity of ACE2

Disclosed herein is a composition for inhibiting or reducing exopeptidase activity of an enzyme comprising an effective amount of AMB or BHH, or analogs or derivatives thereof, or a combination thereof, and a pharmaceutically acceptable diluent, carrier, excipient, or stabilizer, or a combination thereof, wherein the composition inhibits or reduces the exopeptidase activity of angiotensin converting enzyme 2 (ACE2). Disclosed herein is a composition for inhibiting or reducing exopeptidase activity of an enzyme comprising an effective amount of AMB or BHH, or analogs or derivatives thereof, or a combination thereof; and an effective amount of zinc chloride; wherein the composition inhibits or reduces the exopeptidase activity of angiotensin converting enzyme 2 (ACE2). Disclosed herein is a composition for inhibiting or reducing exopeptidase activity of an enzyme comprising an effective amount of AMB or BHH, or analogs or derivatives thereof, or a combination thereof, wherein the composition inhibits or disrupts the physical interaction of angiotensin converting enzyme 2 (ACE2) with the Spike (S) glycoprotein of SARS-CoV-2, thereby inhibiting or reducing the exopeptidase activity of angiotensin converting enzyme 2 (ACE2). Disclosed herein is a composition for inhibiting or reducing exopeptidase activity of an enzyme comprising an effective amount of AMB or BHH, or analogs or derivatives thereof, or a combination thereof, and an effective amount of zinc chloride, wherein the composition inhibits or disrupts the physical interaction of angiotensin converting enzyme 2 (ACE2) with the Spike (S) glycoprotein of SARS-CoV-2, thereby inhibiting or reducing the exopeptidase activity of angiotensin converting enzyme 2 (ACE2).

In an aspect, a disclosed composition comprising one or more compounds belonging to the 8-hydroxyquinoline structural class or a disclosed composition comprising AMB or BHH, or analogs or derivatives thereof, or a combination thereof can inhibit or reduce the exopeptidase activity of angiotensin converting enzyme 2 (ACE2). In an aspect, a disclosed composition comprising one or more compounds belonging to the 8-hydroxyquinoline structural class or a disclosed composition comprising AMB or BHH, or analogs or derivatives thereof, or a combination thereof can inhibit or disrupt the physical interaction of angiotensin converting enzyme 2 (ACE2) with the Spike (S) glycoprotein of SARS-CoV-2

AMB, BHH, and analogs or derivatives thereof are known to the art and are discussed herein. Pharmaceutically acceptable diluents, carriers, excipients, stabilizers, and combinations thereof are known to the art and are discussed herein.

In an aspect, the receptor binding domain (RBD) of the Spike glycoprotein can bind to the metallopeptidase domain (MPD) of the ACE2 receptor.

In an aspect, a disclosed composition comprising AMB or BHH, or analogs or derivatives thereof, or a combination thereof can comprise one or more active agents, one or more biologically active agents, one or more pharmaceutically active agents, one or more immune-based therapeutic agents, one or more clinically approved agents, or a combination thereof. Biologically active agents are described herein and are known to the art. Pharmaceutically active agents are described herein and are known to the art. Immune-based therapeutic agents are described herein and are known to the art. Clinically approved active agents can comprise one or more FDA-approved active agents regardless of whether an active agent is a biologically active agent, a pharmaceutically active agent, or an immune-based therapeutic agent. In an aspect, a disclosed composition comprising AMB or BHH, or analogs or derivatives thereof, or a combination thereof can comprise (i) one or more active agents, (ii) one or more biologically active agents, (iii) one or more pharmaceutically active agents, (iv) one or more immune-based therapeutic agents, (v) one or more clinically approved agents, or (vi) a combination thereof. In an aspect, a disclosed composition comprising AMB or BHH, or analogs or derivatives thereof, or a combination thereof can comprise (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof.

A disclosed composition comprising AMB and/or BHH, or analogs or derivatives thereof, or a combination thereof, may be administered in various formats, such as tablet, capsule, syrup, dry powder sachets, inhalation solution/nebulization, drops, ampules, suppository, creams or ointments. For example, the composition may be administered in a tablet format. Tablets may be formulated for controlled release formulation, delayed release formulation, extended release formulation, sustained release formulation, pulsatile release formulation, or mixed immediate release formulation. Tablets may be effervescent. The composition may be administered in a capsule format. Capsules may be formulated for immediate release or sustained release, as examples. Capsules may be hard capsules or and soft capsules. Solution formats may be oil based, aqueous, or emulsions.

The composition comprising AMB and/or BHH, or analogs or derivatives thereof, or a combination thereof, may be administered via any suitable administration route. Example administration routes include parenteral administration, which may include intramuscular, intraarterial, or intravenous, as examples. Example administration routes include nonparenteral administration, such as oral, rectal, vaginal, nasal, mucosal, percutaneous, transdermal, or ophthalmic, as examples.

The composition comprising AMB and/or BHH, or analogs or derivatives thereof, or a combination thereof, may be administered in a suitable dosage format, via a suitable route of administration, such as any of those identified above, and in an effective daily dose to inhibit or ameliorate a SARS-CoV-2 infection, such as by any mechanism identified herein. The daily dose may be between 30 mg up to 2,000 mg. Example daily dosages may include greater than 200 mg, greater than 400 mg, greater than 500 mg, greater than 600 mg, greater than 700 mg, greater than 800 mg, greater than 900 mg, greater than 1000 mg, between 50 mg and 100 mg, between 100 mg and 200 mg, between 150 mg and 300 mg, between 200 mg and 1000 mg, between 500 mg and 1500 mg, between 450 mg and 1200 mg, between 500 mg and 2000 mg, between 1000 mg and 2000 mg, or any range between 30 mg and 2000 mg. The composition will typically be administered once daily, twice daily, or three times daily; however, additional administrations may be used.

In one example, AMB and/or BHH is administered at a total daily dose of 240 mg, 480 mg or 960 mg, twice daily. The administration route may be oral. In one example, AMB and/or BHH is administered orally in a tablet or capsule.

In an aspect, a disclosed composition can be administered to a subject. In an aspect, a subject can be a human. In an aspect, a human subject can be a participant in a clinical trial. In an aspect, a subject can be a human or a non-human primate diagnosed with or suspected of having a SARS-CoV-2 infection.

In an aspect, a disclosed composition comprising AMB or BHH, or analogs or derivatives thereof, or a combination thereof can be administered to a subject having one or more comorbidities. In an aspect, a disclosed composition comprising AMB or BHH, or analogs or derivatives thereof, or a combination thereof can comprise one or more active agents to treat or ameliorate one or more comorbidities. Comorbidities are known to the art and are discussed herein.

iii. Compositions for Inhibiting or Disrupting the Interaction Between ACE2 and Spike Protein Disclosed herein is a composition comprising an effective amount of AMB or BHH, or analogs or derivatives thereof, or a combination thereof, wherein the composition inhibits or disrupts the physical interaction of angiotensin converting enzyme 2 (ACE2) with the Spike (S) glycoprotein of SARS-CoV-2. Disclosed herein is a composition for inhibiting or disrupting the physical interaction of an angiotensin converting enzyme 2 (ACE2) with the Spike (S) glycoprotein of SARS-CoV-2 comprising an effective amount of AMB or BHH, or analogs or derivatives thereof, or a combination thereof. Disclosed herein is a composition for inhibiting or reducing viral infectivity in a subject comprising an effective amount of AMB or BHH, or analogs or derivatives thereof, or a combination thereof, wherein the composition inhibits or disrupts the physical interaction of angiotensin converting enzyme 2 (ACE2) with the Spike (S) glycoprotein of SARS-CoV-2, thereby inhibiting or reducing viral infectivity. Disclosed herein is a composition for inhibiting or ameliorating a SARS-CoV-2 infection in a subject comprising an effective amount of AMB or BHH, or analogs or derivatives thereof, or a combination thereof, wherein the composition inhibits or disrupts the physical interaction of angiotensin converting enzyme 2 (ACE2) with the Spike (S) glycoprotein of SARS-CoV-2, thereby inhibiting or ameliorating a SARS-CoV-2 infection. Disclosed herein is a composition for inhibiting or reducing viral entry into cells of a subject comprising an effective amount of AMB or BHH, or analogs or derivatives thereof, or a combination thereof, and wherein the composition inhibits or disrupts they physical interactions of angiotensin converting enzyme 2 (ACE2) and the Spike (S) glycoprotein of SARS-CoV-2, thereby inhibiting or reducing viral entry into cells of the subject.

In an aspect, a disclosed composition comprising one or more compounds belonging to the 8-hydroxyquinoline structural class or a disclosed composition comprising AMB or BHH, or analogs or derivatives thereof, or a combination thereof can inhibit or disrupt the physical interaction of angiotensin converting enzyme 2 (ACE2) with the Spike (S) glycoprotein of SARS-CoV-2. In an aspect, a disclosed composition comprising one or more compounds belonging to the 8-hydroxyquinoline structural class or a disclosed composition comprising AMB or BHH, or analogs or derivatives thereof, or a combination thereof can inhibit or reduce viral infectivity. In an aspect, a disclosed composition comprising one or more compounds belonging to the 8-hydroxyquinoline structural class or a disclosed composition comprising AMB or BHH, or analogs or derivatives thereof, or a combination thereof can inhibit or ameliorate a SARS-CoV-2 infection. In an aspect, a disclosed composition comprising one or more compounds belonging to the 8-hydroxyquinoline structural class or a disclosed composition comprising AMB or BHH, or analogs or derivatives thereof, or a combination thereof can inhibit or reduce viral entry into cells of the subject.

In an aspect, the receptor binding domain (RBD) of the Spike glycoprotein can bind to the metallopeptidase domain (MPD) of the ACE2 receptor.

AMB, BHH, and analogs or derivatives thereof are known to the art and are discussed herein. Pharmaceutically acceptable diluents, carriers, excipients, stabilizers, and combinations thereof are known to the art and are discussed herein.

In an aspect, a disclosed composition comprising AMB or BHH, or analogs or derivatives thereof, or a combination thereof can comprise one or more active agents, one or more biologically active agents, one or more pharmaceutically active agents, one or more immune-based therapeutic agents, one or more clinically approved agents, or a combination thereof. Biologically active agents are described herein and are known to the art. Pharmaceutically active agents are described herein and are known to the art. Immune-based therapeutic agents are described herein and are known to the art. Clinically approved active agents can comprise one or more FDA-approved active agents regardless of whether an active agent is a biologically active agent, a pharmaceutically active agent, or an immune-based therapeutic agent. In an aspect, a disclosed composition comprising AMB or BHH, or analogs or derivatives thereof, or a combination thereof can comprise (i) one or more active agents, (ii) one or more biologically active agents, (iii) one or more pharmaceutically active agents, (iv) one or more immune-based therapeutic agents, (v) one or more clinically approved agents, or (vi) a combination thereof. In an aspect, a disclosed composition comprising AMB or BHH, or analogs or derivatives thereof, or a combination thereof can comprise (i) one or more anti-bacterial agents, (ii) one or more anti-fungal agents, (iii) one or more anti-viral agents (such as, for example, remdesivir, favipiravir, merimepodib, etc.), (iv) one or more corticosteroids (such as, e.g., dexamethasone, prednisone, methylprednisolone, hydrocortisone, etc.), or (v) a combination thereof.

A disclosed composition comprising AMB and/or BHH, or analogs or derivatives thereof, or a combination thereof, may be administered in various formats, such as tablet, capsule, syrup, dry powder sachets, inhalation solution/nebulization, drops, ampules, suppository, creams or ointments. For example, the composition may be administered in a tablet format. Tablets may be formulated for controlled release formulation, delayed release formulation, extended release formulation, sustained release formulation, pulsatile release formulation, or mixed immediate release formulation. Tablets may be effervescent. The composition may be administered in a capsule format. Capsules may be formulated for immediate release or sustained release, as examples. Capsules may be hard capsules or and soft capsules. Solution formats may be oil based, aqueous, or emulsions.

In various embodiments, the composition comprising AMB and/or BHH, or analogs or derivatives thereof, or a combination thereof, may be administered via any suitable administration route. Example administration routes include parenteral administration, which may include intramuscular, intraarterial, or intravenous, as examples. Example administration routes include nonparenteral administration, such as oral, rectal, vaginal, nasal, mucosal, percutaneous, transdermal, or ophthalmic, as examples.

The composition comprising AMB and/or BHH, or analogs or derivatives thereof, or a combination thereof, may be administered in a suitable dosage format, via a suitable route of administration, such as any of those identified above, and in an effective daily dose to inhibit or ameliorate a SARS-CoV-2 infection, such as by any mechanism identified herein. The daily dose may be between 30 mg up to 2,000 mg. Example daily dosages may include greater than 200 mg, greater than 400 mg, greater than 500 mg, greater than 600 mg, greater than 700 mg, greater than 800 mg, greater than 900 mg, greater than 1000 mg, between 50 mg and 100 mg, between 100 mg and 200 mg, between 150 mg and 300 mg, between 200 mg and 1000 mg, between 500 mg and 1500 mg, between 450 mg and 1200 mg, between 500 mg and 2000 mg, between 1000 mg and 2000 mg, or any range between 30 mg and 2000 mg. The composition will typically be administered once daily, twice daily, or three times daily; however, additional administrations may be used.

In one example, AMB and/or BHH is administered at a total daily dose of 240 mg, 480 mg or 960 mg, twice daily. The administration route may be oral. In one example, AMB and/or BHH is administered orally in a tablet or capsule.

In an aspect, a disclosed composition can be administered to a subject. In an aspect, a subject can be a human. In an aspect, a human subject can be a participant in a clinical trial. In an aspect, a subject can be a human or a non-human primate diagnosed with or suspected of having a SARS-CoV-2 infection.

In an aspect, a disclosed composition comprising AMB or BHH, or analogs or derivatives thereof, or a combination thereof can be administered to a subject having one or more comorbidities. In an aspect, a disclosed composition comprising AMB or BHH, or analogs or derivatives thereof, or a combination thereof can comprise one or more active agents to treat or ameliorate one or more comorbidities. Comorbidities are known to the art and are discussed herein.

E. Kits

Disclosed herein is a kit comprising one or more disclosed compositions. In an aspect, a kit can comprise one or more compositions comprising a member of a 8-hydroxyquinoline structural class. In an aspect, a kit can comprise one or more compositions comprising a member of a benzylamine structural class. In an aspect, a kit can comprise one or more compositions comprising CLQ, CLBQ14, CLCQ, analogs thereof, derivatives thereof, or a combination thereof. In an aspect, a kit can comprise one or more compositions comprising AMB, BHH, analogs thereof, derivatives thereof, or a combination thereof. In an aspect, a kit can comprise one or more compositions comprising CLQ, CLBQ14, CLCQ, analogs thereof, derivatives thereof, or a combination thereof and one or more active agents. In an aspect, a kit can comprise one or more compositions comprising AMB, BHH, analogs thereof, derivatives thereof, or a combination thereof and one or more active agents. In an aspect, a disclosed kit can comprise at least two components constituting the kit. Together, the components constitute a functional unit for a given purpose (such as, for example, treating a subject diagnosed with or suspected of having a coronavirus infection like SARS-CoV-2). Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation. In an aspect, a kit for use in a disclosed method can comprise one or more containers holding a disclosed composition and a label or package insert with instructions for use. In an aspect, a kit can contain one or more additional agents (e.g., active agents, biologically active agents, pharmaceutically active agents, immune-based therapeutic agents, clinically approved agents, or a combination thereof). In an aspect, one or more active agents can treat, inhibit, and/or ameliorate one or more comorbidities in a subject. In an aspect, one or more active agents can treat, inhibit, and/or ameliorate a SARS-CoV-2 related infection and/or complication. In an aspect, suitable containers include, for example, bottles, vials, syringes, blister pack, etc. The containers can be formed from a variety of materials such as glass or plastic. The container can hold a disclosed composition or a pharmaceutical formulation comprising a disclosed composition and can have a sterile access port (for example the container may be an intravenous solution bag or a vial having a stopper pierceable by a hypodermic injection needle). The label or package insert can indicate that a disclosed composition or a pharmaceutical formulation comprising a disclosed composition can be used for treating, preventing, inhibiting, and/or ameliorating a coronavirus infection (e.g., SARS-CoV-2) or complications and/or symptoms associated with a coronavirus infection. A kit can comprise additional components necessary for administration such as, for example, other buffers, diluents, filters, needles, and syringes.

As introduced above, in some formulations may include a tablet. According to one embodiment, a method of making an immediate-release tablet containing AMB, BHH, CLQ, CLBQ14, and/or CLCQ includes a wet granulation method wherein the fine powder of containing AMB, BHH, CLQ, CLBQ14, and/or CLCQ is mixed with diluents (such as lactose or microcrystalline cellulose) and disintegrants (croscarmellose (2%), sodium starch gylcolate (5%), sodium carboxymethylcellulose, polyvinylpyrrolidone (PVP)); a binder solution is also prepared (such as aqueous solutions of povidone, cornstarch, methylcellulose, carboxymethylcellulose or glucose); the binder solution is mixed with the powder mixture to form an adhesive mass which can be granulated; the wet massed powder blend is then be screened using 6- to 12-mesh screen to prepare wet granules; the moist granules are dried in an oven at a controlled temperature not exceeding 55 C to a consistent weight; the dried granules are mixed with appropriate quantity of lubricant, such as magnesium stearate (1% to 2% of the weight of the granulation); the mixed granules are compressed in a single punch or multi-station tablet press fitted with the appropriate punches and dies.

VII. EXAMPLES

A. Examples Comprising CLQ, CLBQ14, and CLCQ
  Materials and Methods
  African Green Monkey Kidney Vero E6 cells (ATCC #CRL-1586, American Tissue Culture Type) were maintained using medium purchased from Gibco (modified eagle's medium (MEM) Gibco (#11095), 10% fetal bovine serum (HI FBS) Gibco (#14000), and Penicillin/Streptomycin (PS) Gibco (#15140); 10 U/mL penicillin and 10 µg/mL streptomycin (only in assay media)). For the SARS-CoV-2 infection induced cytopathic effect (CPE) assay, cells were grown in MEM/10% HI FBS and harvested in MEM/1% PS/supplemented with 2% HI FBS. Cells were batch inoculated with SARS-CoV-2 USA_WA1/2020 (M.O.I.~0.002), which resulted in 5-10% cell viability 72 hours post infection.

The small molecule inhibitors 5-chloro-7-iodo-8-quinolinol (Clioquinol, CLQ; C0187-Lot JJ01 SPGN) and 7-bromo-5-chloro-8-hydroxyquinoline (CLBQ14; B1190-P61JD-FD)) were purchased from TCI America whereas 5,7-dichloro-8-hydroxyquinoline (CLCQ; D64600-Lot #STBH7389) and Zinc Chloride ($ZnCl_2$; 208086-Lot #MKCL1763) were purchased from Sigma Aldrich. 10 mM stocks solutions of the inhibitors were prepared in dimethylsulfoxide (DMSO; D8418-Lot #SHBL5613) purchased from Sigma Aldrich. For the CPE assay, compound samples were serially diluted 2-fold in DMSO nine times and screened in duplicates. Assay Ready Plates (ARPs; Corning 3764BC) pre-drugged with test compounds (90 nL sample in 100% DMSO per well dispensed using a Labcyte (ECHO 550) are prepared in the Biosafety Level-2 (BSL-2) laboratory by adding 5 µL assay media to each well.

Compound cytotoxicity was assessed in a BSL-2 counter screen as follows using the Cell Titer-Glo Luminescent Cell Viability Assay.[6085] Host cells in media were added in 25 µL aliquots (4000 cells/well) to each well of assay ready plates prepared with test compounds as above. Cells only (100% viability) and cells treated with hyamine at 100 µM final concentration (0% viability) serve as the high and low signal controls, respectively, for cytotoxic effect in the assay. DMSO was maintained at a constant concentration for all wells (0.3%) as dictated by the dilution factor of stock test compound concentrations. After incubating plates at 37° C./5% $CO_2$ and 90% humidity for 72 hours, 30 µL CellTiter Glo (CTG) (G7573, Promega) was added to each well. Luminescence was read using a BMG CLARIOstar plate reader following incubation at room temperature for 10 minutes to measure cell viability.

The SARS-CoV-2 infection induced cytopathic effect (CPE) assay and cytotoxicity assays were generated and performed through a sub-contract to Southern Research Institute (SRI) (Birmingham, Alabama) from Texas Southern University (Houston, Texas). The CPE reduction assay was conducted at SRI to screen for antiviral agents in high throughput screening (HTS) format as previously described.[54,85] Briefly, Vero E6 cells selected for expression of the SARS-CoV-2 receptor (ACE2; angiotensin-converting enzyme 2) were used for the CPE assay. Cells were grown in MEM/10% HI FBS supplemented and harvested in MEM/1% PS/supplemented with 2% HI FBS. Cells were batch inoculated with SARS-CoV-2 (M.O.I.~ 0.002), which resulted in 5% cell viability 72 hours post infection. Compound samples were serially diluted 2-fold in DMSO nine times and screened in duplicates. Assay Ready Plates (ARPs; Corning 3764 BC black-walled, clear bottom plates) pre-drugged with test compounds (90 nL sample in 100% DMSO per well dispensed using a Labcyte (ECHO 550) were prepared in the BSL-2 lab by adding 5 µL assay media to each well. The plates were passed into the BSL-3 facility where a 25 µL aliquot of virus inoculated cells (4000 Vero E6 cells/well) was added to each well in Columns 3-22. The wells in Columns 23-24 contained virus infected cells only (no compound treatment). Prior to virus infection, a 25 µL aliquot of cells was added to Columns 1-2 of each plate for the cell only (no virus) controls. After incubating plates at 37° C./5% $CO_2$ and 90% humidity for 72 hours, 30 µL of Cell Titer-Glo (Promega) was added to each well. Luminescence was read using a Perkin Elmer Envision or BMG CLARIOstar plate reader following incubation at room temperature for 10 minutes to measure cell viability. Raw data from each test well was normalized to the average (Avg.) signal of non-infected cells (Avg. Cells; 100% inhibition) and virus infected cells only (Avg. Virus; 0% inhibition) to calculate % inhibition of CPE using the following formula: % inhibition=100*(Test Cmpd−Avg. Virus)/(Avg. Cells−Avg. Virus). The SARS CPE assay was conducted in BSL-3 containment with plates being sealed with a clear cover and surface decontaminated prior to luminescence reading. Reference compounds for CPE assay were made available by SRI.

ACE2 Inhibitor Screening Assay
  An ACE2 inhibitor screening assay kit with fluorogenic substrate (Catalogue #79923) was purchased from BPS Bioscience (San Diego, CA) and adapted to measure the exopeptidase activity of ACE2 in the presence and absence of inhibitors. The fluorescence assay was performed using a black flat-bottom 96-well plate with a final reaction volume of 50 µL following the manufacturer's instructions. 10 mM stock solutions of the compounds were prepared in Dimethyl sulfoxide (DMSO). Next, the compounds were serially diluted in DMSO as follows: 100 µM, 50 M, 10 µM, 1 µM, 0.5 µM, and 0.1 µM for CLQ and CLBQ14 as well as 10 µM and 1 µM for CLCQ. All experiments were performed in triplicates. Each plate contained a positive control of enzyme-treated with vehicle alone (2% DMSO) and a blank control with no enzyme. Briefly, each reaction contained 24 µL of purified recombinant human ACE2 protein (0.42 ng/L) in ACE2 buffer, 1 µL of compound at serially diluted concentrations, and 25 µL ACE2 fluorogenic substrate. The total reaction volume was 50 µL. The reaction mixtures were protected from light and incubated for 2.5 hours at room temperature (22° C.). Thereafter, the fluorescence intensities ($\lambda_{Excitation}$=535 nm, $\lambda_{Emission}$=595 nm) were measured using a Beckman Coulter DTX880 multimode plate reader. A similar experiment was conducted to measure and compare the exopeptidase activity of ACE2 in the presence and absence of Zinc Chloride ($ZnCl_2$) alone, CLBQ14 alone, and $ZnCl_2$ in combination with CLBQ14 at concentrations ranging from 100 μM to 100 nM. ZnCl$_2$ was serially diluted in water and a positive control of enzyme-treated with vehicle alone (water for ZnCl$_2$ only; DMSO for CLBQ14 alone; and water plus DMSO for ZnCl$_2$ and CLBQ14) was carried out for this experiment. The background hydrolysis was subtracted and the data was fitted to a four-parameter logistic (variable slope) equation using GraphPad prism software 8.4.3.

ACE2-Spike (RBD) Protein Interaction Assay

A Spike-ACE2 binding assay kit (Cat #CoV-SACE2-1, Lot #062320 7066) was purchased from RayBiotech (Norcross, GA). The in vitro enzyme-linked immunoabsorbent assay (ELISA) was adapted and performed in a transparent flat-bottom 96-well plate. 10 mM stock solutions of the compounds were prepared in Dimethyl sulfoxide (DMSO), with serially diluted the compounds in DMSO as follows: 100 μM, 50 μM, 10 μM, 5 μM, 1 μM, 0.5 μM, and 0.1 μM for CLQ, CLBQ14, and CLCQ. All experiments were performed in triplicates. Each plate contained positive controls (1% DMSO) and blank controls with no ACE2. Briefly, 1 μL of serially diluted compounds were incubated with recombinant SARS-CoV-2 Spike receptor binding domain (RBD) protein, pre-coated on the 96 well plates in 49 μL of 1× assay diluent buffer for 31 minutes at room temperature (22° C.) with shaking at 180 rpm. Next, 50 μL of ACE2 protein in 1× assay diluent buffer was added into the 96 well plate and incubated for 2.5 hours at room temperature (22° C.) with shaking at 180 rpm. Thereafter, the solution was discarded and the plate was washed consecutively four times with 300 μL 1× wash buffer followed by the addition of the detection antibody (anti-ACE2 goat antibody). The reaction was allowed to go on for 1 hour at room temperature (22° C.) with shaking at 180 rpm. Then, the solution was discarded and the wash step was repeated as described above. Next, the HRP-conjugated anti-goat IgG was added to each well and the reaction plate was further incubated for 1 hour at room temperature (22° C.) with shaking at 180 rpm. Again, the solution was discarded and the wash step was repeated as described above. Then, 100 μL of 3,3',5,5'-tetramethylbenzidine (TMB) one-step substrate was added to each well. The reaction mixtures were incubated in the dark at room temperature (22° C.) with shaking at 180 rpm for an additional 30 minutes and then stopped by the addition of 50 μL stop solution. The absorbance was read at 405 nm using a Beckman Coulter DTX880 multimode plate reader. The background hydrolysis was subtracted and the data was fitted to a special bell-shaped dose-response curve equation using GraphPad prism software 8.4.3.

Results and Discussion

Cytotoxicity Effects of CLQ and Analogues in Vero E6 Cells

The preliminary cytotoxicity of CLQ and its analogues (CLBQ14 and CLCQ) was determined using a Cell Titer-Glo Luminescent Cell Viability Assay.[85] The cytotoxic effects of the various compounds in Vero E6 cells measured at the 50% cytotoxic concentration (CC$_{50}$) of CLQ and its derivatives were all greater than 30 μM. When compared to the other reference compounds tested, CLQ and its analogues displayed lower percent minimum viability at higher concentrations. Similar percent maximum viability for CLQ pharmacophore and the other reference compounds at lower concentrations was observed (FIG. 8). This indicates that the cytotoxic effects may not be a concern at lower concentrations of CLQ and its analogues. FIG. 8 shows the cytotoxicity of clioquinol (CLQ) and analogues in Vero E6 Cells compared to reference inhibitors of SARS-CoV-2.

Efficacy of Clioquinol (CLQ) and Analogues Against SARS-CoV-2 Infection Induced Cytopathic Effect (CPE) in Vero E6 Cells To identify inhibitors of SARS-CoV-2 infection for potential treatment of COVID-19, the in vitro antiviral activity of CLQ and two of its derivatives, CLBQ14 and CLCQ, were examined using a standard luminescent-based high-throughput screening (HTS) platform[59,6054,85] for SARS-CoV-2 infection induced CPE in African Green Monkey Kidney Vero E6 cells. The three compounds inhibited SARS-CoV-2 infection induced CPE in vitro with 50% Inhibitory Concentration ($IC_{50}$) values in the low micromolar concentration (FIGS. 1A-1C). Amongst the three analogues tested, CLQ displayed the most potent antiviral activity in the CPE assay. Compared to its counterparts, CLBQ14 exhibited the highest maximum inhibition at about 102.96% inhibition at 30 μM. FIG. 6 shows the chemical structure and activity of Clioquinol (CLQ) and analogues against SARS-CoV-2 induced cytopathic effect (CPE) in Vero E6 cells.

The antiviral effects of CLBQ14 and its analogues were also compared with five other known inhibitors of SARS-CoV-2 in vitro: Chloroquine, Hydroxychloroquine, Remdesivir, Aloxistatin, and Calpain Inhibitor IV. The dose-response curves of the CLQ, CLBQ14, CLCQ and the reference compounds mentioned above were determined at multiplicities of infection (MOI) of about 0.002. The $IC_{50}$ for CLQ (12.62 μM) and its analogues [(CLBQ14, 14.69 μM) and (CLCQ, 16.30 μM)] were slightly lower than the $IC_{50}$ of Aloxistatin (16.72 μM), but moderately higher than Chloroquine (1.10 μM), Hydroxychloroquine (5.04 μM), Remdesivir (4.42 M), and Calpain Inhibitor IV (0.41 μM) (FIGS. 2A-2E). FIG. 7 shows the chemical structure and activity of reference inhibitors against SARS-CoV-2 induced cytopathic effect (CPE) in Vero E6 cells. This is the first report that CLQ and its analogues effectively inhibit the novel SARS-CoV-2 infection induced CPE.

Effects of CLQ and its Analogues on ACE2 Exopeptidase Activity

The effects of CLQ, CLBQ14, and CLCQ on the exopeptidase activity of rhACE2 were determined using a fluorometric assay provided by BPS Bioscience and adapted accordingly. BPS Bioscience's method for the ACE2 Inhibitor Screening Assay Kit can be found at https://bpsbioscience.com/pub/media/wysiwyg/79923.pdf.

The three compounds inhibited rhACE2 activity with similar $IC_{50}$ values in the low micromolar concentration with CLQ being the most potent amongst the three analogues tested, having an $IC_{50}$ of 5.36 μM. FIG. 9 shows the activity of clioquinol (CLQ) and analogues against ACE2 exopeptidase activity and ACE2 and SARS-CoV-2 spike (RBD) protein interaction. This is the first report that rhACE2 is a biochemical target of CLQ and its analogues.

Using the same fluorometric assay described above, the exopeptidase activity of rhACE2 was assessed in the presence of zinc chloride ($ZnCl_2$) alone, CLBQ14 alone, and $ZnCl_2$ in combination with CLBQ14 at concentrations ranging from 100 μM to 100 nM. In the presence of $ZnCl_2$ alone, rhACE2 displayed increasing exopeptidase activity. In the presence of $ZnCl_2$ in combination with CLBQ14, there was an increased shift in $IC_{50}$ value by over 28-fold compared to CLBQ14 alone (FIG. 3). The increasing concentrations of $ZnCl_2$ titrates the inhibitory effect of CLBQ14 on rhACE2 from concentrations ranging from above 5 μM-10 μM, which is consistent with the required optimal concentration range of Zinc for the exopeptidase activity of ACE2.[61]

Figure 4A:
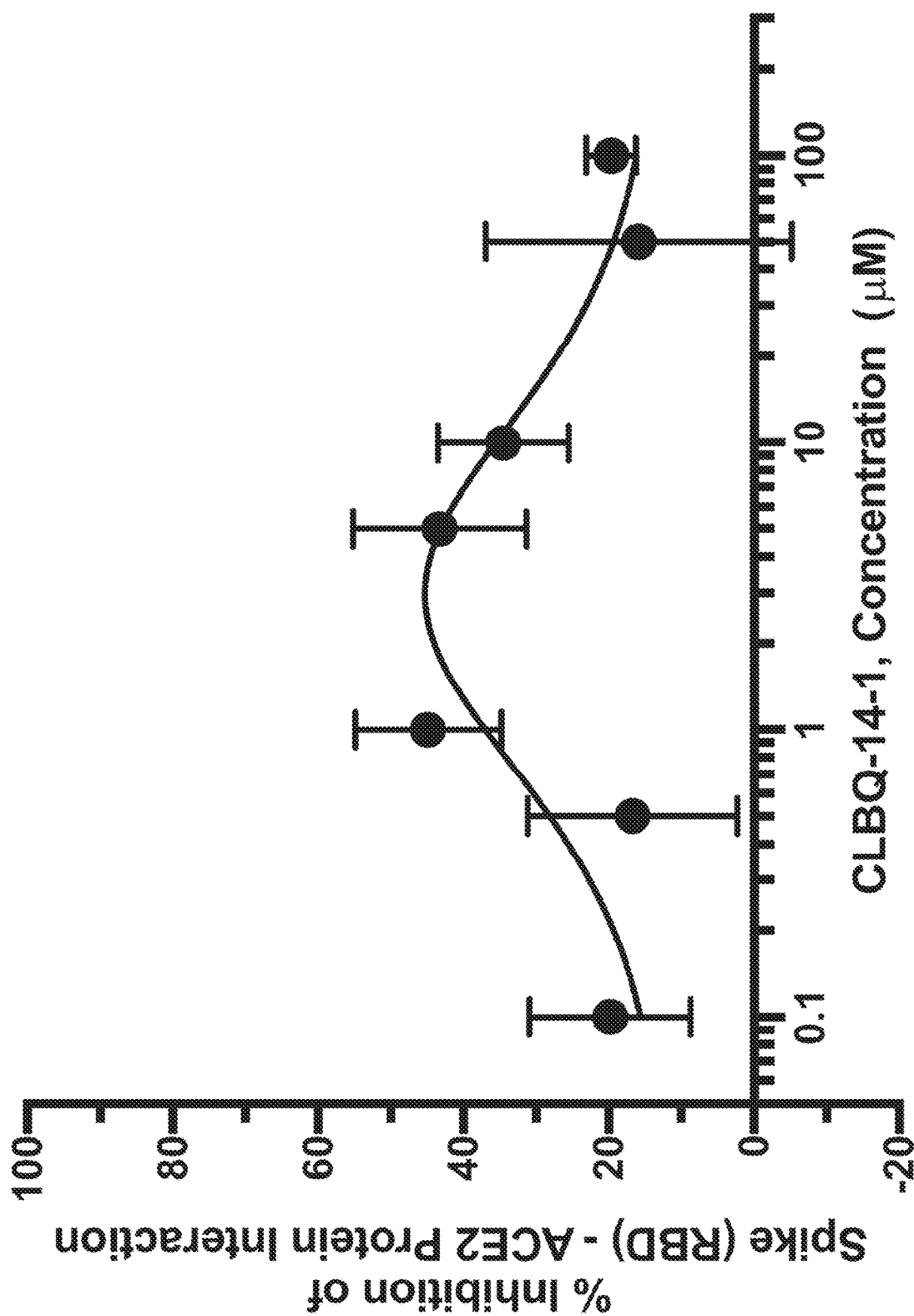
FIG. 4A-4C shows the inhibition of ACE2 and SARS-CoV-2 Spike (RBD) protein interaction by clioquinol (CLQ) and analogues: (A) CLBQ14, (B) CLCQ, and (C) CLQ.
Figure 4B:
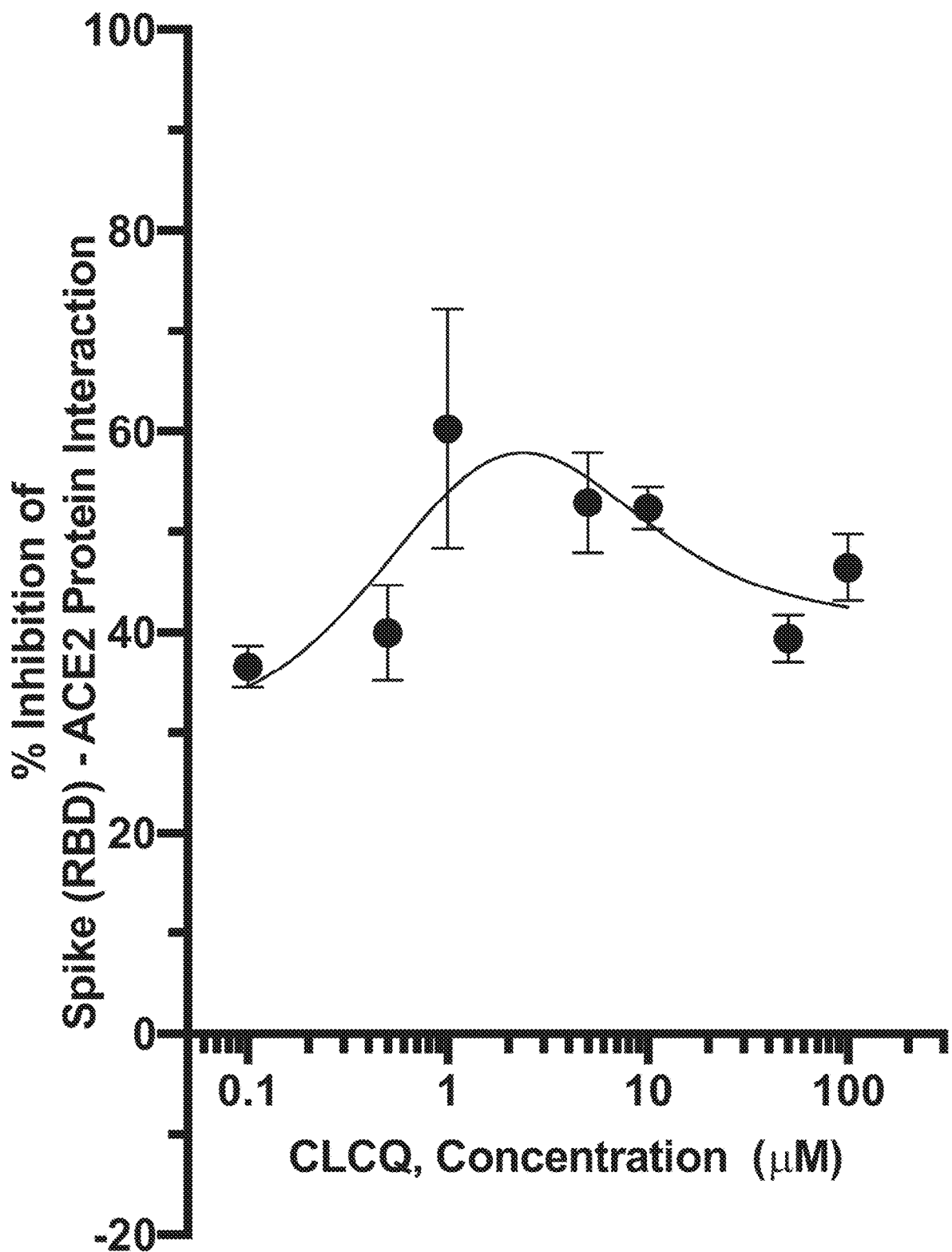
Figure 4C:
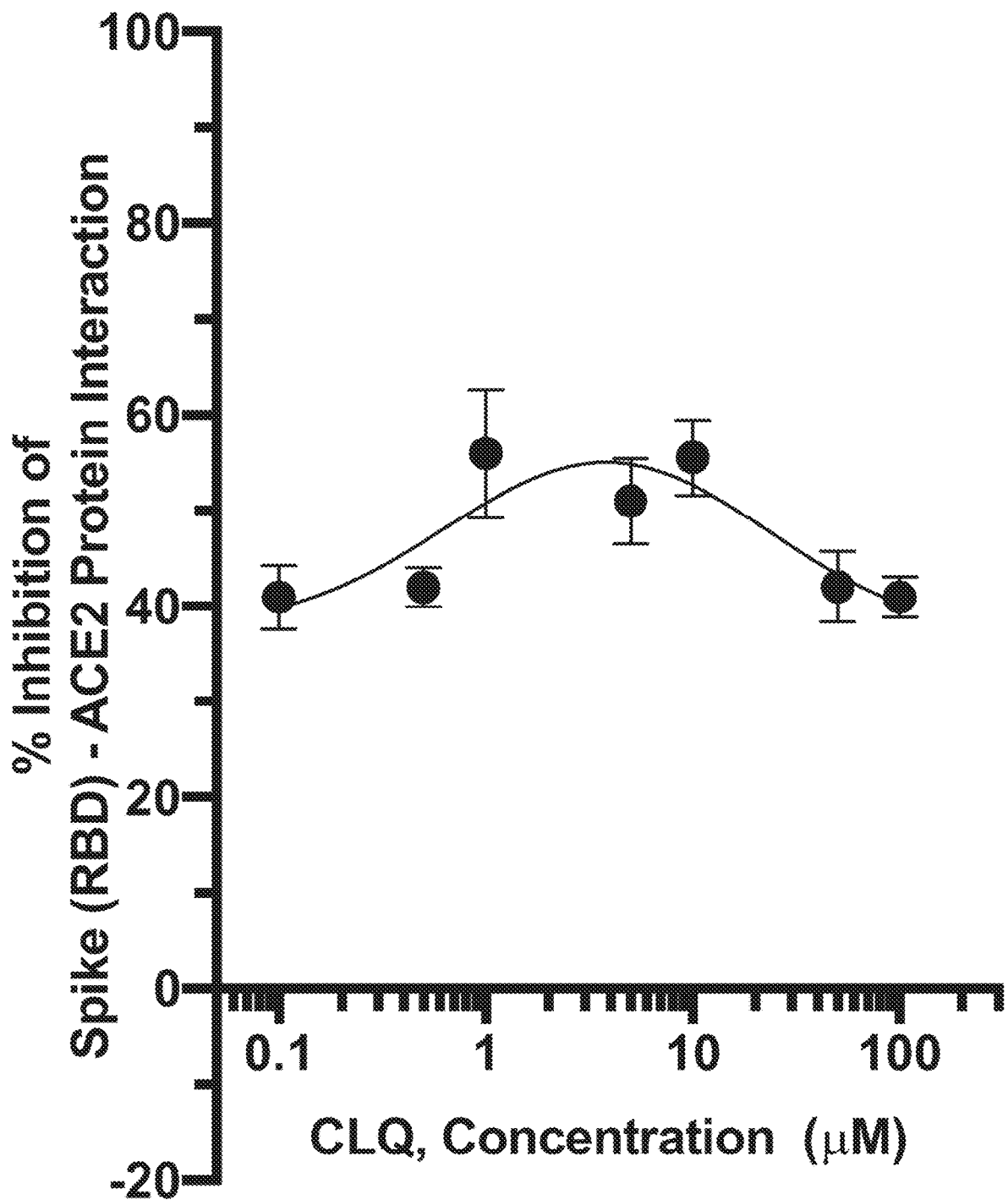

Effects of CLQ and its Analogues on ACE2 and Spike (RBD) Protein Interaction The interaction of human ACE2 receptor with SARS-CoV-2's Spike protein receptor binding domain is an important first step in the process of viral entry into host cells.[98,100,105,108] Using an adapted in vitro enzyme-linked immunoabsorbent assay (ELISA) (see User Manual for RayBio® COVID-19 Spike-ACE2 binding assay kit available at https://doc.raybiotech.com/pdf/Manual/CoV-SACE2_2020.07.09.pdf), the effect of CLQ, CLBQ14, and CLCQ on the binding affinity of rhACE2 and RBD of S protein was examined at concentrations ranging from 100 µM to 100 nM. A unique bell shaped dose-response curve for the three compounds was observed, which showed higher inhibition of ACE2-Spike (RBD) protein interaction at lower compound concentrations compared to higher concentrations (FIGS. 4A-4C). The bell shaped curve generated two $IC_{50}$ values ($IC_{50\_1}$ and $IC_{50\_2}$). These three compounds had similar $IC_{50}$ values in the low micromolar concentration ranging from 0.85 µM to 2.76 µM for $IC_{50\_1}$; however, CLQ displayed a higher $IC_{50\_2}$ at 18.15 µM. The unconventional dose response curve observed in this interaction assay can indicate one or more additional binding sites or one or more additional targets for the CLQ pharmacophore, such as, for example, other sites on ACE2 or the Spike (RBD) protein. These data represent the first report that CLQ and its analogues inhibited and interfered with the binding between human ACE2 receptor and SARS-CoV-2 Spike RBD protein.

Summary of Experiments Comprising CLQ, CLBQ14, and CLCQ

Given the ongoing COVID-19 pandemic and the emerging virulence of novel SARS-CoV-2 strains, there is an urgent need to accelerate the development of effective therapeutic agents as countermeasures against this pathogen. Here, three independent approaches were applied to investigate the possibility of CLQ and its analogues as potential inhibitors of the SARS-CoV-2 infection in vitro. These data represent the first report that CLQ and its analogues target rhACE2. CLQ significantly inhibited binding of rhACE2 receptor with SARS-CoV-2 Spike (RBD) protein and SARS-CoV-2 infection induced CPE.

CLQ, a known metal chelator and zinc ionophore, was successfully identified and characterized as an inhibitor of SARS-CoV-2 infection induced CPE. CLQ and two structural analogues of CLQ (CLBQ14 and CLCQ) displayed similar potent inhibition in the low micromolar range against SARS-CoV-2 infection induced CPE, rhACE2 activity, and its interaction with Spike Protein. The dose-response curves of antiviral effects of CLQ and its analogues was compared with five other known inhibitors of SARS-CoV-2 in vitro: Chloroquine, Hydroxychloroquine, Remdesivir, Aloxistatin, and Calpain Inhibitor IV. CLQ's potency was better than Aloxistatin, but lower than the other reference inhibitors FIGS. 2A-2E. Because the Vero E6 cells used for the SARS-CoV-2 infection induced CPE assay were first sorted by flow cytometry by SRI for selection of cells that had higher levels of ACE2 expression to increase the efficiency of infection, the observed $IC_{50}$ values may be higher than the actual values in cells that are does not have high levels of ACE2 expression. The $IC_{50}$ values of the compounds in the biochemical assays were much lower than the $IC_{50}$ in the cellular antiviral assay.

The cytotoxic effects of the compounds in Vero E6 cells were assessed and CLQ and its analogues displayed lower percent minimum viability at higher concentrations compared to the other reference compounds tested. Similar percent maximum viability for CLQ pharmacophore and the other reference compounds were measured at lower concentrations (FIG. 8). The date indicate that cytotoxic effects may not be a concern at lower concentrations of CLQ and its analogues. In addition, the observed $IC_{50}$ values for inhibition of rhACE exopeptidase activity and rhACE2-RBD interaction were in the low micromolar range, which can indicate the need for lower concentrations for in vivo activity.

A correlation between the high potency of CLQ compared to its other two analogues in the antiviral screen, inhibition of rhACE2 metalloprotease activity, and its ability to disrupt the binding of rhACE2 with SARS-CoV-2 Spike (RBD) protein was consistently observed during these studies. Amongst the three compounds, CLQ displayed the highest potency in the three independent assays; except for $IC_{50}$_2. Clioquinol and its derivatives can act as metal chelators and zinc ionophores, which can be capable of modulating underlying molecular and physiologic switches in metal homeostatis in vivo.[1-2,4-6,8,14,21,24-25,32,46,50,64,75,77,81,84,87,91-92,111-112.] These data demonstrate that CLQ and its analogs can target ACE2, a zinc metalloenzyme and essential cellular receptor for SARS-CoV-2 entry into host cells.[98,100,105,108]

ACE 2, a carboxypeptidase, is a type I integral membrane protein made up of about 805 amino acids belonging to the large family of zinc metalloproteases with high level of structural homology for a catalytic motif, containing one characteristic HEXXH+E zinc-binding consensus sequence and binding sites for inhibitor or specific substrates respectively.[94] The first crystalline structures of the metallopeptidase domain of ACE2 revealed a large inhibitor-dependent hinge bending movement of one catalytic subdomain relative to the other that brings important amino acid residues into position for catalysis,[94] which was similar to observed subdomains on other zinc metalloproteases. The residues critical for coordinating the binding of zinc to ACE2 are $His^{374}$ $His^{378}$ and $Glu^{402}$, according to earlier x-ray structures.[94] Moreover, ACE2 is activated by monovalent anions and also known to contain an inhibitor-specific anion binding site.[94,96] The reported optimal/stabilized metalloprotease activity of recombinant soluble human ACE2 was found to be in the presence of 10 μM $ZnCl_2$[96]

As described herein, CLQ or CLBQ14 alone significantly decreased exopeptidase activity for ACE2 in the low micromolar concentrations. An increased shift in $IC_{50}$ values was identified in exopeptidase activity in the presence of $ZnCl_2$ in combination with CLBQ14 by over 28 fold compared to CLBQ14 alone, indicating that CLBQ14 can be working through zinc chelation, interaction, and/or coordination. The data provided herein demonstrate that rhACE2 is a target for the CLQ pharmacophore. These data also demonstrate a potential reversibility of inhibition as well as one or more avenues of inhibition. For example, the concentration of CLBQ14 can be titrated with excess $ZnCl_2$, thus rendering it pre-occupied and unavailable to inhibit rhACE2 exopeptidase activity. Or, there can be potential competition for the similar binding sites on rhACE2.

Targeting ACE2 requires caution as it is imprudent to permanently inactivated its exopeptidase activity or other activities. CLQ is a weak metal chelator and zinc ionophore that can shuttle free zinc across the membrane.[18,112] Because of these properties, CLQ may temporarily or reversibly affect ACE2 function and prevent its interaction with SARS-CoV-2 RBD protein without permanently inhibiting its exopeptidase function. The crystal structure of full length human ACE2 revealed that the RBD on SARS-CoV-2 S1 binds directly to the metallopeptidase domain (MPD) of ACE2 receptor,[105,108] which consists of amino acid residues that coordinates zinc. Using a sensitive ELISA, CLQ and its analogues potently disrupted the interaction of ACE2 and Spike (RBD) protein (with CLQ being the most potent). CLQ and its derivatives bound to ACE2 and surprisingly inhibited exopeptidase activity. Unlike the CLQ pharmacopore, other studies revealed that MLN-4760, which is also known as (S,S)-2-{1-Carboxy-2-[3-(3,5-dichloro-benzyl)-3H-imidazol-4-yl]-ethylamino}-4-methyl-pentanoi c acid, is a potent inhibitor of ACE2 exopeptidase activity. But, MLN-4760 did not disrupt ACE2-Spike interaction in several coronaviruses, including SARS-CoV, SARS-CoV-2, and NL63S.[53,67] Studies have shown that the MLN-4760 binding site on ACE2 is different than the site where RBD interacts with ACE2.[49,67,94] Moreover, mutations in the catalytic site required for exopeptidase activity of ACE2 had no effect on Spike RBD binding to ACE2.[94] However, as shown in the work described herein, CLQ can affect ACE2 by reversibly chelating its zinc ion (which is involved in its activity) as well as interfere with the ACE2-RBD interaction. Although CLQ was the most potent amongst the 3 analogs, except for $IC_{50\_2}$, preliminary structure activity relationship studies (SAR) revealed that the other two derivatives are comparable to CLQ as both show potent inhibition of rhACE2-RBD interaction as well as inhibition of antiviral and anti-rhACE2 activity. Alternative analogues can avoid the same adverse effects experienced with CLQ in the past.

The impact of the COVID-19 pandemic on human health, healthcare systems, and the global economy has imposed an urgent call and a pressing need for the development of novel antivirals.[74] Using a multi-prong approach, CLQ and two of its analogues (CLBQ14 and CLCQ) were examined and characterized as potent inhibitors of SARS-CoV-2 infection induced CPE in vitro, rhACE2 metalloprotease activity, and the binding of rhACE2 with SARS-CoV-2 spike (RBD) protein necessary for viral entry. These data provide strong cellular and biochemical evidence that CLQ, CLBQ14, and CLCQ can serve as new anti-COVID19 treatments.

B. Examples Comprising AMB and BHH

Materials and Methods

African Green Monkey Kidney Vero E6 cells (ATCC #CRL-1586, American Tissue Culture Type) were maintained using medium purchased from Gibco (modified eagle's medium (MEM) Gibco (#11095), 10% fetal bovine serum (HI FBS) Gibco (#14000), and Penicillin/Streptomycin (PS) Gibco (#15140); and 10 U/mL penicillin and 10 µg/mL streptomycin (only in assay media)). For the SARS-CoV-2 infection induced cytopathic effect (CPE) assay, cells were grown in MEM/10% HI FBS and harvested in MEM/1% PS/supplemented with 2% HI FBS. Cells were batch inoculated with SARS-CoV-2 USA_WA1/2020 (M.O.I.~0.002), which resulted in 5%-10% cell viability 72 hours post-infection.

Compounds and Preparation of Stock Solutions 10 mM stocks solutions of the inhibitors in dimethyl sulfoxide (DMSO; D8418-Lot #SHBL5613) were purchased from Sigma Aldrich. Ambroxol Hydrochloride (AMB) (A9797—Lot #BCCB1637) and Bromhexine Hydrochloride (BHH) (17343—Lot #BCBJ8156V) were also purchased from Sigma Aldrich. Both compound samples were serially diluted 2-fold in DMSO nine times and screened in duplicates for the SARS-CoV-2 infection induced cytopathic effect (CPE) assay. The reference compounds used for the CPE and cytotoxicity assays were made available by SRI. Assay Ready Plates (ARPs; Corning 3764BC) pre-drugged with test compounds (90 nL sample in 100% DMSO per well dispensed using a Labcyte (ECHO 550)) were prepared in the Biosafety Level-2 (BSL-2) laboratory by adding 5 µL assay media to each well.

The SARS-CoV-2 infection induced cytopathic effect (CPE) assay and cytotoxicity assays were generated and performed through a sub-contract to Southern Research Institute (SRI) (Birmingham, Alabama) from Texas Southern University (Houston, Texas). The CPE reduction assay was conducted using a high throughput-screening (HTS) format as previously described.[54,85] Specifically, Vero E6 cells selected for expression of the SARS-CoV-2 receptor (ACE2 or angiotensin-converting enzyme 2) were used for the CPE assay. Cells were grown in MEM/10% HI FBS supplemented and harvested in MEM/1% PS/supplemented with 2% HI FBS. Cells were batch inoculated with SARS-CoV-2 (M.O.I.~ 0.002), which resulted in 5% cell viability 72 hours post-infection. Compound samples were serially diluted 2-fold in DMSO nine times and screened in duplicates. Assay Ready Plates (ARPs; Corning 3764 BC black-walled, clear bottom plates) pre-drugged with test compounds (90 nL sample in 100% DMSO per well dispensed using a Labcyte (ECHO 550)) were prepared in the BSL-2 lab by adding 5 µL assay media to each well. The plates were passed into the BSL-3 facility where a 25 µL aliquot of virus inoculated cells (4000 Vero E6 cells/well) was added to each well in Columns 3-22. The wells in Columns 23-24 contained virus infected cells only (no compound treatment). Prior to virus infection, a 25 µL aliquot of cells was added to Columns 1-2 of each plate for the cell only (no virus) controls. After incubating plates at 37° C./5% $CO_2$ and 90% humidity for 72 hours, 30 µL of Cell Titer-Glo (Promega) was added to each well. Luminescence was read using a Perkin Elmer Envision or BMG CLARIOstar plate reader following incubation at room temperature for 10 minutes to measure cell viability. Raw data from each test well were normalized to the average (Avg.) signal of non-infected cells (Avg. Cells; 100% inhibition) and virus infected cells only (Avg. Virus; 0% inhibition) to calculate % inhibition of CPE using the following formula: % inhibition=100*(Test Cmpd−Avg. Virus)/(Avg. Cells−Avg. Virus). The SARS CPE assay was conducted in BSL-3 containment with plates being sealed with a clear cover and surface decontaminated prior to luminescence reading.

The cytotoxicity of AMB and BHH was assessed in a BSL-2 counter screen using the Cell Titer-Glo Luminescent Cell Viability Assay as previously described.[85] Briefly, host cells in media were added in 25 µL aliquots (4000 cells/well) to each well of assay ready plates prepared with test compounds as above. Cells only (100% viability) and cells treated with hyamine at 100 µM final concentration (0% viability) serve as the high and low signal controls, respectively, for cytotoxic effect in the assay. DMSO was maintained at a constant concentration for all wells (0.3%) as dictated by the dilution factor of stock test compound concentrations. After incubating plates at 37° C./5% $CO_2$ and 90% humidity for 72 hours, 30 µL CellTiter Glo (CTG) (G7573, Promega) was added to each well. To measure cell viability, luminescence was read using a BMG CLARIOstar plate reader following incubation at room temperature for 10 minutes.

The SARS-CoV-2 Spike—ACE2 binding assay kits (Cat #CoV-SACE2-1, Lot #062320 7066 and Lot #081120 7066) were purchased from RayBiotech (Norcross, GA). The manufacturer's protocol[80] for the kits was adapted to determine the effect of AMB and BHH on the interaction between SARS-CoV-2 Spike (RBD) protein and recombinant human ACE2. The in vitro enzyme-linked immunoabsorbent assay (ELISA) was performed in a transparent flat-bottom 96-well plate. A 10 mM stock solutions of the compounds in Dimethyl sulfoxide (DMSO) with serially dilutions of the compounds in DMSO as follows: 100 µM, 50 µM, 10 µM, 5 µM, 1 µM, 0.5 µM, and 0.1 µM for AMB and BHH. All experiments were performed in triplicate. Each plate contained positive controls (1% DMSO) and blank controls with no ACE2. Specifically, 1 µL of serially diluted compounds was incubated with recombinant SARS-CoV-2 Spike receptor binding domain (RBD) protein, pre-coated on the 96 well plates in 49 µL of 1× assay diluent buffer for 30 mins at room temperature (22° C.) with shaking at 180 rpm. Then, 50 µL of ACE2 protein in 1× assay diluent buffer was added into the 96 well plate and incubated for 2.5 hours at room temperature (22° C.) with shaking at 180 rpm. Thereafter, the solution was discarded and the plate was washed consecutively four times with 300 µL 1× wash buffer, followed by the addition of the detection antibody (anti-ACE2 goat antibody). The reaction was allowed to go on proceed for 1 hour at room temperature (22° C.) with shaking at 180 rpm. Then, the solution was discarded and the wash step was repeated as described above. Next, the HRP-conjugated anti-goat IgG was added to each well, and the reaction plate was further incubated for 1 hour at room temperature (22° C.) with shaking at 180 rpm. Again, the solution was discarded and the wash step was repeated as described above. Then, 100 µL of 3,3',5,5'-tetramethylbenzidine (TMB) one-step substrate was added to each well, and reaction mixtures were incubated in the dark at room temperature (22° C.) with shaking at 180 rpm for 30 mins. The reaction was stopped by the addition of 50 µL stop solution. The absorbance was read at 405 nm using a Beckman Coulter DTX880 multimode plate reader. The background hydrolysis was subtracted and the data was fitted to a special bell-shaped dose-response curve equation using GraphPad prism software 8.4.3.

Results and Discussion

Cytotoxicity Effects of AMB and BHH in Vero E6 Cells

Using a Cell Titer-Glo Luminescent Cell Viability Assay[85], the cytotoxicity of AMB and BHH was examined. The cytotoxic effects of the reference compounds in Vero E6 cells were also determined. The 50% cytotoxic concentration ($CC_{50}$) of AMB and BHH were greater than 30 µM. When compared to the reference compounds tested, AMB and BHH displayed slightly higher percent maximum and minimum viability at the concentrations tested. Between the two compounds, a higher percent minimum viability for AMB (113.95%) was observed compared to BHH (103.87%) at 30 µM. These cytotoxicity results are consistent with the known clinical safety profiles of both compounds with AMB showing better pharmacokinetic and safety profiles compared to BHH.[102]

Efficacy of AMB and BHH Against SARS-CoV-2 Infection Induced Cytopathic Effect (CPE) in Vero E6 Cells.

To identify inhibitors of SARS-CoV-2 infection for potential treatment of COVID-19, the in vitro antiviral activity of AMB and BHH was examined using a standard luminescent-based high-throughput screening (HTS) platform[54,85] for SARS-CoV-2 infection induced CPE in African Green Monkey Kidney Vero E6 cells. BHH inhibited SARS-CoV-2 infection induced CPE in vitro with 50% Inhibitory Concentration ($IC_{50}$) value at about 21.72 µM. AMB's $IC_{50}$ was greater than 30 µM, which was the highest concentration tested FIGS. 5A-5B. At this maximum concentration, AMB displayed 14.25% inhibition of SARS-CoV-2 induced CPE and BHH exhibited the highest maximum inhibition (about 91.08% inhibition) at 30 µM.

The antiviral effects of AMB and BHH were compared to that of five other known inhibitors of SARS-CoV-2 in vitro: (i) Calpain Inhibitor IV, (ii) Chloroquine, (iii) Remdesivir, (iv) Hydroxychloroquine, and (v) Aloxistatin. The $IC_{50}$ for most of the reference compounds (Calpain Inhibitor IV (0.29 µM), Chloroquine (3.56 µM), Hydroxychloroquine (5.16 µM), Remdesivir (8.54 µM)) were lower than the $IC_{50S}$ values for BHH and AMB. However, the $IC_{50}$ of Aloxistatin (21.78 µM) was similar to that of BHH (21.72 µM). The $IC_{50}$ values observed for the reference compounds are consistent with earlier reports.[44-47][13,51,74,99] While other cellular studies tested BHH and AMB at certain or single concentrations,[9,37,93] these are the first data to demonstrate the $IC_{50}$ determination for BHH and AMB against the novel SARS-CoV-2 infection induced CPE.

Effects of AMB and BHH on Spike (RBD) Protein Interaction

Figure 5A:
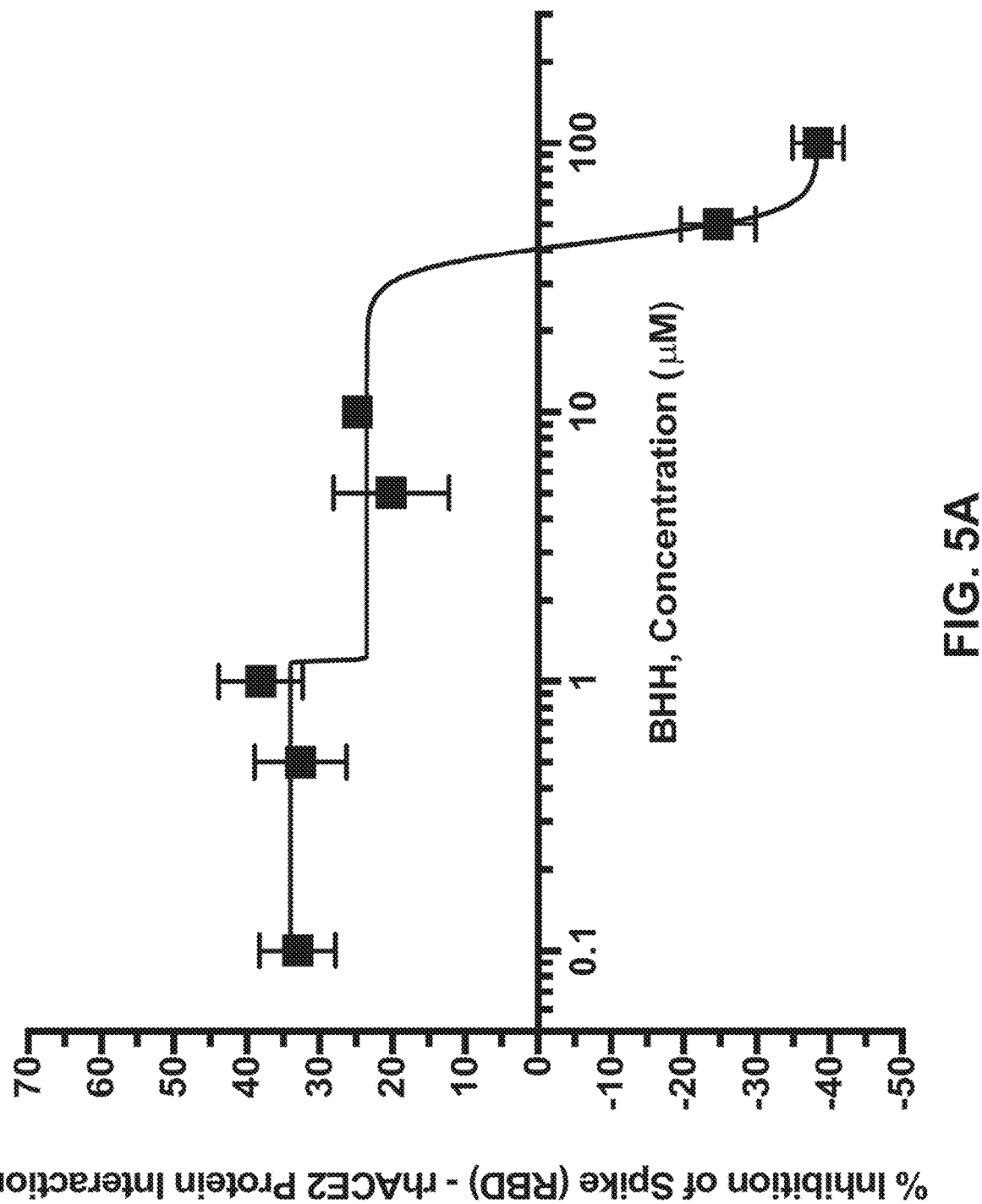
FIG. 5A-5B shows the effect of (A) Bromhexine Hydrochloride (BHH) and (B) Ambroxol Hydrochloride (AMB) on the interaction of rhACE2 with SARS-CoV-2 Spike (RBD) Glycoprotein Interaction.
Figure 5B:
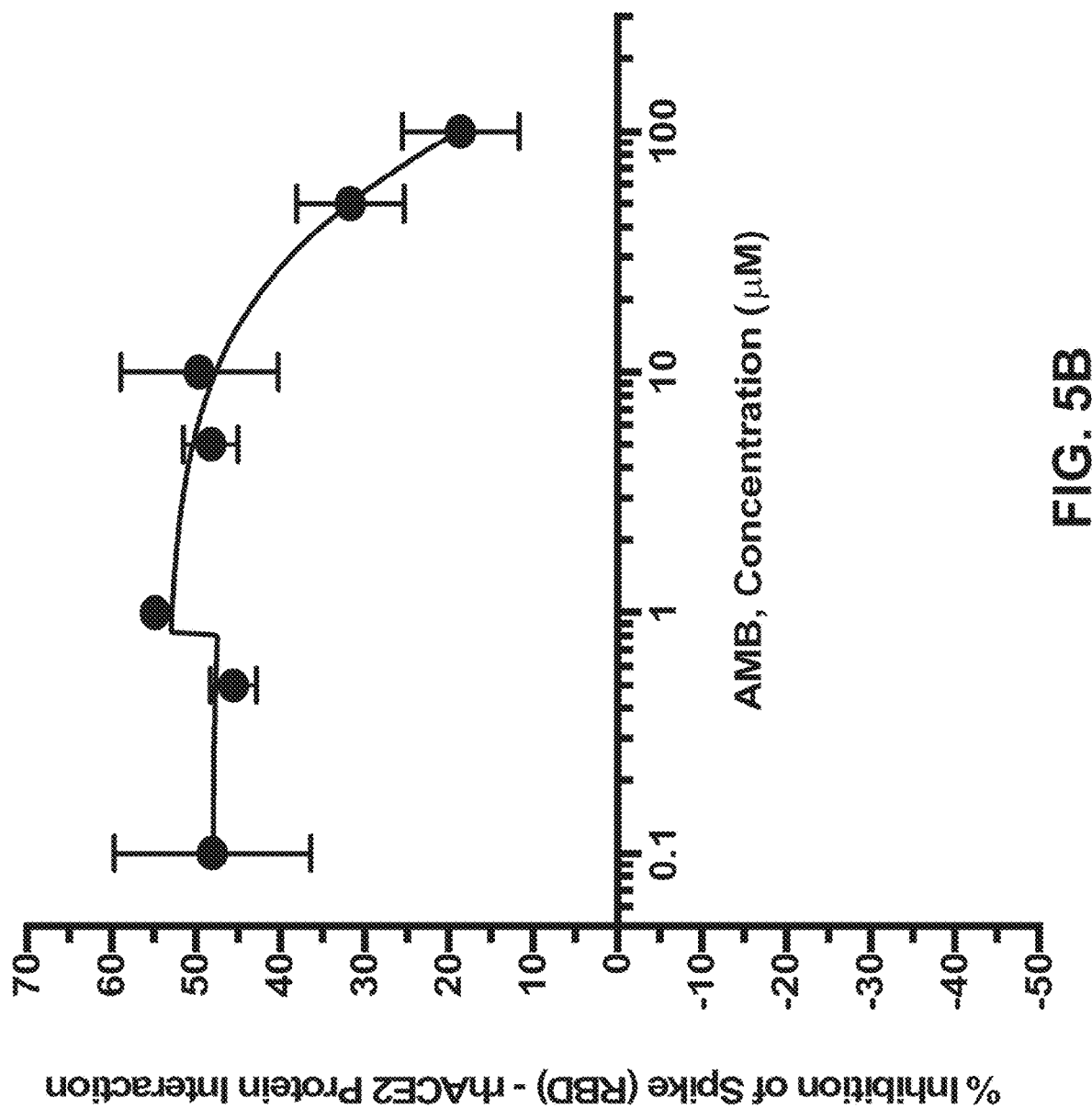

The effects of AMB and BHH on the binding affinity of rhACE2 and RBD of S glycoprotein at concentrations ranging from 100 µM to 100 nM were tested using an adapted in vitro enzyme-linked immunoabsorbent assay (ELISA).[80] A unique dose-response curve for both compounds (using the special bell shape curve model) was identified. AMB displayed the highest inhibition of the Spike (RBD)-rhACE2 protein interaction at lower micromolar concentrations (ranging from 100 nM to 10 µM) than compared to higher concentrations of AMB from 50 µM (FIG. 5B). BHH inhibited the binding of the Spike (RBD) glycoprotein to the rhACE2 receptor at lower concentrations ranging from 100 nM to 10 µM, but enhanced the interaction at higher concentrations (i.e., from 50 µM) (FIG. 5A). Hence, the bell-shaped model generated two $IC_{50}$ values ($IC_{50\_1}$ and $IC_{50\_2}$) (FIG. 9). At the concentrations tested, AMB did not produce a stimulation or enhancement of binding of SARS-CoV-2's Spike (RBD) protein to rhACE2 receptor. Using the bell curve model, however, the GraphPad software generated a second $IC_{50}$ at 232 µM for AMB, which was greater than the highest tested concentration (100 µM). The unconventional dose response curve observed in this protein interaction assay can be intrinsic to the mode of inhibition. Alternatively, it can be an indicator of one or more additional binding sites and/or targets (e.g., other sites on rhACE2 or the Spike (RBD) glycoprotein). This is the first report to show that AMB inhibited and interfered with the binding between rhACE2 receptor and SARS-CoV-2 S (RBD) glycoprotein in vitro and that BHH inhibited this interaction at lower concentrations and enhanced this interaction at higher concentrations.

Summary of Experiments Comprising AMB and BHH

The crystal structure of full length human ACE2 revealed that the RBD on SARS-CoV-2 S1 binds directly to the metallopeptidase domain (MPD) of ACE2 receptor.[98,100,105,107] Here, AMB and BHH were examined as potential effectors of the interaction between SARS-CoV-2's Spike glycoprotein receptor binding domain and recombinant human ACE2 receptor, which is an interaction that is important in the pathways required for viral entry into host cells[105] and initiation of pathogenesis. Using a sensitive ELISA[80], AMB and BHH modulated the interaction of rhACE2 and S (RBD) with AMB being the most potent effector. Significant inhibition of the interaction between the Spike (RBD) of SARS-CoV-2 and rhACE2 by AMB at low micromolar concentrations provided strong evidence that this pharmacophore is a novel SARS-CoV-2 entry inhibitor and a potential COVID-19 therapeutic. The data also demonstrated that BHH enhanced the interaction between Spike (RBD) protein and rhACE2 at higher concentrations and inhibited it at lower concentrations. This is the first report describing these two compounds as potent effectors of the binding of the Spike (RBD) protein to rhACE2.

The unconventional dose-response curve observed in the interaction studies indicates that there can be more than one binding site on rhACE2 and/or the Spike (RBD) glycoprotein for BHH and AMB, which can elicit potent inhibition of interaction at lower micromolar concentrations. This can also explain the enhancement of interaction by BHH at higher concentrations. To this end, a molecular dynamic study revealed that two different regions within the RBD of the Spike glycoproteins of SARS-CoV-2 interacted differently with ACE2 in the presence of high salt concentrations (E1 was more hydrophobic while E2 favored more polar interactions).[52]

The effect of AMB and BHH on SARS-CoV-2 infection induced CPE in vitro was also examined using a simple and rapid cellular high throughput screening assay.[54,85] While AMB was more potent than BHH against the rhACE2-RBD interaction, AMB had a higher $IC_{50}$ than BHH in the CPE assay for antiviral activity. The $IC_{50}$ values of the compounds in the cellular CPE assay were much higher than the $IC_{50s}$ in the rhACE2-Spike (RBD) protein interaction assay, although the special bell curve produced two $IC_{50s}$ due to the mode of inhibition at lower concentrations versus higher concentrations. Together, the data provided herein demonstrate that AMB targeted a novel protein-protein interaction.

A comparative analysis of the dose-response curves of antiviral activity and cytotoxicity of AMB and BHH with five other known inhibitors ("reference compounds") of SARS-CoV-2 in vitro was performed. The $IC_{50}$ range for BHH and AMB were similar to that of Aloxistatin, but higher than the other reference compounds (i.e., Chloroquine, Hydroxychloroquine, Remdesivir, and Calpain Inhibitor IV). The cytotoxicity of AMB and BHH in Vero E6 cells, however, displayed higher percent maximum and minimum viability at the concentrations tested when compared to the reference compounds. Moreover, AMB had a slightly higher percent minimum viability when compared to BHH, which is consistent with other reported safety studies for both compounds that demonstrate that AMB has superior safety profile than BHH.[102] Thus, AMB and its progenitor BHH can be used as chemical probes to study the biology of host-pathogen interaction in the context of SARS-CoV-2 infections, particularly in the pre-clinical development of novel entry inhibitors.

Both AMB and BHH have been used for clinically for treatment of respiratory conditions because of their multiple pharmacologic effects and safety profile.[28,60,73,76,113] In addition to their impact on lung physiology and function with regards to mucociliary clearance, mucokinetic properties, and stimulation of surfactant production, they have also elicited anti-inflammatory, antioxidative and anesthetic effects.[28,60,73,76,113] Both compounds induced cellular autophagic-lysosome pathway.[16,23,58] AMB has also reportedly been involved in the modulation of the homeostasis of ions such as hydrogen, calcium, and sodium.[27,102] Moreover, previous studies have shown that both AMB and BHH could enhance the lung levels of certain antibiotics when used in combination.[16,23] Additionally, AMB has gained attention clinically as a potential drug for treatment of neurodegenerative diseases.[57,58,]

Previously, AMB has been shown to inhibit certain viruses in vitro and in vivo. One proposed mechanism included preventing the release of RNA into the cytoplasm by increasing the endosomal pH.[106,109] BHH demonstrated inhibitory activity against TMPRSS2 at low micromolar concentrations.[53] However, unlike AMB and BHH, Camostat, another known TMPRSS2 inhibitor reversed TMPRSS2-mediated enhancement of SARS-CoV-2 infection.[37] This indicates that AMB and BHH can have additional modes of action.[37] The data provided herein demonstrate that AMB and BHH are effectors of the RBD-rhACE2 interaction further the understanding of SARS-CoV-2 inhibition.

REFERENCES

The following references cited herein are hereby incorporated by reference.

1 Adlard, P. A. et al. Rapid Restoration of Cognition in Alzheimer's Transgenic Mice with 8-Hydroxy Quinoline Analogs Is Associated with Decreased Interstitial Aβ. Neuron 59, (2008).
2 Andersson, D. A., Gentry, C., Moss, S. & Bevan, S. Clioquinol and pyrithione activate TRPA1 by increasing intracellular Zn2+. Proceedings of the National Academy of Sciences of the United States of America 106, (2009).
3 Ansarin, Khalil, Tolouian, Ramin, Ardalan, Mohammadreza, Taghizadieh, Ali, Varshochi, Mojtaba, Teimouri, Soheil, Vaezi, Tahere, Valizadeh, Hamed, Saleh, Parviz, Safiri, Saeid, Chapman K R. Effect of bromhexine on clinical outcomes and mortality in COVID-19 patients: A randomized clinical trial. BioImpacts. 2020; 10(4):7. doi: 10.34172/bi.2020.27
4 Auld, D. S., Kawaguchi, H., Livingston, D. M. & Vallee, B. L. RNA dependent DNA polymerase (reverse transcriptase) from avian myeloblastosis virus: a zinc metalloenzyme. Proceedings of the National Academy of Sciences of the United States of America 71, 2091-2095 (1974).
5 Ayton, S., Lei, P. & Bush, A. I. Biometals and Their Therapeutic Implications in Alzheimer's Disease. Neurotherapeutics vol. 12 (2015).
6 Bednarz-Prashad, A. J. & John, E. I. Effect of clioquinol, an 8-hydroxyquinoline derivative, on rotavirus infection in mice. The Journal of infectious diseases 148, (1983).
7 Belouzard, S., Chu, V. C. & Whittaker, G. R. Activation of the SARS coronavirus spike protein via sequential proteolytic cleavage at two distinct sites. Proceedings of the National Academy of Sciences of the United States of America (2009) doi:10.1073/pnas.0809524106.
8 Bohlmann, L. et al. Chemical synergy between ionophore PBT2 and zinc reverses antibiotic resistance. mBio 9, (2018).
9 Bradfute S B, Ye C, Clarke E C, Kumar S, Timmins G S, Deretic V. Ambroxol and Ciprofloxacin Show Activity Against SARS-CoV2 in Vero E6 Cells at Clinically-Relevant Concentrations. bioRxiv. Published online 2020. doi:10.1101/2020.08.11.245100
10 Cahoon, L. The curious case of clioquinol. Nature Medicine 15, (2009).
11 Capel, R. A. et al. Hydroxychloroquine reduces heart rate by modulating the hyperpolarization-activated current If: Novel electrophysiological insights and therapeutic potential. Heart Rhythm 12, 2186-2194, https://doi:10.1016/j.hrthm.2015.05.027 (2015).
12 Chaudhry R, Dranitsaris G, Mubashir T, Bartoszko J, Riazi S. A country level analysis measuring the impact of government actions, country preparedness and socioeconomic factors on COVID-19 mortality and related health outcomes. EClinicalMedicine. 2020; 0(0):100464. doi: 10.1016/j.eclinm.2020.100464

13 Chen C Z, Shinn P, Itkin Z, et al. Drug Repurposing Screen for Compounds Inhibiting the Cytopathic Effect of SARS-CoV-2. bioRxiv. Published online Aug. 18, 2020: 2020.08.18.255877. doi:10.1101/2020.08.18.255877

14 Cherny, R. A. et al. PBT2 reduces toxicity in a *C. elegans* model of polyQ aggregation and extends lifespan, reduces striatal atrophy and improves motor performance in the R6/2 mouse model of Huntington's disease. Journal of Huntington's Disease 1, (2012).

15 Chikhale R v., Gupta V K, Eldesoky G E, Wabaidur S M, Patil S A, Islam M A. Identification of potential anti-TMPRSS2 natural products through homology modelling, virtual screening and molecular dynamics simulation studies. Journal of Biomolecular Structure and Dynamics. Published online 2020. doi:10.1080/07391102.2020.1798813

16 Choi S W, Gu Y, Peters R S, et al. Ambroxol Induces Autophagy and Potentiates Rifampin Antimycobacterial Activity. Antimicrobial Agents and Chemotherapy. 2018; 62(9). doi:10.1128/aac.01019-18

17 Choi Y, Bowman J W, Jung J U. Autophagy during viral infection—A double-edged sword. Nature Reviews Microbiology. 2018; 16(6). doi:10.1038/s41579-018-0003-6

18 Colvin, R. A. et al. Insights into Zn2+ homeostasis in neurons from experimental and modeling studies. American Journal of Physiology—Cell Physiology 294, (2008).

19 Coronavirus (COVID-19) Update: FDA Issues Emergency Use Authorization for Potential COVID-19 Treatment, May 1 (2020). Retrieved from https://www.fda.gov/news-events/press-announcements/coronavirus-covid-19-update-fda-issues-emergency-use-authorization-potential-covid-19-treatment 20 Cox, E. H. & McLendon, G. L. Zinc-dependent protein folding. Current Opinion in Chemical Biology vol. 4 (2000).

21 Darby, C. M. & Nathan, C. F. Killing of non-replicating *Mycobacterium tuberculosis* by 8-hydroxyquinoline. Journal of Antimicrobial Chemotherapy 65, (2010).

22 de Souza A S, Rivera J D, Almeida V M, et al. Molecular dynamics reveals complex compensatory effects of ionic strength on the SARS-CoV-2 Spike/hACE-2 interaction. bioRxiv. Published online Jan. 1, 2020: 2020.08.25.267351. doi:10.1101/2020.08.25.267351

23 Deretic V, Timmins G S. Enhancement of lung levels of antibiotics by ambroxol and bromhexine. Expert Opinion on Drug Metabolism and Toxicology. 2019; 15(3). doi: 10.1080/17425255.2019.1578748

24 Ding, W. Q., Lin, B., Vaught, J. L., Yamauchi, H. & Lind, S. E. Anticancer activity of the antibiotic clioquinol. Cancer Research (2005) doi:10.1158/0008-5472.CAN-04-3577.

25 Ding, W. Q., Yu, H. J. & Lind, S. E. Zinc-binding compounds induce cancer cell death via distinct modes of action. Cancer Letters 271, (2008).

26 Domingo P, Mur I, Pomar V, Corominas H, Casademont J, de Benito N. The four horsemen of a viral Apocalypse: The pathogenesis of SARS-CoV-2 infection (COVID-19). EBioMedicine. 2020; 58. doi:10.1016/j.ebiom.2020.102887

27 Fois G, Hobi N, Felder E, et al. A new role for an old drug: Ambroxol triggers lysosomal exocytosis via pH-dependent Ca2+ release from acidic Ca2+ stores. Cell Calcium. 2015; 58(6). doi:10.1016/j.ceca.2015.10.002

28 Gent M, Knowlson P A, Rime F J. Effect of bromhexine on ventilatory capacity in patients with a variety of chest diseases. Lancet. 1969; 2(7630). doi:10.1016/s0140-6736(69)90702-8

29 Giglione, C., Vallon, O. & Meinnel, T. Control of protein life-span by N-terminal methionine excision. EMBO Journal 22, (2003).

30 Guan, W. et al. Clinical characteristics of coronavirus disease 2019 in China. New England Journal of Medicine 382, (2020).

31 Gui, M. et al. Cryo-electron microscopy structures of the SARS-CoV spike glycoprotein reveal a prerequisite conformational state for receptor binding. Cell Research 27, (2017).

32 Haase, H., Overbeck, S. & Rink, L. Zinc supplementation for the treatment or prevention of disease: Current status and future perspectives. Experimental Gerontology vol. 43 (2008).

33 Hamming, I. et al. Tissue distribution of ACE2 protein, the functional receptor for SARS coronavirus. A first step in understanding SARS pathogenesis. Journal of Pathology (2004) doi:10.1002/path.1570.

34 Harmer, D., Gilbert, M., Borman, R. & Clark, K. L. Quantitative mRNA expression profiling of ACE 2, a novel homologue of angiotensin converting enzyme. FEBS Letters (2002) doi:10.1016/S0014-5793(02)03640-2.

35 Hoffmann M, Kleine-Weber H, Schroeder S, et al. SARS-CoV-2 Cell Entry Depends on ACE2 and TMPRSS2 and Is Blocked by a Clinically Proven Protease Inhibitor. Cell. 2020; 181(2). doi:10.1016/j.cell.2020.02.052

36 Horby P, Lim W S, Emberson J, et al. Effect of Dexamethasone in Hospitalized Patients with COVID-19: Preliminary Report. medRxiv. Published online Jan. 1, 2020: 2020.06.22.20137273. doi:10.1101/2020.06.22.20137273

37 Hörnich B F, GroBkopf A K, Schlagowski S, Tenbusch M, Neipel F, Hahn A S. SARS-CoV-2 and SARS-CoV spike-mediated cell-cell fusion differ in the requirements for receptor expression and proteolytic activation and are not inhibited by Bromhexine. bioRxiv. Published online Jan. 1, 2020:2020.07.25.221135. doi:10.1101/2020.07.25.221135

38 Huang, C. et al. Clinical features of patients infected with 2019 novel coronavirus in Wuhan, China. The Lancet 395, (2020).

39 Imai, Y. et al. Angiotensin-converting enzyme 2 protects from severe acute lung failure. Nature 436, 112-116 (2005).

40 Johns Hopkins Center for Systems Science and Engineering. Coronavirus resource center: COVID-19 dashboard by the Center for Systems Science and Engineering (CSSE) at Johns Hopkins University (JHU). https://coronavirus.jhu.edu/map.html 41 Kam, Y. W. et al. Cleavage of the SARS coronavirus spike glycoprotein by airway proteases enhances virus entry into human bronchial epithelial cells in vitro. PLoS ONE 4, (2009).

42 Kirchdoerfer, R. N. et al. Pre-fusion structure of a human coronavirus spike protein. Nature 531, (2016).

43 Kono, R. Subacute myelo-optico-neuropathy, a new neurological disease prevailing in japan. Japanese Journal of Medical Science and Biology 24, (1971).

44 Kuba, K. et al. A crucial role of angiotensin converting enzyme 2 (ACE2) in SARS coronavirus-induced lung injury. Nature Medicine (2005) doi: 10.1038/nm1267.

45 Lal S, Bhalla K K. A controlled trial of bromhexine ('Bisolvon') in out-patients with chronic bronchitis. Current Medical Research and Opinion. 1975; 3(2). doi: 10.1185/03007997509113648

46 Lannfelt, L. et al. Safety, efficacy, and biomarker findings of PBT2 in targeting Abeta as a modifying therapy for Alzheimer's disease: a phase IIa, double-blind, randomised, placebo-controlled trial. The Lancet Neurology vol. 7 (2008).

47 Li F, Li W, Farzan M, Harrison S C. Structural biology: Structure of SARS coronavirus spike receptor-binding domain complexed with receptor. Science. Published online 2005. doi:10.1126/science.1116480

48 Li F. Receptor Recognition Mechanisms of Coronaviruses: a Decade of Structural Studies. Journal of Virology. 2015; 89(4). doi:10.1128/jvi.02615-14

49 Li, W. et al. Receptor and viral determinants of SARS-coronavirus adaptation to human ACE2. EMBO Journal 24, (2005).

50 Lind, S. E., Park, J. S. & Drexler, J. W. Pyrithione and 8-hydroxyquinolines transport lead across erythrocyte membranes. Translational Research 154, (2009).

51 Liu J, Cao R, Xu M, et al. Hydroxychloroquine, a less toxic derivative of chloroquine, is effective in inhibiting SARS-CoV-2 infection in vitro. Cell Discovery. 2020; 6(1). doi:10.1038/s41421-020-0156-0

52 Lowther, W. T. & Matthews, B. W. Structure and function of the methionine aminopeptidases. Biochimica et Biophysica Acta—Protein Structure and Molecular Enzymology vol. 1477 (2000).

53 Lucas J M, Heinlein C, Kim T, et al. The androgen-regulated protease TMPRSS2 activates a proteolytic cascade involving components of the tumor microenvironment and promotes prostate cancer metastasis. Cancer Discovery. 2014; 4(11). doi:10.1158/2159-8290.CD-13-1010

54 Maddox C B, Rasmussen L, White E L. Adapting Cell-Based Assays to the High-Throughput Screening Platform: Problems Encountered and Lessons Learned. Journal of Laboratory Automation. 2008; 13(3). doi: 10.1016/j.jala.2008.02.002

55 Madjid, M., Safavi-Naeini, P., Solomon, S. D. & Vardeny, O. Potential Effects of Coronaviruses on the Cardiovascular System: A Review. JAMA Cardiology (2020). doi: 10.1001/jamacardio.2020.1286.

56 Madu, I. G., Roth, S. L., Belouzard, S. & Whittaker, G. R. Characterization of a Highly Conserved Domain within the Severe Acute Respiratory Syndrome Coronavirus Spike Protein S2 Domain with Characteristics of a Viral Fusion Peptide. Journal of Virology 83, (2009).

57 Maegawa G H B, Tropak M B, Buttner J D, et al. Identification and characterization of ambroxol as an enzyme enhancement agent for Gaucher disease. Journal of Biological Chemistry. 2009; 284(35). doi:10.1074/jbc.M109.012393

58 Magalhaes J, Gegg M E, Migdalska-Richards A, Schapira A H. Effects of ambroxol on the autophagy-lysosome pathway and mitochondria in primary cortical neurons. Scientific Reports. 2018; 8(1). doi:10.1038/s41598-018-19479-8

59 Maggio R, Corsini G U. Repurposing the mucolytic cough suppressant and TMPRSS2 protease inhibitor bromhexine for the prevention and management of SARS-CoV-2 infection. Pharmacological Research. 2020; 157. doi: 10.1016/j.phrs.2020.104837

60 Malerba M, Ragnoli B. Ambroxol in the 21st century: Pharmacological and clinical update. Expert Opinion on Drug Metabolism and Toxicology. 2008; 4(8). doi: 10.1517/17425255.4.8.1119

61 Mao, L. et al. Neurological Manifestations of Hospitalized Patients with COVID-19 in Wuhan, China: A Retrospective Case Series Study. SSRN Electronic Journal (2020) doi:10.2139/ssrn.3544840.

62 Mao, X. & Schimmer, A. D. The Toxicology of Clioquinol. Toxicology Letters vol. 182 (2008).

63 Mathewson, A. C. et al. Interaction of severe acute respiratory syndrome-coronavirus and NL63 coronavirus spike proteins with angiotensin converting enzyme-2. Journal of General Virology 89, (2008).

64 McInerney, M. P. et al. Ionophore and Biometal Modulation of P-glycoprotein Expression and Function in Human Brain Microvascular Endothelial Cells. Pharmaceutical Research 35, (2018).

65 Meade, T. W. Subacute myelo optic neuropathy and clioquinol. An epidemiological case history for diagnosis. British Journal of Preventive and Social Medicine vol. 29 (1975).

66 Millet, J. K. & Whittaker, G. R. Host cell proteases: Critical determinants of coronavirus tropism and pathogenesis. Virus Research 202, (2015).

67 Nami, B., Ghanaeian, A., Ghanaeian, K. & Nami, N. The Effect of ACE2 Inhibitor MLN-4760 on the Interaction of SARS-CoV-2 Spike Protein with Human ACE2: A Molecular Dynamics Study. (2020) doi: 10.26434/chemrxiv.12159945.

68 Napolitano F, Gambardella G, Carrella D, Gao X, di Bernardo D. Computational Drug Repositioning and Elucidation of Mechanism of Action of Compounds against SARS-CoV-2. Published online Apr. 16, 2020. Accessed Sep. 4, 2020. https://arxiv.org/abs/2004.07697

69 National Center for Advancing Translational Sciences. AMBROXOL HYDROCHLORIDE. Accessed Sep. 4, 2020. https://drugs.ncats.io/drug/CC995ZMV90

70 National Center for Biotechnology Information. PubChem Compound Summary for CID 108013, Ambroxol hydrochloride. Accessed Sep. 4, 2020. https://pubchem.ncbi.nlm.nih.gov/compound/Ambroxol-hydrochloride 71 National institute of Health (NIH). Potential Antiviral Drugs Under Evaluation for the Treatment of COVID-19. Last updated on Aug. 27, 2020. Accessed, Sep. 5, 2020. https://www.covid19treatmentguidelines.nih.gov/antiviral-therapy/

72 Nishiga, M., Wang, D. W., Han, Y., Lewis, D. B., & Wu, J. C. COVID-19 and cardiovascular disease: from basic mechanisms to clinical perspectives. Nat Rev Cardiol (2020).

73 Nobata K, Fujimura M, Ishiura Y, Myou S, Nakao S. Ambroxol for the prevention of acute upper respiratory disease. Clinical and Experimental Medicine. 2006; 6(2). doi:10.1007/s10238-006-0099-2

74 Olaleye O A, Kaur M, Onyenaka C, Adebusuyi T. Discovery of Clioquinol and Analogues as Novel Inhibitors of Severe Acute Respiratory Syndrome Coronavirus 2 Infection, ACE2 and ACE2-Spike Protein Interaction In Vitro. bioRxiv: the preprint server for biology. Published online 2020. doi:10.1101/2020.08.14.250480

75 Olaleye, O. et al. Characterization of Clioquinol and Analogs as Novel Inhibitors of Methionine Aminopeptidases from *Mycobacterium tuberculosis*. Tuberculosis (Edinb), https://doi: 10.1016/j.tube.2011.10.012 (2011).

76 Olivieri D, Zavattini G, Tomasini G, et al. Ambroxol for the Prevention of Chronic Bronchitis Exacerbations: Long-Term Multicenter Trial. Respiration. 1987; 51(1). doi:10.1159/000195274

77 Perez, D. R., Sklar, L. A. & Chigaev, A. Clioquinol: To harm or heal. Pharmacology and Therapeutics vol. 199 (2019).

78 Plasencia-Garcia, B. O. et al. Drug-Drug interactions between COVID-19 treatments and antipsychotics drugs: integrated evidence from 4 databases and a systematic review. https://doi.org/10.1101/2020.06.04.20122416

79 Potential Antiviral Drugs Under Evaluation for the Treatment of COVID-19, National institute of Health (NIH), COVID-19 Treatment Guidelines, July 24 (2020). Retrieved from https://www.covid19treatmentguidelines.nih.gov/antiviral-therapy/

80 RayBiotech. COVID-19 Spike-ACE2 binding assay kit. Published 2020. https://doc.raybiotech.com/pdf/Manual/CoV-SACE2_2020.07.09.pdf 81 Ritchie, C. W. et al. Metal-Protein Attenuation with Iodochlorhydroxyquin (Clioquinol) Targeting Aβ Amyloid Deposition and Toxicity in Alzheimer Disease: A Pilot Phase 2 Clinical Trial. Archives of Neurology 60, (2003).

82 Roden, Dan M., et al. "Considerations for drug interactions on QTc in exploratory COVID-19 (coronavirus disease 2019) treatment." Circulation (2020).

83 Sanders J M, Monogue M L, Jodlowski T Z, Cutrell J B. Pharmacologic Treatments for Coronavirus Disease 2019 (COVID-19): A Review. JAMA—Journal of the American Medical Association. 2020; 323(18):1824-1836. doi: 10.1001/jama.2020.6019

84 Schimmer, A. D. et al. A phase I study of the metal ionophore clioquinol in patients with advanced hematologic malignancies. Clinical Lymphoma, Myeloma and Leukemia 12, (2012).

85 Severson W E, Shindo N, Sosa M, et al. Development and validation of a high-throughput screen for inhibitors of SARS CoV and its application in screening of a 100,000-compound library. Journal of Biomolecular Screening. 2007; 12(1). doi:10.1177/1087057106296688

86 Shen L W, Mao H J, Wu Y L, Tanaka Y, Zhang W. TMPRSS2: A potential target for treatment of influenza virus and coronavirus infections. Biochimie. 2017; 142. doi:10.1016/j.biochi.2017.07.016

87 Shi, L. et al. Clioquinol improves motor and non-motor deficits in MPTP-induced monkey model of Parkinson's disease through AKT/mTOR pathway. Aging 12, (2020).

88 Slomski A. No Benefit for Lopinavir-Ritonavir in Severe COVID-19. JAMA—Journal of the American Medical Association. 2020; 323(20):1999. doi: 10.1001/jama.2020.6793

89 Song, W., Gui, M., Wang, X. & Xiang, Y. Cryo-EM structure of the SARS coronavirus spike glycoprotein in complex with its host cell receptor ACE2. PLoS Pathogens (2018) doi:10.1371/journal.ppat.1007236.

90 South, A. M., Diz, D. I. & Chappell, M. C. COVID-19, ACE2, and the cardiovascular consequences. American journal of physiology. Heart and circulatory physiology 318, (2020).

91 Tavares, G. de S. V. et al. Antileishmanial Activity, Cytotoxicity and Mechanism of Action of Clioquinol Against *Leishmania infantum* and *Leishmania amazonensis* Species. Basic and Clinical Pharmacology and Toxicology 123, (2018).

92 Tavares, G. S. V. et al. A clioquinol-containing Pluronic®F127 polymeric micelle system is effective in the treatment of visceral leishmaniasis in a murine model. Parasite 27, (2020).

93 Touret F, Gilles M, Barral K, et al. In vitro screening of a FDA approved chemical library reveals potential inhibitors of SARS-CoV-2 replication. Scientific Reports. 2020; 10(1). doi:10.1038/s41598-020-70143-6

94 Towler P, Staker B, Prasad S G, et al. ACE2 X-Ray Structures Reveal a Large Hinge-bending Motion Important for Inhibitor Binding and Catalysis. Journal of Biological Chemistry. 2004; 279(17):17996-18007. doi: 10.1074/jbc.M311191200

95 Verma H K, Merchant N, Verma M K, et al. Current updates on the European and WHO registered clinical trials of coronavirus disease 2019 (COVID-19). Biomedical Journal. Published online 2020. doi:https://doi.org/10.1016/j.bj.2020.07.008

96 Vickers, C. et al. Hydrolysis of biological peptides by human angiotensin-converting enzyme-related carboxypeptidase. Journal of Biological Chemistry 277, (2002).

97 Volenti S, Marenco G. Italian multicenter study on the treatment of chronic obstructive lung disease with bromhexine: A double-blind placebo-controlled trial. Respiration. 1989; 56(1-2). doi:10.1159/000195772

98 Walls A C, Park Y J, Tortorici M A, Wall A, McGuire A T, Veesler D. Structure, Function, and Antigenicity of the SARS-CoV-2 Spike Glycoprotein. Cell. 2020; 181(2). doi:10.1016/j.cell.2020.02.058

99 Wang M, Cao R, Zhang L, et al. Remdesivir and chloroquine effectively inhibit the recently emerged novel coronavirus (2019-nCoV) in vitro. Cell Research. 2020; 30(3). doi:10.1038/s41422-020-0282-0

100 Wang Q, Zhang Y, Wu L, et al. Structural and Functional Basis of SARS-CoV-2 Entry by Using Human ACE2. Cell. 2020; 181(4). doi: 10.1016/j.cell.2020.03.045

101 Warner, F. J., Guy, J. L., Lambert, D. W., Hooper, N. M. & Turner, A. J. Angiotensin converting enzyme-2 (ACE2) and its possible roles in hypertension, diabetes and cardiac function. Letters in Peptide Science (2003) doi: 10.1007/BF02442567.

102 Weiser T. Ambroxol: A CNS Drug? CNS Drug Reviews. 2008; 14(1). doi:10.1111/j.1527-3458.2007.00032.x 103 WHO. Coronavirus Disease 2019 (COVID-19) Situation Report.; 2020. Published 2020. Accessed Mar. 6, 2020. https://www.who.int/docs/default-source/coronaviruse/situation-reports/20200306-sitrep-46-covid-19.pdf?sfvrsn=96b04adf_4

104 World Health Organization. Director-General's opening remarks at the media briefing on COVID-19. Published 2020. Accessed Mar. 10, 2020. https://www.who.int/dg/speeches/detail/who-director-general-s-opening-remarks-at-the-media-briefing-on-covid-19-11-march-2020

105 Wrapp D, Wang N, Corbett K S, et al. Cryo-EM structure of the 2019-nCoV spike in the prefusion conformation. Science. Published online 2020. doi: 10.1126/science.aax0902

106 Yamaya M, Nishimura H, Nadine L K, Ota C, Kubo H, Nagatomi R. Ambroxol inhibits rhinovirus infection in primary cultures of human tracheal epithelial cells. Archives of Pharmacal Research. 2014; 37(4). doi: 10.1007/s12272-013-0210-7

107 Yan R, Zhang Y, Li Y, Xia L, Guo Y, Zhou Q. Structural basis for the recognition of SARS-CoV-2 by full-length human ACE2. Science. Published online 2020. doi: 10.1126/science.abb2762

108 Yan, R. et al. Structural basis for the recognition of SARS-CoV-2 by full-length human ACE2. Science (2020) doi:10.1126/science.abb2762.

109 Yang B, Yao D F, Ohuchi M, et al. Ambroxol suppresses influenza-virus proliferation in the mouse airway by increasing antiviral factor levels. European Respiratory Journal. 2002; 19(5). doi:10.1183/09031936.02.00253302

110 Yang N, Shen H M. Targeting the endocytic pathway and autophagy process as a novel therapeutic strategy in COVID-19. International Journal of Biological Sciences. 2020; 16(10). doi:10.7150/ijbs.45498

111 You, Z., Ran, X., Dai, Y. & Ran, Y. Clioquinol, an alternative antimicrobial agent against common pathogenic microbe. Journal de Mycologie Medicale 28, (2018).

112 Yu, H., Zhou, Y., Lind, S. E. & Ding, W. Q. Clioquinol targets zinc to lysosomes in human cancer cells. Biochemical Journal 417, (2009).

113 Zanasi A, Mazzolini M, Kantar A. A reappraisal of the mucoactive activity and clinical efficacy of bromhexine. Multidisciplinary Respiratory Medicine. 2017; 12(1). doi: 10.1186/s40248-017-0088-1

114 Zang R, Castro M F G, McCune B T, et al. TMPRSS2 and TMPRSS4 promote SARS-CoV-2 infection of human small intestinal enterocytes. Science Immunology. 2020; 5(47). doi:10.1126/sciimmunol.abc3582

115 Zhang, M. et al. Electrophysiologic Studies on the Risks and Potential Mechanism Underlying the Proarrhythmic Nature of Azithromycin. Cardiovasc Toxicol, https://DOI: 10.1007/s12012-017-9401-7 (2017).

116 Zhu, N. et al. A novel coronavirus from patients with pneumonia in China, 2019. New England Journal of Medicine 382, (2020).

What is claimed is:

1. A method for inhibiting or ameliorating a SARS-CoV-2 infection, comprising:
administering to a subject in need of inhibiting or ameliorating a SARS-CoV-2 infection a composition comprising an effective amount of one or more compounds selected from 5-chloro-7-iodoquinolin-8-ol (CLQ), 7-bromo-5-chloro-8-hydroxyquinoline (CLBQ14), 5,7-dichloro-8-hydroxyquinoline (CLCQ), or a pharmaceutically acceptable salt thereof.

2. The method of claim 1, wherein inhibiting or ameliorating a SARS-CoV-2 infection comprises one or more of:
inhibiting or ameliorating one or more SARS-CoV-2 infection induced cytopathic effects;
inhibiting or disrupting physical interaction of angiotensin converting enzyme 2 (ACE2) with SARS-CoV-2 spike glycoprotein;
blocking a pathway of SARS-CoV-2 entry into human cells via modulation of angiotensin converting enzyme 2 (ACE2) interaction with receptor binding domain protein of SARS-CoV-2; or
blocking angiotensin converting enzyme 2 (ACE2) exopeptidase function, thereby inhibiting ACE2 exopeptidase interaction with SARS-CoV-2 spike glycoprotein.

3. The method of claim 2, wherein the one or more compounds are administered one or more times a day for a daily dosage amount between 30 mg to 2,000 mg.

4. The method of claim 1, wherein the composition is administered in a tablets, capsule, syrup, dry powder sachets, inhalation solution, nebulization solution, drop, ampule, suppository, cream, or ointment.

5. The method of claim 1, Wherein the subject is administered 5-chloro-7-iodoquinolin-8-ol (CLQ).

6. The method of claim 1, wherein the subject is administered 7-bromo-5-chloro-8-hydroxyquinoline (CLBQ14).

7. The method of claim 1, wherein the subject is administered 5,7-dichloro-8-hydroxyquinoline (CLCQ).

* * * * *